US010583094B2

(12) United States Patent
Simard et al.

(10) Patent No.: US 10,583,094 B2
(45) Date of Patent: Mar. 10, 2020

(54) THERAPEUTIC METHODS THAT TARGET THE $NC_{CA-ATP}$ CHANNEL

(75) Inventors: J. Marc Simard, Baltimore, MD (US); Mingkui Chen, Omaha, NE (US)

(73) Assignees: University of Maryland, Baltimore, MD (US); The United States of America as Represented by the Department of Veterans Affairs, Washington, DC (US)

( * ) Notice: Subject to any disclaimer, the term of this patent is extended or adjusted under 35 U.S.C. 154(b) by 2035 days.

(21) Appl. No.: 11/574,793

(22) PCT Filed: Jul. 25, 2005

(86) PCT No.: PCT/US2005/026455
§ 371 (c)(1), (2), (4) Date: Oct. 30, 2008

(87) PCT Pub. No.: WO2006/036278
PCT Pub. Date: Apr. 6, 2006

(65) Prior Publication Data

US 2009/0130083 A1 May 21, 2009

Related U.S. Application Data

(60) Provisional application No. 60/610,758, filed on Sep. 18, 2004.

(51) Int. Cl.

| | |
|---|---|
| ***A61P 9/10*** | (2006.01) |
| ***A61K 38/43*** | (2006.01) |
| ***A61K 31/165*** | (2006.01) |
| ***A61K 31/565*** | (2006.01) |
| ***A61K 31/566*** | (2006.01) |
| ***A61K 31/00*** | (2006.01) |
| ***A61K 38/48*** | (2006.01) |
| ***A61K 31/40*** | (2006.01) |
| ***A61K 38/17*** | (2006.01) |
| ***A61K 31/175*** | (2006.01) |
| ***A61K 31/549*** | (2006.01) |
| ***A61K 31/64*** | (2006.01) |
| ***A61K 31/44*** | (2006.01) |
| ***A61K 45/06*** | (2006.01) |
| ***A61K 38/49*** | (2006.01) |
| *C07K 14/47* | (2006.01) |

(52) U.S. Cl.
CPC ............ *A61K 31/00* (2013.01); *A61K 31/165* (2013.01); *A61K 31/175* (2013.01); *A61K 31/40* (2013.01); *A61K 31/44* (2013.01); *A61K 31/549* (2013.01); *A61K 31/565* (2013.01); *A61K 31/566* (2013.01); *A61K 31/64* (2013.01); *A61K 38/177* (2013.01); *A61K 38/482* (2013.01); *A61K 38/49* (2013.01); *A61K 45/06* (2013.01); *A61P 9/10* (2018.01); *C07K 14/4705* (2013.01)

(58) Field of Classification Search
None
See application file for complete search history.

(56) References Cited

U.S. PATENT DOCUMENTS

| | | | |
|---|---|---|---|
| 5,047,429 | A | 9/1991 | Nye et al. |
| 5,166,162 | A | 11/1992 | Masereel et al. |
| 5,215,985 | A | 6/1993 | Murphy et al. |
| 5,236,932 | A | 8/1993 | Greenfield et al. |
| 5,281,599 | A | 1/1994 | Murphy et al. |
| 5,451,580 | A | 9/1995 | Murphy et al. |
| 5,545,656 | A | 8/1996 | Loose et al. |
| 5,677,344 | A | 10/1997 | Greenfield et al. |
| 5,811,393 | A | 9/1998 | Klagsbrun et al. |
| 5,849,796 | A | 12/1998 | Gericke et al. |
| 5,916,871 | A | 6/1999 | Johnson |
| 5,929,082 | A | 7/1999 | Chambers et al. |
| 5,962,645 | A | 10/1999 | Keay et al. |
| 6,043,224 | A | 3/2000 | Lee et al. |

(Continued)

FOREIGN PATENT DOCUMENTS

| | | |
|---|---|---|
| AU | 2003222020 A1 | 10/2003 |
| EP | 0 338 415 | 10/1989 |

(Continued)

OTHER PUBLICATIONS

Simard et al. 2006. Nature Medicine. 12(4): 433-440.*
Gribble et al, 2003. Diabetologia. 46(7): 875-891.*
Proks et al. 2002. European Journal of Pharmacology. 452: 11-19.*
Wise, 200. BMJ. 320: 823.*
Bereczki et al, 2007. Cochrane Database of Systematic Reviews. Issue 3, pp. 1-20.*
Toombs, 2001 (Current Opinion in Pharmacology. 1:164-168).*
Fan et al (2003. Brain Research. 993: 10-17; published Dec. 3, 2003).*
Graham et al (2003. Stroke 34: 2847-2850; published electronically on Nov. 6, 2003).*
European Patent Office Communication pursuant to Article 94(3) EPC, dated Dec. 10, 2008, during the prosecution of European Patent Application No. 05 812 199.7-2123.

(Continued)

*Primary Examiner* — Zachary C Howard
(74) *Attorney, Agent, or Firm* — Norton Rose Fulbright US LLP

(57) ABSTRACT

The present invention is directed to therapeutic compositions targeting the $NC_{Ca-ATP}$ channel of an astrocyte, neuron or capillary endothelial cell and methods of using same. More specifically, agonists and antagonists of the $NC_{Ca-ATP}$ channel are contemplated. The therapeutic compositions are used to treat cancer, more specifically, a metastatic brain tumor, wherein a tumor-brain barrier is present. Such treatments are contemplated in combination with conventional anti-cancer therapies. Alternatively, the compositions are used to prevent cell death and to treat cerebral edema that result from ischemia, due to interruption of blood flow, to tissue trauma or to increased tissue pressure.

54 Claims, 27 Drawing Sheets

Specification includes a Sequence Listing.

(56) References Cited

U.S. PATENT DOCUMENTS

| | | | |
|---|---|---|---|
| 6,100,047 A | 8/2000 | Wilkison et al. | |
| 6,156,522 A | 12/2000 | Keay et al. | |
| 6,180,671 B1 | 1/2001 | Freedman et al. | |
| 6,184,248 B1 | 2/2001 | Lee et al. | |
| 6,187,756 B1 | 2/2001 | Lee et al. | |
| 6,232,289 B1 | 5/2001 | Keay et al. | |
| 6,242,200 B1 | 6/2001 | Wilkison et al. | |
| 6,365,577 B1 | 4/2002 | Iversen | 514/44 |
| 6,372,743 B1 | 4/2002 | Darrow et al. | |
| 6,376,197 B1 | 4/2002 | Keay et al. | |
| 6,469,055 B2 | 10/2002 | Lee et al. | |
| 6,492,130 B1 | 12/2002 | Wilkison et al. | |
| 6,492,339 B1 | 12/2002 | Sleevi et al. | |
| 6,511,989 B2 | 1/2003 | Heitsch et al. | |
| 6,569,633 B1 | 5/2003 | Wilkison et al. | |
| 6,569,845 B1 | 5/2003 | Futamura et al. | |
| 6,596,751 B2 | 7/2003 | Fujita et al. | |
| 6,610,746 B2 | 8/2003 | Fryburg et al. | |
| 6,613,785 B2 | 9/2003 | Bril et al. | |
| 6,679,859 B1 | 1/2004 | Keipert et al. | |
| 7,285,574 B2 | 10/2007 | Simard et al. | |
| 7,877,048 B2 | 1/2011 | Kitagawa | |
| 8,318,810 B2 | 11/2012 | Simard et al. | |
| 8,980,952 B2 * | 3/2015 | Simard | A61K 31/00 514/317 |
| 2001/0003751 A1 | 6/2001 | Terashita et al. | |
| 2001/0016586 A1 | 8/2001 | Guitard et al. | |
| 2002/0013268 A1 | 1/2002 | Fryburg et al. | |
| 2002/0016443 A1 | 2/2002 | Keay et al. | |
| 2002/0037928 A1 | 3/2002 | Jaen et al. | |
| 2002/0065315 A1 | 5/2002 | Jensen et al. | |
| 2002/0081306 A1 | 6/2002 | Elliott et al. | |
| 2002/0094977 A1 | 7/2002 | Robl et al. | |
| 2003/0215889 A1 | 11/2003 | Simard et al. | |
| 2003/0216294 A1 | 11/2003 | Fryburg et al. | |
| 2005/0009733 A1 | 1/2005 | Stephenson et al. | |
| 2005/0054659 A1 | 3/2005 | Ellsworth et al. | |
| 2006/0100183 A1 | 5/2006 | Simard | 514/171 |
| 2006/0276411 A1 | 12/2006 | Simard et al. | |
| 2007/0203239 A1 | 8/2007 | Gehenne et al. | |
| 2009/0130083 A1 | 5/2009 | Simard et al. | |
| 2010/0092469 A1 | 4/2010 | Simard et al. | |
| 2010/0311639 A1 | 12/2010 | Simard | |
| 2011/0026347 A1 | 2/2011 | Fort et al. | |
| 2012/0237449 A1 | 9/2012 | Simard et al. | |

FOREIGN PATENT DOCUMENTS

| | | |
|---|---|---|
| EP | 0 467 709 | 1/1992 |
| EP | 0467709 A3 | 7/1992 |
| EP | 1782815 A1 | 5/2007 |
| ES | P200401628 | 6/2004 |
| JP | H09208562 A | 8/1997 |
| JP | 2004-516236 | 6/2004 |
| WO | WO 1997/041857 | 11/1997 |
| WO | WO-2001/10430 A2 | 2/2001 |
| WO | WO-01/54771 | 8/2001 |
| WO | WO-2002/070499 A2 | 9/2002 |
| WO | 03057843 A2 | 7/2003 |
| WO | 03075933 | 9/2003 |
| WO | WO-03/075933 A1 | 9/2003 |
| WO | 03079987 | 10/2003 |
| WO | WO-03/079987 | 10/2003 |
| WO | 2005/041877 A2 | 5/2005 |
| WO | 2006/000608 A1 | 1/2006 |
| WO | WO-2006/000608 | 1/2006 |
| WO | WO 2006/000608 | 1/2006 |
| WO | 2006/034048 A2 | 3/2006 |
| WO | 2007011926 A2 | 1/2007 |
| WO | WO-2007/011595 A2 | 1/2007 |
| WO | 2007058902 | 5/2007 |
| WO | WO-2006/036278 A8 | 5/2007 |
| WO | WO-2007 058902 | 5/2007 |
| WO | WO 2008/089103 | 7/2008 |
| WO | WO-2008/098160 A1 | 8/2008 |
| WO | WO-2009/002832 A2 | 12/2008 |

OTHER PUBLICATIONS

Rosenberg, Gary A.; "Ischemic Brain Edema"; Progress in Cardiovascular Diseases, vol. 42, No. 3 (November/December), 1999: pp. 209-216.

Supplementary European Search Report dated Jun. 19, 2008 during the prosecution of European Application No. 03 71 8003.

Rothstein et al, "Neuroprotective strategies in a model of chronic glutamate-mediated motor neuron toxicity," J Neurochem. Aug. 1995;65(2):643-51.

Israel Office Action, dated Feb. 15, 2010 (published Feb. 15, 2010) during the prosecution of International Application No. 181740.

Sang et al., "ATP sensitive potassium channels are involved in the protective effect of ischemic preconditioning on spinal cord in rabbits"; Chinese Pharmacological Bulletin, 2003, Issue 12, 1362-1365.

Notification of the First Office Action dated Jan. 22, 2010 during prosecution of Chinese Patent Aplication No. 200580036055.7 (English Translation).

European Patent Office Communication Pursuant to Article 94(3) EPC dated Jan. 16, 2009, regarding EP Application No. 05 805 849.6-2123.

Aguilar-Bryan et al., "Cloning of the beta cell high-affinity sulfonylurea receptor: a regulator of insulin secretion," *Science,* 268: 423-426, 1995.

Ahmad et al., "Mouse cortical collecting duct cells show nonselective cation channel activity and express a gene related to the cGMP-gated rod photoreceptor channel," *Proc. Natl. Acad. Sci. USA,* 89: 10262-10266, 1992.

Angel et al., "The binding site for [3H]glibenclamide in the rat cerebral cortex does not recognize K-channel agonists or antagonists other than sulphonylureas," *Fundam. Clin. Pharmacol,* 5(2): 107-15, 1991 (abstract only).

Annex to Form PCT/ISA/206, Communication Relating to the Results of the Partial International Search, regarding International Application No. PCT/US2005/026455, dated Oct. 12, 2006.

Armijo, "Advances in the physiopathology of epilegtogenesis: molecular aspects," *Rev. Neurol.,* 34(5): 409-29, 2002 (abstract only).

Auger, G. et al; Purification and Partial Characterization of a Hepatocyte Antiproliferative Glycopeptide, Journal of Cellular Biochemistry, (1989) vol. 40, pp. 439-451.

Ballerini, "Glial cells express multiple ATP binding cassette proteins which are involved in ATP release," *Neuroreport,* 13(14): 1789-92, 2002 (abstract only).

Bareyre et al., "Inflammation, degeneration and regeneration in the injured spinal cord: insights from DNA microarrays," *Trends Neurosci.,* 26(10): 555-563, 2003.

Bartholdi et al., "Expression of pro-inflammatory cytokine and chemokine mRNA upon experimental spinal cord injury in mouse: an in situ hybridization study," *Eur. J. Neurosci.,* 9(7): 1422-1438, 1997.

Baudelet et al., "Evidence for a Neuroprotective Effect of Pyrid-3-yl-sulphonyl-urea in Photochemically Induced Focal Ischaemia in Rats: Magnetic Resonance Imaging Evaluation," *J. Pharm. Pharmacol.,* 51: 967-970, 1999.

Beier-Holgersen, R., "The in vitro cytotoxicity of urine from patients with interstitial cystitis", Journal of Urology (Jan. 1994), vol. 151, pp. 206-207.

Bevan et al, "Voltage Gasted Ionic Channels in Rat Cultured Astrocytes, Reactive Astrocytes and an Astrocyte-oligodendrocyte Progenitor Cell, " J. Physiol vol. 82, 1987, pp. 327-335.

Champigny et al., "A voltage, calcium, and ATP sensitive non selective cation channel in human colonic tumor cells," *Biochem. Biophys. Res. Commun.,* 176: 1196-1203, 1991.

Chen et al, "Cell Swelling and a Nonselective Cation Channel Regulated by Internal CA2+ and ATP in Native Reactive Astrocytes from Adult Rat Brain," The Journal of Neuroscience vol. 21 No. 17, Sep. 1, 2001, pp. 6512-6521.

(56) References Cited

OTHER PUBLICATIONS

Chen et al., "A Calcium-Activated Nonspecific Cation Channel in Reactive Astrocytes from Adult Rat Brain," Society for Neuroscience Abstracts, vol. 26, No. 1-2, Abstract No. 791.1, 2000 [abstract].
Chen et al., "Functional coupling between sulfonylurea receptor type 1 and a nonselective cation channel in reactive astrocytes from adult rat brain," *J. Neurosci.*, 23: 8568-8577, 2003.
Copin et al., "70-kDa heat shock protein expression in cultured rat astrocytes after hypoxia: regulatory effect of almitrine," *Neurochem. Res.*, 20(1): 11-15, 1995.
Corrected International Search Report dated Sep. 18, 2008 during the prosecution of International Application No. PCT/US07/62392.
Csanady et al., "Ca(2+)- and voltage-dependent gating of Ca(2+)- and ATP-sensitive cationic channels in brain capillary endothelium," *Biophys. J.*, 85: 313-327, 2003.
Currie et al., "Benign focal ischemic preconditioning induces neuronal Hsp70 and prolonged astrogliosis with expression of Hsp27," *Brain Res.*, 863(1-2): 169-181, 2000.
Davies, "Insulin secretagogues," *Curr. Med. Res. Opin. 18 Suppl.*, 1: ss22-30, 2002 (abstract only).
Fujita et al., "Molecular aspects of ATP-sensitive K+ channels in the cardiovascular system and K+ channel openers," *Pharmacol. Ther.*, 85: 39-53, 2000.
Gopalakrishnan et al., "Pharmacological characterization of a 1,4-dihydropyridine analogue, 9-(3,4-dichorophenyl)-3,3,6,6-tetramethyl-3,4,6,7,9,10-hexahydro-1,8(2H,5H)-acridinedione (A-184209) as a novelK(ATP) channel inhibitor," *Br. J. Pharmacol.*, 138(2): 393-99, 2003 (abstract only).
Gray et al., "Non-selective cation channel on pancreatic duct cells," *Biochem. Biophys. Acta,* 1029:33-42, 1990.
Gribble et al., "Differential selectivity of insulin secretagogues. Mechanisms, clinical implications, and drug interactions," *J. Diabetes Complications,* 17(2 Suppl): 11-5, 2003 (abstract only).
Gribble et al., "Tissue Specificity of Sulfonylureas: Studies on Cloned Cardiac and B-Cells K-ATP Channels," *Diabetes,* 47: 1412-1418, 1998.
Haider et al., "Identification of the PIP2-binding site on Kir6.2 by molecular modelling and functional analysis," EMBO J. Aug. 22, 2007;26(16):3749-59. Epub Aug. 2, 2007.
Hambrock et al., "Four novel splice variants of sulfonylurea receptor 1," *Am. J. Physiol. Cell Physiol.*, 283: C587-0598, 2002.
Hernandez-Sanchez et al., "Mice transgenically overexpressing sulfonylurea receptor 1 in forebrain resist seizure induction and excitotoxic neuron death," *PNAS,* 98(6): 3549-3554, 2001.
Inagaki et al., "A family of sulfonylurea receptors determines the pharmacological properties of ATP-sensitive K+ channels," *Neuron,* 16: 1011-1017, 1996.
International Preliminary Report on Patentability dated Oct. 21, 2008 during the prosecution of International Application No. PCT/US07/62392.
Isomoto et al., "A novel sulfonylurea receptor forms with BIR (Kir6.2) a smooth muscle type ATP-sensitive K+ channel," *J. Biol. Chem.*, 271: 24321-24324, 1996.
Jarvis et al., "Purinergic Mechanisms in the Nervous System Function and Disease States," Psychopharmacology: The Fourth Generation of Progress, (Kupfer, David J. et al., Lippincott 2000), found at www.acnp.org/g4/GN401000063/CH.html.
Kakimura et al., "Microglial activation and amyloid-beta clearance induced by exogenous heat-shock proteins," *FASEB J.,* 16(6): 601-603, 2002.
Keay, S., et al.; Bladder Epithelial Cells from Patients with Interstitial Cystitis Produce an Inhibitor of Heparin-Binding Epidermal Growth Factor-Like Growth Factor Production, The Journal of Urology (Dec. 2000) vol. 164, pp. 2112-2118.
Keay, S., et al.; Changes in human bladder epithelial cell gene expression asscoiated with interstitial cystitis or antiproliferative factor treatment, Physiol. Genomics (2003) vol. 14, pp. 107-115.
Keay, S., et al.; Current and future directions in diagnostic markers in interstitial cystitis, Intern'l J. of Urology (2003) vol. 10, pp. S27-230.
Keay, S., et al.; Decreased In Vitro Proliferation of Bladder Epithelial Cells from Patients with Interstitial Cystitis, The Journal of Urology (2003) vol. 61, pp. 1278-1284.
Kimelberg et al., "Astrocytic swelling in traumatic-hypoxic brain injury. Beneficial effects of an inhibitor of anion exchange transport and glutamate uptake in glial cells," *Mol. Chem. Neuropathol.*, 11(1): 1-31, 1989 (abstract only).
Koch et al., "Mechanism of shrinkage activation of nonselective cation channels in M-1 mouse cortical collecting duct cells," *J. Membr. Biol.*, 177(3): 231-42, 2000 (abstract only).
Koch et al., "Osmotic shrinkage activates nonselective cation (NSC) channels in various cell types," *J. Membr. Biol.*, 168(2): 131-39, 1999 (abstract only).
Lauritzen et al., "The potassium channel opener (-)-cromakalim prevents glutamate-induced cell death in hippocampal neurons," *J. Neurochem.*, 69(4): 1570-79, 1997 (abstract).
Lee et al, "Upregulation of Phospolipase D in Astrocytes in Response to Transient Forebrain Ischemia," GLIA vol. 30, 2000, pp. 311-317.
Lee et al., "Differential neuroprotection from human heat shock protein 70 overexpression in in vitro and in vivo models of ischemia and ischemia-like conditions," *Exp. Neurol.*, 170(1): 129-139, 2001.
Lee et al., "Direct demonstration of sulphonylurea-sensitive KATP channels on nerve terminals of the rat motor cortex," *Br. J. Pharmacol.*, 115(3): 385-87, 1995 (abstract only).
Lee et al., "In vitro Antitumor Activity of Cromakalim in Human Brain Tumor Cells," *Pharmacology,* 49: 69-74, 1994.
Lee et al., "The high-affinity sulphonylurea receptor regulates KATP channels in nerve terminals of the rat motor cortex," *J. Neurochem.*, 66(6): 2562-71, 1996 (abstract only).
Liu et al., "Tenidap, a novel anti-inflammatory agent, is an opener of the inwardly rectifying K+ channel hKir2.3," *Eur. J. Pharmacol.*, 435(2-3): 153-60, 2002 (abstract only).
Matz et al., "Heme-oxygenase-1 induction in glia throughout rat brain following experimental subarachnoid hemorrhage," *Brain Res.*, 713(1-2): 211-222, 1996.
Mautes et al., "Co-induction of HSP70 and heme oxygenase-1 in macrophages and glia after spinal cord contusion in the rat," *Brain Res.*, 883(2): 233-237, 2000.
Mautes et al., "Sustained induction of heme oxygenase-1 in the traumatized spinal cord," *Exp. Neurol.*, 166(2): 254-265, 2000.
Mest et al., "Glucose-induced insulin secretion is potentiated by a new imidazoline compound," *Naunyn Schmledebergs Arch. Pharmacol.*, 364(1): 47-52, 2001 (abstract only).
Nichols et al., "Adenosine diphosphate as an intracellular regulator of insulin secretion," *Science,* 272: 1785-1787, 1996.
No Author Named; APO-Glibenclamide Data Sheet, Medsafe (New Zealand Medicines and Medical Devices Safety Authority), published Jun. 16, 1999, 6 pages; online <http://www.medsafe.govt.nz/Profs/DataSheet/a/Apoglibenclamidetab.htm>.
Ono et al., "ATP and calcium modulation of nonselective cation channels in IMCD cells," *Am. J. Physiol.*, 267: F558-F565, 1994.
Papadopoulos et al., "Over-expression of HSP-70 protects astrocytes from combined oxygen-glucose deprivation," *Neuroreport,* 7(2): 429-432, 1996.
Parsons, C.L., et al., "Role of Toxic Urine in Interstitial Cystitis", Journal of Urology (1990) vol. 143, p. 373A.
Perillan et al., "Inward Rectifier K+ Channel Kir2.3 (IRK3) in Reactive Astrocytes from Adult Rat Brain," *GLIA,* 31: 181-192, 2000.
Perillan et al., "K+ Inward Rectifier Currents in Reactive Astrocytes from Adult Rat Brain," *GLIA,* 27: 213:225, 1999.
Perillan et al., "Transforming Growth Factor-B1 Regulates Kir2.3 Inward Rectifier K+ Channels via Phospholipase C and Protein Kinase C-d in Reactive Astrocytes from Adult Rat Brain," *J. Biol. Chem.*, 277: 1974-1980, 2002.
Popp et al, "A Calcium and ATP Sensitive Nonselective Cation Channel in the Antiluminal Membrane of Rat Cerebral Capillary Endothelial Cells," Biochimica et Biophysica Acta vol. 1108, 1992, pp. 59-66.
Proks et al., "Sulfonylurea stimulation of insulin secretion," *Diabetes,* 51(Suppl. 3): S368-76, 2002 (abstract only).

(56) References Cited

OTHER PUBLICATIONS

Rae et al., "A non-selective Cation Channel in Rabbit Corneal Endothelium Activated by Internal Calcium and Inhibited by Internal ATP," *Exp. Eye. Res.*, 50: 373-384, 1990.
Rashid, H., et al; Interstitial cystitis antiproliferative factor (APF) as a cell-cycle modulator, BMC Urology (2004) 4:3, pp. 1-5.
Regan et al., "Heme oxygenase-1 induction protects murine cortical astrocytes from hemoglobin toxicity," *Neurosci. Lett.*, 282(1-2): 1-4, 2000.
Schroder et al., "AMPA receptor-mediated modulation of inward rectifier K+ channels in astrocytes of couse hippocampus," *Mol. Cell Neurosci.*, 19(3): 447-8, 2002 (abstract only).
Schubert et al., "Cascading glia reactions: a common pathomechanism and its differentiated control by cyclic nucleotide signaling," *Ann. N.Y. Acad. Sci.*, 903: 24-33, 2000 (abstract only).
Shyng et al., "Regulation of KATP channel activity by diazoxide and MgADP. Distinct functions of the two nucleotide binding folds of the sulfonylurea receptor," *J. Gen. Physiol.*, 110: 643-654, 1997.
Simard et al., "Endothelial sulfonylurea receptor 1-regulated NC Ca-ATP channels mediate progressive hemorrhagic necrosis following spinal cord injury," J Clin Invest. Aug. 2007;117(8):2105-13.
Simard et al., "Regulation by sulfanylurea receptor type 1 of a non-selective cation channel involved in cytotoxic edema of reactive astrocytes," *J. Neurosurg. Anesthesiol.*, 16(1): 98-9, 2004.
Slikker et al., "Session IV: Models of Neurotoxicity and Neuroprotection, Questions for Dr. Banik", Ann NY Acad Sci; 2003; 993; 159-160.
Song et al., "GeneChip analysis after acute spinal cord injury in rat," *J. Neurochem.*, 79(4): 804-815, 2001.
Sribnick et al., "Estrogen as a Neuroprotective Agent in the Treatment of Spinal Cord Injury", Ann. N.Y. Acad. Sci., vol. 993;. 2003;125-133.
Sturgess et al., "Calcium and ATP regulate the activity of a non-selective cation channel in a rat insulinoma cell line," *Pflugers Arch.*, 409: 607-615, 1987.
Supplementary European Search Report issued during the prosecution of European Application EP 05 81 1299, dated Aug. 27, 2008.
Vidal, "Making sense of antisense", Eur. J. Cancer, 2005; 2812-8; vol. 41(18).
Weih et al., "Sulfonylurea Drugs Do Not Influence Initial Stroke Severity and In-Hospital Outcome in Stroke Patients With Diabetes", Stroke. 2001;32:2029-2032.
Written Opinion dated Sep. 18, 2008 during the prosecution of International Application No. PCT/US07/62392.
Xu et al., "HSP70 protects murine astrocytes from glucose deprivation injury," *Neurosci. Lett.*, 224(1): 9-12, 1997.
Zhang, C., et al; Comparison of APF Activity and Epithelial Growth Factor Levels in Urine from Chinese, African-American, and White American Patients with Intestitial Cystitis, Urology (2003) vol. 61, pp. 897-901.
Canadian Office Action dated Nov. 4, 2009 during the prosecution of Canadian Patent Application No. 2,477,812.
Second Office Action, dated Jul. 30, 2010 (published Jul. 30, 2010) during the prosecution of Chinese Application No. 200580036055.7.
Japanese Office Action, issued in Japanese Patent Application No. 2007-532321, dated Apr. 22, 2011.
PCT International Preliminary Report on Patentability, issued in International application No. PCT/US2009/057111, dated Mar. 31, 2011.
Khan Hussein Hamed, et al.; "Comparison of Therapeutic Effects by K+ Channel Opener Minoxidil and Blocker Glyburide on Cerebral Ischemia Produced by MCAO and Levo-thyroxine in Rats"; Journal of China Pharmaceutical University; Jan. 2000; vol. 31(4); pp. 289-293.
Crépel et al., "Glibenclamide depresses the slowly inactivating outward current ($I_D$) in hippocampal neurons," *Canadian Journal of Physiology and Pharmacology,* 70(2):306-307, 1992.
Extended European Search Report issued in European Application No. 10010753.1, dated Oct. 26, 2011.
Gribble and Ashcroft, "Sulfonylurea sensitivity of adenosine triphosphate-sensitive potassium channels from β cells and extrapancreatic tissues," *Metabolism,* 49(10Supp2):3-6, 2000.
Grijalva et al., "Efficacy and safety of 4-aminopyridine in patients with long-term spinal cord injury: a randomized, double-blind, placebo-controlled trial," *Pharmacotherapy,* 23(7):823-834, 2003.
Hozumi et al., "Biochemical and immunocytochemical changes in glial fibrillary acidic protein after stab wounds," *Brain Research,* 524:64-71, 1990.
Liu et al., "Suppression of hippocampus Fos expression and activator protein-1 (AP-1) activity during focal cerebral ischemia using antisense strategy," *Stroke,* 26(1):182, 1995.
Office Action issued in Japanese Application No. 2007-532507, dated Jun. 20, 2011.
Partial European Search Report issued in European Application No. 10010753.1, dated Jul. 22, 2011.
Wickelgren, "Animal studies raise hopes for spinal cord repair," *Science,* 297:178-181, 2002.
Yokoshiki et al., "Antisense oligodeoxynucleotides of sulfonylurea receptors inhibit ATP-sensitive $K^+$ channels in cultured neonatal rat ventricular cells," *Pflugers Arch— Eur J Physiol,* 437:400-408, 1999.
Simard, J. M., et al. "Newly expressed SUR1-regulated NCCa-ATP channel mediates cerebral edema after ischemic stroke", Nature Medicine, Nature Publishing Group, New York, NY, US, vol. 12, No. 4, pp. 443-440, Apr. 1, 2006.
Verkhratsky et al., "Ion channels in glial cells," Brain Res. Rev., 32: 380-412, 2000.
Simard, J., et. al., "Molecular pathophysiology of brains edema in focal ischemia—a focused review" (Apr. 8, 2006) pp. 1-483.
Walaas et al., PCPP-260, A Purkinje Cell-Specific Cyclic AMP-Regulated Membrane Phosphoprotein of Mr 260,000, J Neurosci. Apr. 1986;6(4):954-61.
Rosenberg, "Ischemic brain edema." Prog Cardiovasc Dis. Nov.-Dec. 1999; vol. 42(3):209-16.
APO-Glibenclamide Data Sheet, Medsafe (New Zealand Medicines and Medical Devices Safety Authority), published Jun. 16, 1999, 6 pages; online http://www.medsafe.govt.nz/Profs/DataSheet/a/Apoglibenclamidetab.htm.
Weih et al., "Sulfonylurea Drugs Do Not Influence Initial Stroke Severity and In-Hospital Outcome in Stroke Patients With Diabetes", Stroke. 2001; vol. 32(9):2029-2032.
Lee et al., "In vitro Antitumor Activity of Cromakalim in Human Brain Tumor Cells," Pharmacology 1994; vol. 49:69-74.
Yune et al., "Systemic Administration of 17?-Estradiol Reduces Apoptotic Cell Death and Improves Functional Recovery following Traumatic Spinal Cord Injury in Rats", Journal of Neurotrauma. Mar. 1, 2004, 21(3): 293-306.
Gagliardino, J.J. et al.; Inhibitory effect of sulfonylureas on protein phosphatase activity in rat pancreatic islets; Acta Diabetol (1997) 34:6-9; Springer-Verlang 1997.
Medline Plus® Merriam Webster Medical Dictionary, main entry: par.en.ter.al, online <http://www2.merriam-webster.com/cgi-bin/mwmednlm>; 2005; 1 page.
Maybaur, D.M., et al, "The ATP-sensitive Potassium-channel Inhibitor Glibenclamide Improves Outcome in an Ovine Model of Hemorragic Shock," Shock, vol. 22(4), 2004, pp. 387-391.
Simard, J. M., et al.; "Glibenclamide Reduces Inflammation, Vasogenic Edema, and Caspase-3 Activation After Subarachnoid Hemorrhage"; Journal of Cerebral Blood Flow & Metabolism (2008), 29(2) pp. 317-330.
Simard, J. M., et al.; "Sulfonylurea Receptor 1 in the Germinal Matrix of Premature Infants"; Pediatr Res.; Dec. 2008; 64(6), pp. 648-52.
Wang, H., et al., "Targeting Ischemic Stroke with a Novel Opener of ATP-Sensitive Potassium Channels in the Brain", Molecular Pharmacology, vol. 66(5), 2004, pp. 1160-1168.
Koltz, Michael T., et al; "Tandem Insults of Prenatal Ischemia Plus Postnatal Raised Intrathoracic Pressure in a Novel Rat Model of Encephalopathy of Prematurity"; J. Neurosurg. Pediatrics, Dec. 2011, vol. 8, pp. 628-639.

(56) References Cited

OTHER PUBLICATIONS

Kraemer, Jennifer, et al; "Perfusion Studies of Glyburide Transfer Across the Human Placenta: Implications for Fetal Safety"; American Journal of Obstetrics and Gynecology, 2006, vol. 195, pp. 270-274.
Elliott, Byron D., et al; "Comparative Placental Transport of Oral Hypoglycemic Agents in Humans: A Model of Human Placental Drug Transfer"; Am. J. Obstet. Gynecol., Sep. 1994, vol. 171, No. 3, pp. 653-660.
Elliott, Byron D., et al; "Insignificant Transfer of Glyburide Occurs Across the Human Placenta"; Oct. 1991; Am. J. Obstet. Gynecol., vol. 165, No. 4, Part 1, pp. 807-812.
Koren, Gideon; "Glyburide and Fetal Safety; Transplacental Pharmacokinetic Considerations"; Reproductive Toxicology, 2001, vol. 15, pp. 227-229.
Tosun, Cigdem, et al; "The Protective Effect of Glibenclamide in a Model of Hemorrhagic Encephalopathy of Prematurity"; Brain Sciences, 2013, vol. 3, pp. 215-238.
Mizognchi et al., "Inhibition of Carbonic Anydrases Enhanced the Recovery from Acute Experimental colitis by Controlling Epithelial Registration", Abstract In: Elsevier Health Journals, p. 821, 2003.
Kawaguchi et al., "A case of hemorrhagic colitis associated with flufenamic acid aluminium", Japanese Journal of National Medical Services, 47(12):999-1003, 1993.
Gunal et al., "Estradiol Treatment Ameliorates Acetic Acid-Induced Gastric and Colonic Injuries in Rats", Inflammation, 27(6):351-359, 2003.
Jin et al., "Altered gene expression and increased bursting activity of colonic smooth muscle ATP-sensitive K+ channels in experimental colitis", Am. J. Physiol. Gastrointest. Liver Physiol., 287:G274-G285, 2004.
Daneshmand et al., "Chronic lithium administration ameliorates 2,4,6-trinitrobenzene sulfonic acid-induced colitis in rats; potential role for adenosine triphosphate sensitive potassium channels", Gastroenterology and Hepatology, 26:1174-1181, 2011.
Nieuwenhuijs et al., "Hepatic ischemia-reperfusion injury: roles of Ca2+ and other intracellular mediators of impaired bile flow and hepatocyte damage"; Digestive Diseases and Sciences, Jun. 2006, vol. 51(6); 1087-102.
Pompermayer et al.; "The ATP-sensitive potassium channel blocker glibenclamide prevents renal ischemia/reperfusion injury in rats"; Kidney International, May 2005, vol. 67(5); 1785-96.
Kim, H.J., et al.; "Anthocyanins from soybean seed coat inhibit the expression of TNF-alpha-induced genes associated with ischemia/reperfusion in endothelial cell by NF-kappaB-dependent pathway and reduce rat myocardial damages incurred by ischemia and reperfusion in vivo"; FEBS Letters 580, Jan. 20, 2006; pp. 1391-1397.
Fagan et al., "Targets for vascular protection after acute ischemic stroke"; Stroke. Sep. 2004;35(9):2220-5. Epub Jul. 29, 2004.
Gürsoy-Özdemir et al., "Role of Endothelial Nitric Oxide Generation and Peroxynitrite Formation in Reperfusion Injury After Focal Cerebral Ischemia"; Stroke. 2000;31:1974.
Manley et al., "Aquaporin-4 deletion in mice reduces brain edema after acute water intoxication and ischemic stroke"; Nature Medicine 6, 159-163 (2000).
Morris et al., "Extension of the Therapeutic Window for Recombinant Tissue Plasminogen Activator With Argatroban in a Rat Model of Embolic Stroke"; Stroke. 2001;32:2635-2640.
Nilius et al., "Transient Receptor Potential Cation Channels in Disease"; Physiol. Rev. 87: 165-217, 2007.
Pisano et al., "Undersulfated, low-molecular-weight glycol-split heparin as an antiangiogenic VEGF antagonist"; Glycobiology 2005 15(2):1C-6C.
Rosenberg et al., "TIMP-2 reduces proteolytic opening of blood-brain barrier by type IV collagenase" Brain Res—Apr. 3, 1992; 576(2): 203-7.
Ullrich et al., "Comparison of functional properties of the Ca2+-activated cation channels TRPM4 and TRPM5 from mice"; Cell Calcium. Mar. 2005; 37(3):267-78.
Grand, T., et al; "9-Phenanthrol Inhibits Human TRPM4 But Not TRPM5 Cationic Channels"; British Journal of Pharmacology; 2008, vol. 153, vol. 1697-1705.
Matsuo, Michinori, et al; "Different Binding Properties and Affinities for ATP and ADP Among Sulfonylurea Receptor Subtypes, SUR1, SUR2A, and SUR2B*"; The Journal of Biological Chemistry; Sep. 15, 2000; vol. 275, No. 37, pp. 28757-28763.
Nilius, Bernd, et al; "Intracellular Nucleotides and Polyamines Inhibit the Ca2+-Activated Cation Channel TRPM4b"; Pfulgers Arch—Eur. J. Physiol., 2004, vol. 448; pp. 70-75.
Babenko; Audrey P., et al; "Pharmaco-topology of Sulfonylurea Receptors"; The Journal of Biological Chemistry (Accelerated Publication); vol. 275, No. 2, Jan. 14, 2000, pp. 717-720.
Earley, Scott, et al; "Protein Kinase C Regulates Vascular Myogenic Tone Through Activation of TRPM4"; American Physiological Society; Feb. 9, 2007; vol. 292; pp. H2613-H2622.
Woo, Seung Kyoon, et al; "The Sulfonylurea Receptor 1 (Sur1)-Transcient Receptor Potential Melastatin 4 (Trpm4) Channel"; The Journal of Biological Chemistry, Feb. 1, 2013, vol. 288, No. 5, pp. 3655-3667.
Pfeiffer et al., "Controlled extension of oral antidiabetic therapy on former insulin dependent diabetics by means of the combined i.v . . . Glibenclamide-glucose-response test", Diabetologia, 8:41-47, 1972.
Wise, "New clinical guidelines for stroke published", BMJ, 320:823, 2000.
Bereczki et al., "Mannitol for acute stroke (Review)", Cochrane Database of Systematic Reviews, Issue 3, p. 1-20, 2009.
Chen et al., "Fenamates protect neurons against ischemic and exitotoxic injury in chick embryo retina", Neuroscience Letters, 242(3):163-166, 1998.
Riddle, "Editorial: sulfonylureas differ in effects on ischemic preconditioning—is it time to retire glyburide?", The Journal of Clincial Endocrinology & Metabolism, 2003, 88(2):528-530.
Gurke et al., "Mechanisms of ischemic preconditionin in skeletal muscle", Journal of Surgical Research, 2000, 94:18-27.
Greenwood et al., "Comparison of the effects of fenamates on Ca-activated chloride and potassium currents in rabbit portal vein smooth muscle cells" Biritish Journal of Pharmacology, 116:2939-2948, 1995.
Schmidt et al., "Endocrine and metabolic consequences of spinal injuries", Chapter 18, Sprinal Coard Medicine; Principles and Practices, pp. 221-235, 2002.
Launary et al., "TRPM4 Regulates Calcium Oscillations After T Cell Activation", Science, 306(5700):1374-1377, 2004.
Definition of "infusion" from www.merriam-webster.com, printed on Apr. 10, 2013, 1 pages as printed.
Heurteaux et al., "Alpha-Linolenic Acid and Riluzole Treatment Confer Cerebral Protection and Improce Survival After Focal Brain Ischemia", Neuroscience, 137:241-251, 2006.
Simard et al., Comparative effects of glibenclamide and riluzole in a rat model of severe cervical spinal cord injury, Experimental Neurology, 233:566-574, 2012.
Demion et al., "TRPM4, a Ca2+-activated nonselective cation channel in mouse sino-atrial nod cells", Cardiovasuclar Research, 73:531-538, 2007.
Khansari, "An investigation of the neuroprotective properties of fenamate NSAIDs, against experimental models of ischemic stroke", Dissertation Abstracts International, 68:11B, 197 pages, 2007.
Khansari and Halliwell, "Evidence for neuroprotection by the fenamate NSAID, mefenamic acid", Neurochemistry International, 55:683-688, 2009.
Klose et al., "Fenamates as TRP channel blockers: mefenamic acid selectively blocks TrPM3", British Journal of Pharmacology, 162:1757-1769, 2011.
Pirollo and Chang, "Targeted Delivery of Small Interfering RNA: Approaching Effetive Cancer Therapies", Cancer Res., 68(5):1247-1250, 2008.
Hausmann, "Post-traumatic inflammation following spinal cord injury", Spinal Cord, 41:369-378, 2003.
Woodcock, "The role of markers of inflammation in traumatic brain injury", Frontiers in Neurology, 4:1-18, 2013.

(56) References Cited

OTHER PUBLICATIONS

Hugelshofer, "Neuroinflammation after Subarachnoid Hemorrhage: The Role of Microglia", UniversitatsSpital Zurich Institut fur Neuropathologie & Klinik fur Neurochirurgie, p. 1-18, 2013.
Hallevi, "Inflammatory response to intraventricular hemorrage: Time course, magnitude and effect of t-Pa," Journal of the Nurological Science, 315:93-95, 2012.
Kunte et al., "Sulfonylureas Improve Outcome in Patients With Type 2 Diabetes and Acute Ischemic Stroke", Stroke, 38(9):2526-2530, 2007.
Liang et al., Neurosurg Focus, 22(5):E2, pp. 1-16, 2007.
Gavin, "Management of Diabetes Mellitus During Surgery", West J M. 151:525-529, 1989.
Vestergaard et al., "Relative fracture risk in patients with diabetes melitus, and the impact of insulin and oral antidiabetic medication on relative fracture risk", Diabetologia, 48:1292-1299, 2005.
Inder and Volpe, "Mechanisms of Perinatal Brain Injury", 5 Semin, Neonatol. 3, 2000.
Wright et al., Evidence from Multicenter Networks on the Current Use and Effectiveness of Antenantal Corticosteroids in Low Birth Weight Infants, Am. J Obstet. Gynecol., 173:263, 1995.
Egarter et al., "Antibiotic Treatment in Preterm Premature Rupture of Membranes and Neonatal Morbidity: A Metaanalysis", Am. J. Obstet. Gynecol., 174:589, 1996.
Huss et al., "Differentiation of canine bone marrow cells with hemopoietic characteristics from an adherent stromal cell precursor", Proc natl. Acad. Sci USA, 92:748-752, 1995.
Benos, "Methods to study CFTR protein in vitro", Journal of Cystic Fibrosis; 2004; 79-83; vol. 3.
Chen, M., et al., "Glial and Other Non-Neuronal Cell Specification and Differentiation IV", Society for Neuroscience, (2000) vol. 26, pp. 791.1.
Gribble et al., "The interaction of nucleotides with the tolbutamide block of cloned ATP-sensitive K+ channel currents expressed in Xenopus oocytes: a reinterpretation", J Physiol.; 1997; 35-45; vol. 504(Pt 1).
Gribble, "Sulphonylurea action revisited: the post-cloning era", Diabetologia, 2003; 875-91. vol. 46(7).
Hambrock, A., et al., "Mg2+ and ATP dependence of KATP Channel Modulator Binding to the Recombinant Sulphonylurea Receptor, SUR2B", *British Journal of Pharm.* 91998), vol. 125, pp. 577-583.
Jamme, Focal cerebral ischaemia induces a decrease in activity and a shift in ouabain affinity of Na+, K+-ATPase isoforms without modifications in mRNA and protein expression, Brain Res.; 1999; 132-42; vol. 819(1-2).
Kaal, et al., "The Management of Brain Edema in Brain Tumors", *Curr. Opin. Oncol.;* 2004; 593-600; vol. 16.
Kawanabe, Yoshifumi, et al., "Effects of the Ca++-permeable Non-selective Cation Channel Blocker LOE 908 on Subarachnoid Hemorrhage-induced Vasospasm in the Basilar Artery in Rabbits", Experimental Biology and Medicine, Mar. 2003, XP008150600.
Kempski, "Cerebral Edema", *Semin Nephol;* 2001; 303-307; vol. 21 (3); abstract only.
Lin, et al., "17b-Estradiol Inhibits Endothelin-1 Production and Attenuates Cerebral Vasospasm After Expreimental Subarachnoid Hemorrhage", Experimental Biology and Medicine, Jun. 1, 2006, pp. 1054-1057, XP55024011, URL:http://ebm.rsmjournals.com/content/231/6/1054.full.pdf#page=1&view=FitH [retrieved Apr. 5, 2012].
Löffler-Walz et al., Interaction of the Diuretics Torasemide and U-37883A with the K(ATP) Channel in Rat Isolated Aorta, Naunyn Schmiedebergs Arch Pharmacol. Aug. 1998;358(2):230-7.
Maeda, Yoshihisa, et al. "Endothelial Dysfunction and Altered Bradykinin Response Due to Oxidative Stress Induced by Serum Deprivation in the Bovine Cerebral Artery", European Journal of Pharmacology, Elsevier Science, NL, vol. 491, No. 1, Apr. 26, 2004, pp. 53-60, XP008150602, ISSN 0014-2999.
Nishimura et al., "Cerebral ATP-Sensitive Potassium Channels During Acute Reduction of Carotid Blood Flow," Hypertension, May 1995;25(5):1069-74.
Plangger, "Effect of Torasemide on Intracranial Pressure, Mean Systemic Arterial Pressure, and Cerebral Perfusion Pressure in Experimental Brain Edema of the Rat", *Acta Neurochir Suppl* (*Wien*), 1994; 519-20; vol. 60.
Ren, et al., "Altered mRNA Expression of ATP-sensitive and Inward Rectifier Potassium Channel Subunits in Streptozotocin-Induced Diabetic Rat Heart and Aorta", *J Pharmacol Sci.* Dec. 2003;93(4):478-83.
Simard, et al., "Brain Oedema in Focal Ischaemia: Molecular Pathophysiology and Theoretical Implications," *Lancet Neurol.* Mar. 2007;6(3):258-68.
Simard, et. al., "Molecular Pathophysiology of Brain Edema in Focal Ischemia—A Focused Review" Dept. Neurosurgery Path Phys Unv MD Med, Baltimore, MD and Dept. Neuro Baylor Med and DeBakey VA Med Cnt. (Apr. 8, 2006) pp. 1-483.
Simard, J. M., et al., "Newly expressed SUR1-regulated NCca-ATP channel mediates cerebral edema after ischemic stroke", Nature Medicine (Apr. 2006) vol. 12, No. 4, pp. 433-440.
Torsemide Tablets Package Insert, pp. 1-2.
Torsemide Advanced Consumer Drug Information, pp. 1-10, http://www.drugs.com/MMX/Torsemide.html. (May 2006).
Unterberg, et al., "Edema and Brain Trauma", Neuroscience, 2004; 1021-1029; vol. 129.
White, R. P., et al., "Cerebral Arterial Contractions Induced by Human and Bovine Thrombin", Stroke, vol. 11, No. 4, Jul. 1, 1980, pp. 363-368, XP55024008, ISSN: 0039-2499.
White, R. P., et al., "Comparison of Piroxicam, Meclofenamate, Ibuprofen, Aspirin, and Prostcyclin Efficacy in a Chronic Model of Cerebral Vasospasm", Neurosurgery, Williams & Wilkens, Baltimore, MD, vol. 12, No. 1, Jan. 1, 1983, pp. 40-46, XP000614038, ISSN 0148-396X.
Yang, Shao-Hua, "17-beta Estradiol Can Reduce Secondary Ischemic Damage and Mortality of Subarachnoid Hemorrhage", Journal of Cerebral Blood FOLW and Metabolism, 2001, pp. 174-181, XP055024012.
Zhu, Q., et al., "Modulation by Nucleotides of Binding Sites for [3H]Glibenclamide in Rat Aorta and Cardiac Ventricular Membranes", J. of Cardivascular Pharm., (2001), vol. 37, pp. 522-531.

* cited by examiner

FIG. 1

THERAPEUTIC METHODS THAT TARGET THE $NC_{Ca\text{-}ATP}$ CHANNEL

CROSS-REFERENCE TO RELATED APPLICATION

This Application claims priority to U.S. Provisional Application No. 60/610,758 filed Sep. 18, 2004, and also to PCT Patent Application No. PCT/US2005/026455, filed Jul. 25, 2005, which are both incorporated herein by reference in its their entirety.

STATEMENT REGARDING FEDERALLY SPONSORED RESEARCH OR DEVELOPMENT

This invention was made in part with government support under Grant No. NS048260 awarded by the National Institutes of Health and a Merit Review grant from the United States Department of Veterans Affairs. The United States Government has certain rights in the invention.

TECHNICAL FIELD

The present invention is directed to fields of cell biology, physiology and medicine. More specifically, the present invention addresses novel methods of treating a patient comprising administering a therapeutic compound that targets a unique non-selective cation channel activated by intracellular calcium and blocked by intracellular ATP ($NC_{Ca\text{-}ATP}$ channel). In specific embodiments, the therapeutic compound is an agonist, and uses thereof in therapies, such as cancer therapies, benefiting from death of neuronal cells. In other specific embodiments, the therapeutic compound is an antagonist, and uses thereof in therapies, such as treatment of cerebral ischemia or edema, benefiting from blocking and/or inhibiting the $NC_{Ca\text{-}ATP}$ channel. Compositions comprising agonists and/or antagonists of the $NC_{Ca\text{-}ATP}$ channel are also contemplated.

BACKGROUND OF THE INVENTION

I. $NC_{Ca\text{-}ATP}$ Channel

A unique non-selective monovalent cationic ATP-sensitive channel ($NC_{Ca\text{-}ATP}$ channel) was identified first in native reactive astrocytes (NRAs) and later, as described herein, in neurons and capillary endothelial cells after stroke or traumatic brain injury (See, International application WO 03/079987 to Simard et al., and Chen and Simard, 2001, each incorporated by reference herein in its entirety). The $NC_{CaATP}$ channel is thought to be a heteromultimer structure comprised of sulfonylurea receptor type 1 (SUR1) regulatory subunits and pore-forming subunits, similar to the $K_{ATP}$ channel in pancreatic β cells (Chen et al., 2003). The pore-forming subunits of the $NC_{Ca\text{-}ATP}$ channel remain uncharacterized.

SUR imparts sensitivity to antidiabetic sulfonylureas such as glibenclamide and tolbutamide, and is responsible for activation by a chemically diverse group of agents termed "$K^+$ channel openers" such as diazoxide, pinacidil and cromakalin (Aguilar-Bryan et al., 1995; Inagaki et al., 1996; Isomoto et al., 1996; Nichols et al., 1996; Shyng et al., 1997). In various tissues, molecularly distinct SURs are coupled to distinct pore-forming subunits to form different $K_{ATP}$ channels with distinguishable physiological and pharmacological characteristics. The $K_{ATP}$ channel in pancreatic β cells is formed from SUR1 linked with Kir6.2, whereas the cardiac and smooth muscle $K_{ATP}$ channels are formed from SUR2A and SUR2B linked with Kir6.2 and Kir6.1, respectively (Fujita et al., 2000). Despite being made up of distinctly different pore-forming subunits, the $NC_{Ca\text{-}ATP}$ channel is also sensitive to sulfonylurea compounds.

Also, unlike the $K_{ATP}$ channel, the $NC_{Ca\text{-}ATP}$ channel conducts sodium ions, potassium ions, cesium ions and other monovalent cations with near equal facility (Chen and Simard, 2001) suggesting further that the characterization, and consequently the affinity to certain compounds, of the $NC_{Ca\text{-}ATP}$ channel differs from the $K_{ATP}$ channel.

Other nonselective cation channels that are activated by intracellular $Ca^{2+}$ and inhibited by intracellular ATP have been identified but not in astrocytes. Further, the $NC_{Ca\text{-}ATP}$ channel expressed and found in astrocytes differs physiologically from the other channels with respect to calcium sensitivity and adenine nucleotide sensitivity (Chen et al., 2001).

II. Gliotic Capsule

The gliotic capsule that forms around a "foreign body" in the brain is an important, albeit neglected, biological system. On the one hand, the gliotic capsule represents the response of the brain to an injurious stimulus—an attempt by the brain to wall off, isolate, dispose of, and otherwise protect itself from the foreign body. On the other hand, the gliotic capsule forms a potentially harmful mass of tissue from which originates edema fluid that contributes to brain swelling, and whose constituent cells undergo cytotoxic edema, which adds further to brain swelling. Also, the gliotic capsule protects foreign cells from immunologic surveillance.

The essential elements involved in formation of a gliotic capsule appear to be uniform in many types of CNS pathology, be it a traumatically implanted foreign body, a metastatic tumor, a brain abscess, or infarcted necrotic tissue following a stroke. First, microglia and astrocytes become activated near the site of injury, with large, stellate-shaped GFAP-positive reactive astrocytes forming the most prominent cellular component of the response. Secondly, the foreign nature of the entity is recognized, and the response is initiated to surround and contain it. Although the concept of "foreign body" encompasses a large variety of pathological conditions, the responses in most cases bear a great deal of similarity to one another.

The interface between the foreign body and the gliotic capsule, referred to as the inner zone of the gliotic capsule, appears to be of great importance in determining the overall response to injury.

Despite the overall benefits, the gliotic capsule forms a potentially harmful mass of tissue that contributes to brain swelling and mass effect, and that may shelter foreign cells from surveillance by the immune system. Applicants are the first to determine that, in a variety pathological conditions in both rats and humans, reactive astrocytes (R1 astrocytes) in the inner zone of the gliotic capsule express a novel SUR1-regulated cation channel, the $NC_{Ca\text{-}ATP}$ channel, and that this channel directly controls cell viability: opening the channel is associated with necrotic cell death and closing the channel is associated with protection from cell death induced by energy (ATP) depletion.

III. Cancer

Brain metastasis is an important cause of morbidity and mortality in cancer patients. Because most of these patients die of systemic disease, the primary therapeutic goal is often simply to improve the quality of life. Conventional therapy for brain metastases is usually whole-brain irradiation. Chemotherapy may result in regression of brain metastases in chemosensitive tumors, but overall, results of adjunctive therapy including chemotherapy and immunotherapy are disappointing.

The most widely recognized "barrier" that isolates brain metastases is the blood-brain barrier (BBB). In addition, the gliotic capsule that forms around the metastasis forms a "tumor-brain barrier" (TBB) that also isolates and protects a metastatic tumor. Unlike primary CNS-derived tumors such as glioblastoma, metastatic cancers of the brain induce a significant astrocytic reaction, resulting in formation of a gliotic capsule. The gliotic capsule that forms around a metastatic tumor represents the response of the brain to an injurious stimulus—an attempt by the brain to wall off, isolate, dispose of, and otherwise protect itself from the metastatic tumor. Importantly, however, the gliotic capsule also functions as a barrier that protects the metastatic tumor from immunologic surveillance and therapeutic targeting.

Successful immunotherapy and chemotherapy for metastatic brain tumors remains elusive. In general, the difficulty in treating these tumors is ascribed to presence of the blood brain barrier (BBB), which is believed to prevent access of chemotherapeutic agents and immunological cells to tumors located in the brain. However, much of the blood supply to metastatic tumors in the brain originates from vessels and capillaries located in the gliotic capsule that surrounds the tumor, and these capillaries, unlike those in brain per se, are fenestrated. The gliotic capsule itself that surrounds the tumor has an inner zone that is populated by R1 astrocytes that express tight junction proteins and this inner zone is thought to form a barrier between tumor and brain. The barrier formed by R1 astrocytes is termed the tumor-brain barrier (TBB).

Monotherapies with chemotherapeutic agents tends not to be very effective because conventional chemotherapeutic agents tend not to reach portions of the CNS in effective amounts, primarily because of the blood-brain barrier (BBB). For example, etoposide and actinomycin D, two commonly used oncology agents that inhibit topoisomerase II, fail to cross the blood-brain barrier in useful amounts.

As described herein, Applicants are the first to determine that the inner zone of the gliotic capsule is populated by R1 astrocytes expressing the $NC_{Ca-ATP}$ channel, and selectively killing the astrocytes expressing the $NC_{Ca-ATP}$ channel disrupts the TBB, causing migration of leukocytes across the TBB.

Other and further objects, features, and advantages will be apparent from the following description of the presently preferred embodiments of the invention, which are given for the purpose of disclosure.

BRIEF SUMMARY OF THE INVENTION

The present invention relates to a unique non-selective cation channel activated by intracellular calcium and blocked by intracellular ATP ($NC_{Ca-ATP}$ channel) that can be expressed in neuronal cells, neuroglia cells (e.g., astrocyte, ependymal cell, oligodentrocyte and microglia) or neural endothelial cells (e.g., capillary endothelial cells) in which the cells have been or are exposed to a traumatic insult, for example, an acute neuronal insult (e.g., hypoxia, ischemia, cerebral edema or cell swelling), toxic compounds or metabolites, an acute injury, cancer, brain abscess, etc. More particularly, the present invention relates to the regulation and/or modulation of this $NC_{Ca-ATP}$ channel and how its modulation can be used to treat various diseases and/or conditions, for example hyperproliferative diseases and acute neuronal insults (e.g., stroke, an ischemic/hypoxic insult). Yet further, the present invention relates to the regulation and/or modulation of this $NC_{Ca-ATP}$ channel and its role in maintaining or disrupting the integrity of the gliotic capsule. The modulation and/or regulation of the channel results from administration of an activator or agonist of the channel or an antagonist or inhibitor of the channel. Thus, depending upon the disease, a composition (an antagonist or inhibitor) is administered to block or inhibit the channel to prevent cell death, for example to treat cerebral edema that results from ischemia due to tissue trauma or to increased tissue pressure. In these instances the channel is blocked to prevent or reduce or modulate depolarization of the cells. In the case of cancer or other hyperproliferative diseases, it is desirable to open or activate the channel by administering an agonist or activator compound to cause cell depolarization resulting in cell death of the cancer cells or hyperproliferative cells.

The composition(s) of the present invention may be delivered alimentary or parenterally. Examples of alimentary administration include, but are not limited to orally, buccally, rectally, or sublingually. Parenteral administration can include, but are not limited to intramuscularly, subcutaneously, intraperitoneally, intravenously, intratumorally, intraarterially, intraventricularly, intracavity, intravesical, intrathecal, or intrapleural. Other modes of administration may also include topically, mucosally, transdermally, direct injection into the brain parenchyma.

An effective amount of an agonist or antagonist of $NC_{Ca-ATP}$ channel that may be administered to a cell includes a dose of about 0.0001 nM to about 200 μM. More specifically, doses of an agonist to be administered are from about 0.01 nM to about 200 μM; about 0.01 μM to about 0.05 μM; about 0.05 μM to about 1.0 μM; about 1.0 μM to about 1.5 μM; about 1.5 μM to about 2.0 μM; about 2.0 μM to about 3.0 μM; about 3.0 μM to about 4.0 μM; about 4.0 μM to about 5.0 μM; about 5.0 μM to about 10 μM; about 10 μM to about 50 μM; about 50 μM to about 100 μM; about 100 μM to about 200 μM; about 200 μM to about 300 μM; about 300 μM to about 500 μM; about 500 μM to about 1000 μM; about 1000 μM to about 1500 μM and about 1500 μM to about 2000 μM. Of course, all of these amounts are exemplary, and any amount in-between these points is also expected to be of use in the invention.

An effective amount of an agonist and/or antagonist of the $NC_{Ca-ATP}$ channel or related-compounds thereof as a treatment varies depending upon the host treated and the particular mode of administration. In one embodiment of the invention the dose range of the agonist and/or antagonist of the $NC_{Ca-ATP}$ channel or related-compounds thereof will be about 0.01 μg/kg body weight to about 20,000 μg/kg body weight. The term "body weight" is applicable when an animal is being treated. When isolated cells are being treated, "body weight" as used herein should read to mean "total cell body weight". The term "total body weight" may be used to apply to both isolated cell and animal treatment. All concentrations and treatment levels are expressed as "body weight" or simply "kg" in this application are also considered to cover the analogous "total cell body weight" and "total body weight" concentrations. However, those of skill will recognize the utility of a variety of dosage range, for example, 0.01 μg/kg body weight to 20,000 μg/kg body weight, 0.02 μg/kg body weight to 15,000 μg/kg body weight, 0.03 μg/kg body weight to 10,000 μg/kg body weight, 0.04 μg/kg body weight to 5,000 μg/kg body weight, 0.05 μg/kg body weight to 2,500 μg/kg body weight, 0.06 μg/kg body weight to 1,000 μg/kg body weight, 0.07 μg/kg body weight to 500 μg/kg body weight, 0.08 μg/kg body weight to 400 μg/kg body weight, 0.09 μg/kg body weight to 200 μg/kg body weight or 0.1 μg/kg body weight to 100 μg/kg body weight. Further, those of skill will recognize that a variety of different dosage levels will be of use, for example, 0.0001 μg/kg, 0.0002 μg/kg, 0.0003 μg/kg, 0.0004 μg/kg, 0.005 μg/kg, 0.0007 μg/kg, 0.001 μg/kg, 0.1 μg/kg, 1.0 μg/kg, 1.5 μg kg, 2.0 μg/kg, 5.0 μg/kg, 10.0 μg/kg, 15.0 μg/kg, 30.0 μg/kg, 50 μg/kg, 75 μg/kg, 80 μg/kg, 90 μg/kg, 100 μg/kg, 120 μg/kg, 140 μg/kg, 150 μg/kg, 160 μg/kg, 180 μg/kg, 200 μg/kg, 225 μg/kg, 250 μg/kg, 275 g/kg, 300 μg/kg, 325 μg/kg, 350 μg/kg, 375 μg/kg, 400 μkg, 450 μg/kg, 500 μg/kg, 550 μg/kg, 600 μg/kg, 700 μg/kg, 750 μg/kg, 800 μg/kg, 900 μg/kg, 1 mg/kg, 5 mg/kg, 10 mg/kg, 12 mg/kg, 15 mg/kg, 20 mg/kg, and/or 30 mg/kg. Of course, all of these dosages are exemplary, and any dosage in-between these points is also expected to be of use in the invention. Any of the above dosage ranges or dosage levels may be employed for an agonist and/or antagonist of $NC_{Ca-ATP}$ channel or related-compounds thereof.

The $NC_{Ca-ATP}$ channel is blocked by antagonists of type 1 sulfonylurea receptor (SUR1) and opened by SUR1 activators. More specifically, the antagonists of type 1 sulfonylurea receptor (SUR1) include blockers of $K_{ATP}$ channels and the SUR1 activators include activators of $K_{ATP}$ channels. More specifically, the $NC_{Ca-ATP}$ channel of the present invention has a single-channel conductance to potassium ion ($K^+$) between 20 and 50 pS. The $NC_{Ca-ATP}$ channel is also stimulated by $Ca^{2+}$ on the cytoplasmic side of the cell membrane in a physiological concentration range, where concentration range is from $10^{-8}$ to $10^{-5}$ M. The $NC_{Ca-ATP}$ channel is also inhibited by cytoplasmic ATP in a physiological concentration range, where the concentration range is from $10^{-1}$ to 10 M. The $NC_{Ca-ATP}$ channel is also permeable to the following cations; $K^+$, $Cs^+$, $Li^+$, $Na^+$; to the extent that the permeability ratio between any two of the cations is greater than 0.5 and less than 2.

Certain embodiments of the present invention comprise a method of treating a hyperproliferative disease by administering to a subject an amount of a compound effective to activate a $NC_{Ca-ATP}$ channel in a neuronal cell or a neuroglia cell or a neural endothelial cell or a combination thereof. The activation of the channel results in an influx of sodium ions ($Na^+$) causing depolarization of the cell. The influx of $Na^+$ alters the osmotic gradient causing an influx of water into the cell which leads to cytotoxic edema ultimately resulting in necrotic cell death.

The hyperproliferative disease is a tumor, for example, a benign or malignant tumor, More specifically, the tumor is a neuroma or glioma. Still further, the tumor can originate from a primary brain tumor or metastatic brain tumor. Gliomas can include, but are not limited to astocytoma, brain stem glioma, ependynmomas, optic nerve glioma, and oligodendroglioma. The tumor may also be gliobastoma, medulloblastoma, papilloma of choroid plexus, metastases, meningioma, pituitary adenoma, Schwannoma, lymphoma, congenital tumors, neurosarcoma, neurofibromatosis, neuroblastoma, craniopharyngioma, pineal region tumors or primitive neuroectodermal tumors.

The activator compound or agonist can be a type 1 sulfonylurea receptor agonist. For example, agonists that can be used in the present invention include, but are not limited to agonist of SUR1, for example, diazoxide, pinacidil, P1075, and cromakalin. Other agonists can include, but are not limited to diazoxide derivatives, for example 3-isopropylamino-7-methoxy-4H-1,2,4-benbzothiadiazine 1,1-dioxide (NNC 55-9216), 6,7-dichloro-3-isopropylamino-4H-1,2,4-benzothiadiazine 1,1-dioxide (BPDZ 154), 7-chloro-3-isopropylamino-4H-1,2,4-benzothiadiazine 1,1-dioxide (BPDZ 73), 6-Chloro-3-isopropylamino-4H-thieno[3,2-e]-1,2,4-thiadiazine 1,1-dioxide (NNC 55-0118)4, 6-chloro-3-(1-methylcyclopropyl)amino-4H-thieno[3,2-e]-1,2,4-thiadiazine 1,1-dioxide (NN414), 3-(3-methyl-2-butylamino)-4H-pyrido[4,3-e]-1,2,4-thiadiazine 1,1-dioxide (BPDZ 44), 3-(1',2',2'-trimethylpropyl)amino-4H-pyrido(4,3-e)-1,2,4-thiadiazine 1,1-dioxide (BPDZ 62), 3-(1',2',2'-trimethylpropyl)amine-4H-pyrido (2,3-e)-1,2,4-thiadiazine, 1,1-dioxide (BPDZ 79), 2-alkyl-3-alkylamino-2H-benzo- and 2-alkyl-3-alkylamino-2H-pyrido[4,3-e]-1,2,4-thiadiazine 1,1-dioxides, 6-Chloro-3-alkylamino-4H-thieno[3,2-e]-1,2,4-thiadiazine 1,1-dioxide derivatives, 4-N-Substituted and -unsubstituted 3-alkyl- and 3-(alkylamino)-4H-pyrido[4,3-e]-1,2,4-thiadiazine 1,1-dioxides. In addition, other compounds, including 6-chloro-2-methylquinolin-4(1H)-one (HEI 713) and LN 533021, as well as the class of drugs, arylcyanoguanidines, are known activators or agonist of SUR1. Other compounds that can be used include compounds known to activate $K_{ATP}$ channels.

In further embodiments, the method comprises administering to the subject an anti-cancer therapy in combination with the activator compound that activates or stimulates or opens the $NC_{Ca-ATP}$ channel. The anti-cancer or anti-tumor therapy is chemotherapy, radiotherapy, immunotherapy, surgery or a combination thereof.

Another embodiment of the present invention comprises a method of disrupting the integrity of the tumor-brain barrier surrounding a tumor in the brain of a subject comprising administering to the subject a compound effective to activate a $NC_{Ca-ATP}$ channel in a neuronal cell, or a neuroglia cell, a neural endothelial cell or a combination thereof. This method can further comprise administering to the subject an anti-cancer therapy, wherein the anti-cancer or anti-tumor therapy is chemotherapy, radiotherapy, immunotherapy, surgery or a combination thereof.

Still further, another embodiment of the present invention comprises a method of inducing cell death of a neuronal or a neurolgia cell or a neural endothelial cell comprising administering to the cell a compound effective to activate a $NC_{Ca-ATP}$ channel in the cell. Activation of the $NC_{Ca-ATP}$ channel results in an influx of sodium ions ($Na^+$) causing depolarization of the cell. The influx of $Na^+$ alters the osmotic gradient causing an influx of water into the cell which leads to cytotoxic edema ultimately resulting in necrotic cell death.

Yet further, another embodiment of the present invention comprises a pharmaceutical composition comprising a thrombolytic agent (e.g., tissue plasminogen activator (tPA), urokinase, prourokinase, streptokinase, anistreplase, reteplase, tenecteplase), an anticoagulant or antiplatelet (e.g., aspirin, warfarin or coumadin), statins, diuretics, vasodilators, mannitol, diazoixde or similar compounds that stimulates or promotes ischemic precondition or a pharmaceutically acceptable salt thereof and a compound that inhibits a $NC_{Ca-ATP}$ channel or a pharmaceutically acceptable salt thereof. This pharmaceutical composition can be considered neuroprotective. For example, the pharmaceutical composition comprising a combination of the thrombolytic agent and a compound that inhibits a $NC_{Ca-ATP}$ channel is neuroprotective because it increases the therapeutic window of for the administration of the thrombolytic agent by several hours, for example the therapeutic window for administration of thrombolytic agents may be increased by several hours (4-8 hrs) by co-administering antagonist of the $NC_{Ca\text{-}ATP}$ channel.

The channel can be inhibited by an $NC_{Ca\text{-}ATP}$ channel inhibitor, an $NC_{CaATP}$ channel blocker, a type 1 sulfonylurea receptor (SUR1) antagonist, SUR1 inhibitor, or a compound capable of reducing the magnitude of membrane current through the channel. More specifically, the SUR1 antagonist is selected from the group consisting of glibenclamide, tolbutamide, repaglinide, nateglinide, meglitinide, midaglizole, LY397364, LY389382, glyclazide, glimepiride, estrogen, estrogen-related compounds (estradiol, estrone, estriol, genistein, non-steroidal estrogen (e.g., diethystilbestrol), phytoestrogen (e.g., coumestrol), zearalenone, etc.), and compounds known to inhibit or block $K_{ATP}$ channels. MgADP can also be used to inhibit the channel. Other compounds that can be used to block or inhibit $K_{ATP}$ channels include, but are not limited to tolbutamide, glyburide (1[p-2[5-chloro-O-anisamido)ethyl] phenyl] sulfonyl]-3-cyclohexyl-3-urea); chlopropamide (1-[[(p-chlorophenyl)sulfonyl]-3-propylurea; glipizide (1-cyclohexyl-3 [[p-[2(5-methylpyrazine carboxamido)ethyl] phenyl] sulfonyl] urea); or tolazamide(benzenesulfonamide-N-[[(hexahydro-1H-azepin-1yl)amino] carbonyl]-4-methyl).

Another embodiment of the present invention comprises a composition comprising a membrane preparation derived from a neural endothelial cell expressing a $NC_{Ca\text{-}ATP}$ channel, wherein channel is blocked by antagonists of type 1 sulfonylurea receptor (SUR1) and opened by SUR1 activators. More specifically, the channel has the following characteristics: (a) it is a 35 pS type channel; (b) it is stimulated by cytoplasmic $Ca^{2+}$ in the concentration range from about $10^{-8}$ to about $10^{-5}$ M; (c) it opens when cytoplasmic ATP is less than about 0.8 μM; and (d) it is permeable to the monovalent cations $K^+$, $Cs^+$, $Li^+$ and $Na^+$.

In further embodiments, the compound that inhibits the $NC_{Ca\text{-}ATP}$ channel can be administered in combination with a thrombolytic agent (e.g., tissue plasminogen activator (tPA), urokinase, prourokinase, streptokinase, anistreplase, reteplase, tenecteplase), an anticoagulant or antiplatelet (e.g., aspirin, warfarin or coumadin), statins, diuretics, vasodilators (e.g., nitroglycerin), mannitol, diazoixde or similar compounds that stimulates or promotes ischemic preconditition.

Still further, another embodiment comprises a method of treating an acute cerebral ischemia in a subject comprising administering to a subject an amount of a thrombolytic agent or a pharmaceutically acceptable salt thereof in combination with an amount of a compound that inhibits a $NC_{Ca\text{-}ATP}$ channel or a pharmaceutically acceptable salt thereof. In certain embodiments, the thrombolytic agent is a tissue plasminogen activator (tPA), urokinase, prourokinase, streptokinase, anistreplase, reteplase, tenecteplase or any combination thereof. The SUR1 antagonist can be administered by any standard parenteral or alimentary route, for example the SUR1 antagonist may be administered as a bolus injection or as an infusion or a combination thereof.

The channel is expressed on neuronal cells, neuroglia cells, neural epithelial cells or a combination thereof. The inhibitor blocks the influx of $Na^+$ into the cells thereby preventing depolarization of the cells. Inhibition of the influx of $Na^+$ into the cells thereby prevents cytotoxic edema and reduces hemorrhagic conversion. Thus, this treatment reduces cell death or necrotic death of neuronal and/or neural endothelial cells.

In certain embodiments, the amount of the SUR1 antagonist administered to the subject is in the range of about 0.0001 μg/kg/day to about 20 mg/kg/day, about 0.01 μg/kg/day to about 100 μg/kg/day, or about 100 μg/kg/day to about 20 mg/kg/day. Still further, the SUR1 antagonist may be administered to the subject in the from of a treatment in which the treatment may comprise the amount of the SUR1 antagonist or the dose of the SUR1 antagonist that is administered per day (1, 2, 3, 4, etc.), week (1, 2, 3, 4, 5, etc.), month (1, 2, 3, 4, 5, etc.), etc. Treatments may be administered such that the amount of SUR1 antagonist administered to the subject is in the range of about 0.0001 μg/kg/treatment to about 20 mg/kg/treatment, about 0.01 μg/kg/treatment to about 100 μg/kg/treatment, or about 100 μg/kg/treatment to about 20 mg/kg/treatment.

Another embodiment of the present invention comprises a method of reducing mortality of a subject suffering from a stroke comprising administering to the subject a compound effective to inhibit a $NC_{Ca\text{-}ATP}$ channel in a neuronal cell, a neuroglia cell, a neural endothelial cell or a combination thereof. The compound reduces stroke size and reduces edema located in the peri-infarct tissue. The compound can be administered alimentary (e.g., orally, buccally, rectally or sublingually) or parenterally (e.g., intravenously, intradermally, intramuscularly, intraarterially, intrathecally, subcutaneously, intraperitoneally, intraventricularly) and/or topically (e.g., transdermally), mucosally, or by direct injection into the brain parenchyma.

Still further, another embodiment comprises a method of reducing edema in a peri-infarct tissue area of a subject comprising administering to the subject a compound effective to inhibit a $NC_{Ca\text{-}ATP}$ channel in a neuronal cell, a neuroglia cell, an endothelium cell or a combination thereof.

Further embodiments comprises a method of treating a subject at risk for developing a stroke comprising administering to the subject a compound effective to inhibit a $NC_{Ca\text{-}ATP}$ channel in neuronal cell, a neuroglia cell, a neural endothelial cell or a combination thereof.

In certain embodiments, the subject is undergoing treatment for a cardiac condition, thus the condition increases the subjects risk for developing a stroke. The treatment, for example, may comprise the use of thrombolytic agents to treat myocardial infarctions. Still further, the subject may be at risk for developing a stroke because the subject suffers from atrial fibrillation or a clotting disorder. Other subjects that are at risk for developing a stroke include subjects that are at risk of developing pulmonary emboli, subjects undergoing surgery (e.g., vascular surgery or neurological surgery), or subjects undergoing treatments that increase their risk for developing a stroke, for example, the treatment may comprise cerebral/endovascular treatment, angiography or stent placement.

Another embodiment of the present invention comprises a method of treating a subject at risk for developing cerebral edema comprising administering to the subject a compound effective to inhibit a $NC_{Ca\text{-}ATP}$ channel in a neuronal cell, a neuroglia cell, a neural endothelial cell or a combination thereof. The subject at risk may be suffering from an arterior-venous malformation, or a mass-occupying lesion (e.g., hematoma) or may be involved in activities that have an increased risk of brain trauma.

Yet further, another embodiment of the present invention comprises a method of maintaining the integrity of the gliotic capsule surrounding brain abscess of a subject comprising administering to the subject a compound effective to inhibit and/or block a $NC_{Ca\text{-}ATP}$ channel in a neuronal cell, or a neuroglia cell, a neural endothelial cell or a combination thereof.

Still further, another method of the present invention comprises a method of diagnosing neuronal cell edema and/or cytotoxic damage in the brain comprising: labeling an antagonist of SUR1; administering the labeled antagonist of SUR1 to a subject; measuring the levels of labeled antagonist of SUR1 in the brain of the subject, wherein the presence of labeled antagonist of SUR1 indicates neuronal cell edema and/or cytotoxic damage in the brain.

Another method of the present invention comprise determining the boundaries of a brain tumor comprising: labeling an antagonist of SUR1; administering the labeled antagonist of SUR1 to a subject; visualizing the labeled antagonist of SUR1 in the brain of the subject, wherein the presence of labeled antagonist of SUR1 indicates the boundaries of the brain tumor, for example, a metastatic tumor. In certain embodiments, the step of visualizing is performed using by using positron emission topography (PET) scans.

In further embodiments, the methods can comprise a method of determining the penumbra following a stroke comprising: labeling an antagonist of SUR1; administering the labeled antagonist of SUR1 to a subject; visualizing the labeled antagonist of SUR1 in the brain of the subject, wherein the presence of labeled antagonist of SUR1 indicates the penumbra.

Yet further, the present invention comprises a method monitoring stroke neural disease comprising: labeling an antagonist of SUR1; administering the labeled antagonist of SUR1 to a subject; visualizing the labeled antagonist of SUR1 in the brain of the subject, wherein the presence of labeled antagonist of SUR1 indicates the progression of the disease. In certain embodiments, the step is visualizing is performed daily to monitor the progression of the stroke.

Another embodiment comprises a neuroprotective infusion kit comprising a compound that inhibits a $NC_{Ca\text{-}ATP}$ channel in a neuronal cell, a neuroglia cell, a neural endothelial cell or a combination thereof and an IV solution. The compound and solution are contained within the same container or within different containers. More specifically, the compound is contained within the container of solution.

The kit may further comprise a neuroprotective bolus kit, wherein the bolus kit comprises a pre-loaded syringe of a compound inhibits a $NC_{Ca\text{-}ATP}$ channel in a neuronal cell, a neuroglia cell, a neural endothelial cell or a combination thereof.

Still further, another embodiment comprises a neuroprotective kit comprising a compound that inhibits $NC_{Ca\text{-}ATP}$ channel in a neuronal cell, a neuroglia cell, an endothelium cell or a combination thereof and a thrombolytic agent (e.g., tPA), an anticoagulant (e.g., warfarin or coumadin), an antiplatelet (e.g., aspirin), a diuretic (e.g., mannitol), a statin, or a vasodilator (e.g., nitroglycerin).

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 1 shows that addition of exogenous phosphatidylinositol-4,5-bisphosphate ($PIP_2$) causes activation of the $NC_{CaATP}$ channel, despite the presence of ATP in the bath solution. Initially, channel activity was recorded in an inside-out patch of membrane from an R1 astrocyte, with a bath solution containing 1 μM $Ca^{2+}$ and 10 μM ATP, which was sufficient to block channel activity. Addition of 50 μM $PIP_2$ resulted in channel activation, reflecting an apparent decrease in affinity of the channel for ATP.

FIG. 3A was developed using antibodies directed against estrogen receptors (ER), demonstrating that both ERα and ERβ are expressed in astrocytes from both genders. Western blots showed that SUR1 is also expressed by cells from both genders, with pancreatic tissue used as control (FIG. 3B).

FIG. 5A shows a coronal section of a rat brain sectioned though the site of implantation of a large gelatin sponge; the sponge (innermost dark region) is encapsulated by a gliotic capsule (light area), outside of which is found a region of vasogenic edema (outer dark area), identified by pre-mortem administration of methylene blue. FIGS. 5B and 5C show low power and high power views, respectively, of the gliotic capsule immunolabeled for GFAP. FIG. 5D shows a high power view of GFAP-labeled cells inside of the gelatin sponge implant.

FIGS. 6A, 6C, 6E show freshly-isolated large phase-bright R1 astrocytes immunolabeled for GFAP (FIG. 6C) and vimentin (FIG. 6E). FIG. 6B,D,F show freshly-isolated small phase-dark R2 astrocytes immunolabeled for GFAP (FIG. 6D) and vimentin (FIG. 6F). FIG. 6G shows primary cultures of astrocytes isolated from a gliotic capsule, with R1 astrocytes developing into large polygonal cells (FIG. 6Gb), and R2 astrocytes developing into small bipolar cells (FIG. 6Ga). FIG. 6H shows that R2 astrocytes, but not R1 astrocytes, are labeled with fluorescein tagged chlorotoxin derived from the scorpion, *Leiurus quinquestriatus*.

FIG. 7D shown RT-PCR for SUR1 in control insulinoma cells (lane 2) and in isolated R1 astrocytes (lane 3), and for SUR2 in control cardiac cells (lane 4), but not in isolated R1 astrocytes (lane 5).

FIGS. 8G-I show that pimonidazole, HIF1α and occludens all localize to GFAP-positive astrocytes that form the inner zone of the gliotic capsule.

FIGS. 9A-B show effects of $NC_{Ca\text{-}ATP}$ channel inhibition (FIG. 9A) and $NC_{Ca\text{-}ATP}$ channel activation (FIG. 9B) on the gliotic capsule. Animals with gelatin sponge implants were treated with glibenclamide infusion (FIG. 9A) or diazoxide infusion (FIG. 9B) via osmotic mini-pumps that delivered the compounds directly into the area of the gelatin sponge. Immunolabeling for GFAP showed that channel inhibition with glibenclamide resulted in formation of a well defined gliotic capsule (FIG. 9A), whereas channel activation with diazoxide resulted in formation of a broader, ill-defined capsule (FIG. 9B), due to diazoxide-induced necrotic death of inner zone cells.

FIG. 13A shows phase contrast images of 4 different freshly isolated R1 astrocytes observed over the course of 30 min each. The cell exposed to vehicle solution alone remained phase bright with no pathological deterioration (control). The cell depleted of ATP by exposure to Na azide (1 mM) developed progressive blebbing consistent with cytotoxic edema. Similarly, the cell exposed to the $NC_{Ca\text{-}ATP}$ channel opener, diazoxide, developed progressive blebbing consistent with cytotoxic edema. The cell exposed to Na azide in the presence of glibenclamide remained phase bright with no pathological deterioration. FIGS. 13B and 13C show cell death of isolated R1 astrocytes induced by ATP depletion in vitro. Freshly isolated R1 astrocytes were labeled for necrotic death with propidium iodide (PI) (FIG. 13B), or for apoptotic death with annexin V (FIG. 13C), under control conditions, after exposure to Na azide (1 mM), or after exposure to Na azide in the presence of glibenclamide (1 μM). Exposure to Na azide resulted mostly in necrotic death that was largely prevented by glibenclamide.

FIG. 16A shows phase-contrast image of large neuron-like cells enzymatically isolated from ischemic region 3 hr following MCAO. FIG. 16B shows recording of inside-out patch using $Cs^+$ as the charge carrier; channel activity was blocked by glibenclamide given as indicated (arrow); a and b show expanded records of the portions indicated. FIG. 16C shows recordings at potentials indicated of inside-out patch using $K^+$ as the charge carrier; channel activity was blocked by glibenclamide. FIG. 16D shows a plot of single channel amplitudes at different voltages showing single channel slope conductance of 34 pS.

In FIG. 17A, Mortality was assessed during 7 days after MCA stroke [double occlusion model with malignant cerebral edema (MCE)] in two treatment groups, each comprised of 19 female and 10 male rats, treated with either saline (empty symbols) or glibenclamide (filled symbols); mortality at 7 days was significantly different. Subgroup analyses for males and females showed similar results. In FIG. 17B edema was assessed 8 hr after MCA stroke (MCE model) in two treatment groups, each comprised of 6 male rats treated with either saline or glibenclamide; tissues were first processed with TTC to allow separation into TTC(+) and TTC(−) portions of the involved hemisphere and contralateral hemisphere, prior to determining wet/dry weights; values in TTC(+) regions were statistically different. In FIGS. 17C-17E, stroke size was assessed 48 hr after MCA stroke [thromboembolic (TE) model] in two treatment groups, each comprised of 10 male rats, treated with either saline or glibenclamide; images of TTC-stained coronal sections following MCA stroke (TE model) in an animal treated with saline (FIG. 17C) and another treated with glibenclamide (FIG. 17D), showing cortical sparing often associated with glibenclamide treatment; values of stroke size, expressed as percent of hemisphere volume (FIG. 17E).

In FIG. 18D, immunofluorescence image of a brain section from an animal 6 hr after MCA stroke (MCE model) labeled with anti-SUR1 antibody showing strong labeling in a capillary and in adjacent neuron-like cells.

FIGS. 19A-9H show that glibenclamide reduces hemorrhagic conversion. FIGS. 19A-19D are from animals co-treated with saline; FIGS. 19E-19H are from animals co-treated with glibenclamide. The left column of photographs of coronal sections shows, in rows 1-2 only, intraventricular hemorrhage, plus large areas of hemorrhagic conversion in ischemic cortical/subcortical regions (red areas on the right side of pictures; arrows). The right column of photographs of TTC-processed sections from the same animals show the areas of infarction.

FIG. 20A shows activation of MMP-9 & MMP-2 in stroke tissue compared to control; activity of recombinant MMP-9 & MMP-2 shown at left. FIG. 20B shows gelatinase activity of recombinant enzyme and stroke tissue under control conditions (CTR), in presence of glibenclamide (10 μM), and in presence of MMP inhibitor II (300 nM; Calbiochem).

FIGS. 22A and 22B show superimposed macroscopic currents recorded during 200 ms depolarizing pulses from −120 mV to +120 mV in 20 mV steps in an endothelial cell (FIG. 22A) and in an elongated smooth muscle cell (FIG. 22B); holding potential, −60 mV; nystatin perforated patch technique; bath solution, standard Krebs with 2 mM $Ca^{2+}$; pipette solution, 145 mM $K^+$. FIGS. 22C and 22D show current-voltage curves computed from average (mean±SE) currents at the end of 200-ms test pulses recorded in 9 endothelial cells (FIG. 22C) and 7 smooth muscle cells (FIG. 22D); same holding potential, technique and solutions as in FIGS. 22A and 22B. FIGS. 22E and 22F show current voltage curves recorded during ramp pulses (0.45 mV/ms, holding potential, −60 mV) in an endothelial cell (FIG. 22E) and in a smooth muscle cell (FIG. 22F); same holding potential, technique and bath solution as in FIGS. 22A and 22B, but with pipette solution containing 145 mM $Cs^+$ instead of $K^+$.

FIGS. 24A and 24B show Western blot (FIG. 24A) and quantification of Western blots (FIG. 24B) of R1 cell lysates confirmed knock down of SUR1 expression by antisense. FIGS. 24C-24E show Na azide caused large depolarizations in cells exposed to SCR-ODN (FIG. 24C, 24E) but little or no depolarization in cells exposed to AS-ODN (FIG. 24D, 24E).

FIG. 26C double labeling of large neuron-like cell showing nuclear SP1 (green) and cytoplasmic/plasmalemmal SUR1 (red) in the same cell.

FIGS. 27A and 27C show Western blot analysis of HIF1α protein in R1 astrocytes from gelfoam implant model of control (CTR) and HIF1α knock-down (KD). FIGS. 27B and 27C show SUR1 protein in the same cell lysates.

DETAILED DESCRIPTION OF THE INVENTION

Figure 2:
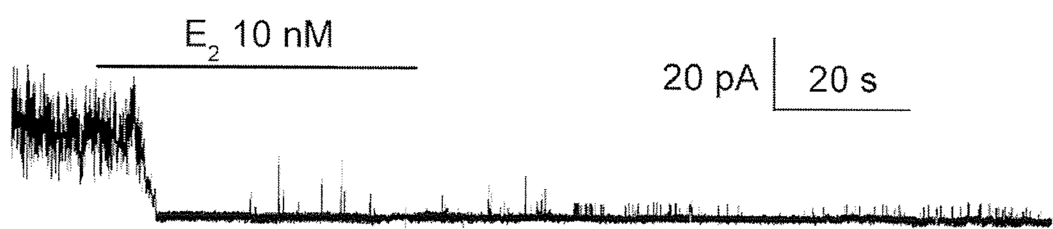
FIG. 2 shows that the $NC_{Ca\text{-}ATP}$ channel in an R1 astrocyte is inhibited by estrogen. The initial portion of the record shows brisk activity from a number of superimposed channels, recorded in a cell attached patch of membrane from an R1 astrocyte obtained from a female. Addition of 10 nM estrogen to the bath promptly resulted in strong inhibition of channel activity. The mechanism involved is believed to be related to estrogen receptor mediated activation of phospholipase C (PLC), resulting in depletion of $PIP_2$ from the membrane, and reflecting an apparent increase in affinity for ATP.

It is readily apparent to one skilled in the art that various embodiments and modifications can be made to the invention disclosed in this Application without departing from the scope and spirit of the invention.

I. Definitions

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternative are mutually exclusive, although the disclosure supports a definition that refers to only alternatives and "and/or."

As used herein, the term "acute" refers to the onset of a health effect, usually the effect is a rapid onset that is considered brief, not prolonged.

As used herein, the term "acute cerebral ischemia" refers to a cerebral ischemic event that has a rapid onset and is not prolonged. The terms "acute cerebral ischemia" and "stroke" can be used interchangeably."

As used herein, the term "anti-cancer therapy" or "anti-tumor" refers to any therapy that destroys a cancer cell and/or a tumor cell, or slows, arrests, or reverses the growth of a cancer cell and/or tumor cell. Anti-cancer or anti-tumor therapies include, without limitation, radiation therapy (radiotherapy), chemotherapy, or a combination of these therapies.

As used herein, the term "agonist" refers to a biological or chemical agent that combines with a receptor on a cell and initiates the same or equivalent reaction or activity produced by the binding of an endogenous substance. In the present invention, the agonist combines, binds, and/or associates with a $NC_{Ca-ATP}$ channel of a neuronal cell, a neuroglial cell, or a neural endothelial cell, such that the $NC_{Ca-ATP}$ channel is opened (activated). In certain embodiments, the agonist combines, binds and/or associates with a regulatory subunit of the $NC_{Ca-ATP}$ channel, particularly a SUR1. Alternatively, the agonist combines, binds, and/or associates with a pore-forming subunit of the $NC_{Ca-ATP}$ channel, such that the $NC_{Ca-ATP}$ channel is opened (activated). The terms agonist and/or activator can be used interchangeably.

As used herein, the term "antagonist" refers to a biological or chemical agent that acts within the body to reduce the physiological activity of another chemical or biological substance. In the present invention, the antagonist blocks, inhibits, reduces and/or decreases the activity of a $NC_{Ca-ATP}$ channel of a neuronal cell, a neuroglia cell or a neural endothelial cell (e.g., capillary endothelial cells). In the present invention, the antagonist combines, binds, associates with a $NC_{Ca-ATP}$ channel of neuronal cell, a neuroglia cell or a neural endothelial cell (e.g., capillary endothelial cells), such that the $NC_{Ca-ATP}$ channel is closed (deactivated), meaning reduced biological activity with respect to the biological activity in the diseased state. In certain embodiments, the antagonist combines, binds and/or associates with a regulatory subunit of the $NC_{Ca-ATP}$ channel, particularly a SUR1. Alternatively, the antagonist combines, binds, and/or associates with a pore-forming subunit of the $NC_{Ca-ATP}$ channel, such that the $NC_{Ca-ATP}$ channel is closed (deactivated). The terms antagonist or inhibitor can be used interchangeably.

As used herein, the terms "brain abscess" or "cerebral abscess" refer to a circumscribed collection of purulent exudate that is typically associated with swelling.

As used herein, the terms "blood brain barrier" or "BBB" refer the barrier between brain blood vessels and brain tissues whose effect is to restrict what may pass from the blood into the brain.

As used herein, the term "cancer" refers to a hyperproliferation of cells whose unique trait-loss of normal controls-results in unregulated growth, lack of differentiation, local tissue invasion, and metastasis. Cancer may include a tumor comprised of tumor cells. Those of skill in the art understand that not all cancers comprise tumor cells, for example leukemia does not comprise tumor cells.

As used herein, the term "cerebral ischemia" refers to a lack of adequate blood flow to an area, for example a lack of adequate blood flow to the brain, which may be the result of a blood clot, blood vessel constriction, a hemorrhage or tissue compression from an expanding mass.

As used herein, the term "depolarization" refers to an increase in the permeability of the cell membrane to sodium ions wherein the electrical potential difference across the cell membrane is reduced or eliminated.

As used herein, the terms "effective amount" or "therapeutically effective amount" are interchangeable and refer to an amount that results in an improvement or remediation of the symptoms of the disease or condition. Those of skill in the art understand that the effective amount may improve the patient's or subject's condition, but may not be a complete cure of the disease and/or condition.

As used herein, the term "endothelium" refers a layer of cells that line the inside surfaces of body cavities, blood vessels, and lymph vessels or that form capillaries.

As used herein, the term "endothelial cell" refers to a cell of the endothelium or a cell that lines the surfaces of body cavities, for example, blood or lymph vessels or capillaries. In certain embodiments, the term endothelial cell refers to a neural endothelial cell or an endothelial cell that is part of the nervous system, for example the central nervous system or the brain.

As used herein, the term "hyperproliferative disease" refers to a disease that results from a hyperproliferation of cells. Exemplary hyperproliferative diseases include, but are not limited to cancer, tumors or neoplasms.

As used herein, the term "gliotic capsule" refers to a physical barrier surrounding, in whole or in part, a foreign body, including a metastatic tumor, a cerebral abscess or other mass not normally found in brain except under pathological conditions. In certain embodiments, the gliotic capsule comprises an inner zone comprising neuronal cells, neuroglial cells (e.g., astrocytes) and/or endothelial cells expressing a $NC_{Ca-ATP}$ channel.

The term "morbidity" as used herein is the state of being diseased. Yet further, morbidity can also refer to the disease rate or the ratio of sick subjects or cases of disease in to a given population.

The term "mortality" as used herein is the state of being mortal or causing death. Yet further, mortality can also refer to the death rate or the ratio of number of deaths to a given population.

As used herein, the term "neuronal cell" refers to a cell that is a morphologic and functional unit of the nervous system. The cell comprises a nerve cell body, the dendrites, and the axon. The terms neuron, nerve cell, neuronal, neurone, and neurocyte can be used interchangeably. Neuronal cell types can include, but are not limited to a typical nerve cell body showing internal structure, a horizontal cell (of Cajal) from cerebral cortex; Martinottic cell, biopolar cell, unipolar cell, Pukinje cell, and a pyramidal cell of motor area of cerebral cortex.

As used herein, the term "neural" refers to anything associated with the nervous system.

As used herein, the terms "neuroglia" or "neuroglial cell" refers to a cell that is a non-neuronal cellular element of the nervous system. The terms neuroglia, neurogliacyte, and neuroglial cell can be used interchangeably. Neuroglial cells can include, but are not limited to ependymal cells, astrocytes, oligodendrocytes, or microglia.

The term "preventing" as used herein refers to minimizing, reducing or suppressing the risk of developing a disease state or parameters relating to the disease state or progression or other abnormal or deleterious conditions.

As used herein, the term "stroke" refers to any acute, clinical event related to the impairment of cerebral circulation. The terms "acute cerebral ischemia" and "stroke" can be used interchangeably."

As used herein, the term "tumor" refers to any swelling tumefaction. Tumor is interchangeable with the term "neoplasm" which is abnormal tissue growth. Tumors can be malignant or benign.

As used herein, the term "tumor-brain barrier" refers to a biochemical barrier between a foreign body in the brain and the surrounding tissue of the brain. The tumor-brain barrier is interchangeably referred to herein as TBB.

The terms "treating" and "treatment" as used herein refer to administering to a subject a therapeutically effective amount of a composition so that the subject has an improvement in the disease or condition. The improvement is any observable or measurable improvement. Thus, one of skill in the art realizes that a treatment may improve the patient's condition, but may not be a complete cure of the disease. Treating may also comprise treating subjects at risk of developing a disease and/or condition.

II. The Present Invention

The present invention is directed to therapeutic compositions and methods of using the same. In one embodiment, the therapeutic composition is an agonist and/or antagonist of a $NC_{Ca-ATP}$ channel of a neuronal cell, a neuroglial cell, or a neural endothelial cell.

In certain embodiments, the present invention is directed to a method of treating a cancer patient in need of such treatment comprising administering an agonist of a $NC_{Ca-ATP}$ channel of an astrocyte, wherein the agonist activates a $NC_{Ca-ATP}$ channel. In specific embodiments, the agonist targets a SUR1 of the $NC_{Ca-ATP}$ channel. In certain embodiments, the cancer is located in the brain and, more specifically, comprises a metastatic tumor located in the brain.

In certain embodiments, the agonist of the present invention disrupts the integrity of the tumor-brain barrier surrounding the cancer, thereby permitting access to otherwise barred agents across the tumor-brain barrier. In certain embodiments, the agonist is administered in combination with an anti-cancer therapy, including chemotherapy, radiotherapy and/or immunotherapy.

Alternatively, the present invention is directed to a method of disrupting a tumor-brain barrier comprising administering an agonist of a $NC_{Ca-ATP}$ channel of an astrocyte, wherein said agonist activates said $NC_{Ca-ATP}$ channel.

Methods involving an agonist of the $NC_{Ca-ATP}$ channel are directed to selectively killing neuronal cells, neuroglial cells (e.g., astrocytes) and/or neural endothelial cells expressing the $NC_{Ca-ATP}$ channel by infusion of an agonist of the $NC_{Ca-ATP}$ channel, such as diazoxide, to the astrocyte. The infusion can be direct or indirect. Selective killing of neuronal cells, neuroglial cells (e.g., astrocytes) and/or neural endothelial cells are desirable when treating a pathology involving a gliotic capsule, such as a metastatic brain tumor. The agonist facilitates mounting an immune response, or, alternatively, improves permeability for chemotherapeutic agents.

As described herein, the sulfonylurea receptor 1 (SUR1) is expressed in R1 astrocytes as part of the $NC_{Ca-ATP}$ channel, which make up the tumor-brain barrier (TBB) in brain metastasis. Targeting the SUR1 of the R1 astrocytes with an agonist thereof compromises the integrity of the TBB, thereby providing a treatment mechanism for metastatic tumors in the brain. In specific embodiments, the agonists of the present invention disrupt the integrity of the gliotic capsule surrounding the foreign body, thereby permitting entry of otherwise barred biological and/or endogenous compounds, such as leukocytes, into the gliotic capsule.

In certain embodiments, the agonists include, for example, a compound capable of opening, activating and/or increasing the activity of an neuronal cells, neuroglial cells (e.g., astrocytes) and/or neural endothelial cells expressing $NC_{Ca-ATP}$ channel. Specifically, the agonists are SUR1 activators such as, diazoxide and the like, which are known in the art to open (activate) K channels.

The present invention is contemplated for use in combination with chemotherapy, immunotherapy and/or radiotherapy. In the treatment of solid tumors (e.g., tumors in the lung, colon, breast, and brain), efficient treatment is hindered by the difficulty in penetrating the tumor mass with anti-cancer agents (Jain, 1994). The identification of a means by which to facilitate the delivery of therapeutic agents to the cancer site is needed to enhance the effectiveness of current anti-cancer therapies. To address this need, in alternative embodiments, Applicants provide herein methods for enhancing, improving and/or increasing anti-cancer therapies by administering an antagonist of a $NC_{Ca-ATP}$ channel.

For in vitro work, various solid tumor models may be used, such as, for example, the well-recognized inducible breast cancer model, from which tumor cells may be harvested and re-implanted into the brain to produce autologous "metastatic" tumors.

In addition to the sulfonylurea receptor 1 (SUR1) being expressed in R1 astrocytes as part of the $NC_{Ca-ATP}$ channel, the present invention further describes that the SUR1 regulatory subunit of this channel is up-regulated in neurons and capillary endothelial cells following ischemia, and blocking this receptor reduces stroke size, cerebral edema and mortality. Thus, antagonists of the $NC_{Ca-ATP}$ channel may have an important role in preventing, alleviating, inhibiting and/or abrogating the formation of cytotoxic and ionic edema.

In other embodiments, the therapeutic compound of the present invention comprises an antagonist of a $NC_{Ca-ATP}$ channel of a neuronal cell, a neuroglial cell, a neural endothelial cell or a combination thereof. Antagonists are contemplated for use in treating adverse conditions associated with hypoxia and/or ischemia that result in increased intracranial pressure and/or cytotoxic edema of the central nervous system. Such conditions include trauma, ischemic brain injury, namely secondary neuronal injury, and hemorrhagic infarction. Antagonists protect the cells expressing the $NC_{Ca-ATP}$ channel, which is desirable for clinical treatment in which gliotic capsule integrity is important and must be maintained to prevent the spread of infection, such as with a brain abscess. The protection via inhibition of the $NC_{Ca-ATP}$ channel is associated with a reduction in cerebral edema.

In one aspect, the $NC_{Ca-ATP}$ channel is blocked, inhibited, or otherwise is decreased in activity. In such examples, an antagonist of the $NC_{Ca-ATP}$ channel is administered and/or applied. The antagonist modulates the $NC_{Ca-ATP}$ channel such that flux through the channel is reduced, ceased, decreased and/or stopped. The antagonist may have a reversible or an irreversible activity with respect to the activity of the $NC_{Ca-ATP}$ channel of the neuronal cell, neuroglial cell, endothelial cell or a combination thereof. The antagonist may prevent or lessen the depolarization of the cells thereby lessening cell swelling due to osmotic changes that can result from depolarization of the cells. Thus, inhibition of the $NC_{Ca\text{-}ATP}$ channel can reduce cytotoxic edema and death of endothelial cells.

Subjects that can be treated with the therapeutic composition of the present invention include, but are not limited subjects suffering from or at risk of developing conditions associated hypoxia and/or ischemia that result in increased intracranial pressure and/or with cytotoxic edema of the central nervous system (CNS). Such conditions include, but are not limited to trauma (e.g., traumatic brain injury (TBI), concussion) ischemic brain injury, hemorrhagic infarction, stroke, atrial fibrillations, clotting disorders, pulmonary emboli, arteriovenous malformations, mass-occupying lesions (e.g., hematomas), etc. Still further subjects at risk of developing such conditions can include subjects undergoing treatments that increase the risk of stroke, for example, surgery (vascular or neurological), treatment of myocardial infarction with thrombolytics, cerebral/endovascular treatments, stent placements, angiography, etc.

Another aspect of the present invention comprises co-administration of an antagonist of the $NC_{Ca\text{-}ATP}$ channel with a thrombolytic agent. Co-administration of these two compounds increase the therapeutic window of the thrombolytic agent by reducing hemorrhagic conversion. The therapeutic window for thrombolytic agents may be increased by several (4-8) hours by co-administering antagonist of the $NC_{Ca\text{-}ATP}$ channel.

In addition to a thrombolytic agent, other agents can be used in combination with the antagonist of the present invention, for example, but not limited to antiplatelets, anticoagulants, vasodilators, statins, diuretics, etc.

Another aspect of the present invention comprises the use of labeled SUR1 antagonists to diagnose, determine or monitor stages of stroke, cerebral edema or visualize the size/boundaries/borders of a tumor and/or the stroke. For example, the penumbra following the stroke may be monitored or visualized using labeled SUR1 antagonists.

Yet further, the compositions of the present invention can be used to produce neuroprotective kits that are used to treat subjects at risk or suffering from conditions that are associated with cytotoxic cerebral edema.

III. $NC_{Ca\text{-}ATP}$ Channel

The invention is based, in part, on the discovery of a specific channel, the $NC_{Ca\text{-}ATP}$ channel, defined as a channel on astrocytes in US Application Publication No. 20030215889, which is incorporated herein by reference in its entirety. More specifically, the present invention has further defined that this channel is not only expressed on astrocytes, it is expressed on neural cells, neuroglial cells, and/or neural endothelial cells after brain trauma, for example, an hypoxic event, an ischemic event, or other secondary neuronal injuries relating to these events.

The $NC_{Ca\text{-}ATP}$ channel is activated by calcium ions ($Ca^{2+}$) and is sensitive to ATP. Thus, this channel is a non-selective cation channel activated by intracellular $Ca^{2+}$ and blocked by intracellular ATP. When opened by depletion of intracellular ATP, this channel is responsible for complete depolarization due to massive $Na^+$ influx, which creates an electrical gradient for $Cl^-$ and an osmotic gradient for $H_2O$, resulting in cytotoxic edema and cell death. When the channel is blocked or inhibited, massive $Na^+$ does not occur thereby preventing cytotoxic edema.

Certain functional characteristics distinguishes the $NC_{Ca\text{-}ATP}$ channel from other known ion channels. These characteristics can include, but are not limited to 1) it is a non-selective cation channels that readily allows passage of $Na^+$, $K^-$ and other monovalent cations; 2) it is activated by an increase in intracellular calcium, and/or by a decrease in intracellular ATP; 3) it is regulated by sulfonylurea receptor type 1 (SUR1), which heretofore had been considered to be associated exclusively with $K_{ATP}$ channels such as those found in pancreatic β cells.

More specifically, the $NC_{Ca\text{-}ATP}$ channel of the present invention has a single-channel conductance to potassium ion ($K^+$) between 20 and 50 pS. The $NC_{Ca\text{-}ATP}$ channel is also stimulated by $Ca^{2+}$ on the cytoplasmic side of the cell membrane in a physiological concentration range, where concentration range is from $10^{-8}$ to $10^{-5}$ M. The $NC_{Ca\text{-}ATP}$ channel is also inhibited by cytoplasmic ATP in a physiological concentration range, where the concentration range is from $10^{-1}$ to 10 M. The $NC_{Ca\text{-}ATP}$ channel is also permeable to the following cations; $K^+$, $Cs^+$, $Li^+$, $Na^+$; to the extent that the permeability ratio between any two of the cations is greater than 0.5 and less than 2.

IV. Modulators of the $NC_{Ca\text{-}ATP}$ Channel

The present invention comprises modulators of the channel, for example agonists and/or antagonist of the channel. Examples of antagonist or agonist of the present invention may encompass agonist and/or antagonists identified in US Application Publication No. 20030215889, which is incorporated herein by reference in its entirety. One of skill in the art is aware that the $NC_{Ca\text{-}ATP}$ channel is comprised to two subunits, the regulatory subunit, SUR1, and the pore forming subunit.

A. Modulators of SUR1

In certain embodiments, antagonists to sulfonylurea receptor-1 (SUR1) are suitable for blocking the channel. Examples of suitable SUR1 antagonists include, but are not limited to glibenclamide, tolbutamide, repaglinide, nateglinide, meglitinide, midaglizole, LY397364, LY389382, glyclazide, glimepiride, estrogen, estrogen related compounds estrogen-related compounds estrogen related-compounds (estradiol, estrone, estriol, genistein, non-steroidal estrogen (e.g., diethystilbestrol), phytoestrogen (e.g., coumestrol), zearalenone, etc.) and combinations thereof. In a preferred embodiment of the invention the SUR1 antagonists is selected from the group consisting of glibenclamide and tolbutamide. Yet further, another antagonist can be MgADP. Other antagonist include blockers of $K_{ATP}$ channels, for example, but not limited to tolbutamide, glyburide (1[p-2[5-chloro-O-anisamido)ethyl] phenyl] sulfonyl]-3-cyclohexyl-3-urea); chlopropamide (1-[[(p-chlorophenyl)sulfonyl]-3-propylurea; glipizide (1-cyclohexyl-3[[p-[2(5-methylpyrazine carboxamido) ethyl] phenyl] sulfonyl] urea); or tolazamide(benzenesulfonamide-N-[[(hexahydro-1H-azepin-1yl)amino] carbonyl]-4-methyl).

Agonists that can be used in the present invention include, but are not limited to agonist of SUR1, for example, diazoxide, pinacidil, P1075, cromakalin or activators of $K_{ATP}$ channels. Other agonists can include, but are not limited to diazoixde derivatives, for example 3-isopropylamino-7-methoxy-4H-1,2,4-benzothiadiazine 1,1-dioxide (NNC 55-9216), 6,7-dichloro-3-isopropylamino-4H-1,2,4-benzothiadiazine 1,1-dioxide (BPDZ 154), 7-chloro-3-isopropylamino-4H-1,2,4-benzothiadiazine 1,1-dioxide (BPDZ 73), 6-Chloro-3-isopropylamino-4H-thieno[3,2-e]-1,2,4-thiadiazine 1,1-dioxide (NNC 55-0118)4, 6-chloro-3-(1-methylcyclopropyl)amino-4H-thieno[3,2-e]-1,2,4-thiadiazine 1,1-dioxide (NN414), 3-(3-methyl-2-butylamino)-4H-pyrido[4,3-e]-1,2,4-thiadiazine 1,1-dioxide (BPDZ 44), 3-(1',2',2'- trimethylpropyl)amino-4H-pyrido(4,3-e)-1,2,4-thiadiazine 1,1-dioxide (BPDZ 62), 3-(1',2',2'-trimethylpropyl)amine-4H-pyrido (2,3-e)-1,2,4-thiadiazine, 1,1-dioxide (BPDZ 79), 2-alkyl-3-alkylamino-2H-benzo- and 2-alkyl-3-alkylamino-2H-pyrido[4,3-e]-1,2,4-thiadiazine 1,1-dioxides, 6-Chloro-3-alkylamino-4H-thieno[3,2-e]-1,2,4-thiadiazine 1,1-dioxide derivatives, 4-N-Substituted and -unsubstituted 3-alkyl- and 3-(alkylamino)-4H-pyrido[4,3-e]-1,2,4-thiadiazine 1,1-dioxides. In addition, other compounds, including 6-chloro-2-methylquinolin-4(1H)-one (HEI 713) and LN 533021, as well as the class of drugs, arylcyanoguanidines, are known activators or agonist of SUR1.

B. Modulators of SUR1 Transcription and/or Translation

In certain embodiments, the modulator can be a compound (protein, nucleic acid, siRNA, etc.) that modulates transcription and/or translation of SUR1 (regulatory subunit) and/or the molecular entities that comprise the pore-forming subunit.

1. Transcription Factors

Transcription factors are regulatory proteins that binds to a specific DNA sequence (e.g., promoters and enhancers) and regulate transcription of an encoding DNA region. Thus, transcription factors can be used to modulate the expression of SUR1. Typically, a transcription factor comprises a binding domain that binds to DNA (a DNA binding domain) and a regulatory domain that controls transcription. Where a regulatory domain activates transcription, that regulatory domain is designated an activation domain. Where that regulatory domain inhibits transcription, that regulatory domain is designated a repression domain. More specifically, transcription factors such as Sp1 and HIF1$\alpha$ can be used to modulate expression of SUR1.

2. Antisense and Ribozymes

An antisense molecule that binds to a translational or transcriptional start site, or splice junctions, are ideal inhibitors. Antisense, ribozyme, and double-stranded RNA molecules target a particular sequence to achieve a reduction or elimination of a particular polypeptide, such as SUR1. Thus, it is contemplated that antisense, ribozyme, and double-stranded RNA, and RNA interference molecules are constructed and used to modulate SUR1.

a) Antisense Molecules

Antisense methodology takes advantage of the fact that nucleic acids tend to pair with complementary sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNAs, are employed to inhibit gene transcription or translation or both within a host cell, either in vitro or in vivo, such as within a host animal, including a human subject.

Antisense constructs are designed to bind to the promoter and other control regions, exons, introns or even exon-intron boundaries of a gene. It is contemplated that the most effective antisense constructs may include regions complementary to intron/exon splice junctions. Thus, antisense constructs with complementarity to regions within 50-200 bases of an intron-exon splice junction are used. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

It is advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

b) RNA Interference

It is also contemplated in the present invention that double-stranded RNA is used as an interference molecule, e.g., RNA interference (RNAi). RNA interference is used to "knock down" or inhibit a particular gene of interest by simply injecting, bathing or feeding to the organism of interest the double-stranded RNA molecule. This technique selectively "knock downs" gene function without requiring transfection or recombinant techniques (Giet, 2001; Hammond, 2001; Stein P, et al., 2002; Svoboda P, et al., 2001; Svoboda P, et al., 2000).

Another type of RNAi is often referred to as small interfering RNA (siRNA), which may also be utilized to inhibit SUR1. A siRNA may comprises a double stranded structure or a single stranded structure, the sequence of which is "substantially identical" to at least a portion of the target gene (See WO 04/046320, which is incorporated herein by reference in its entirety). "Identity," as known in the art, is the relationship between two or more polynucleotide (or polypeptide) sequences, as determined by comparing the sequences. In the art, identity also means the degree of sequence relatedness between polynucleotide sequences, as determined by the match of the order of nucleotides between such sequences. Identity can be readily calculated. See, for example: Computational Molecular Biology, Lesk, A. M., ed. Oxford University Press, New York, 1988; Biocomputing: Informatics and Genome Projects, Smith, D. W., ea., Academic Press, New York, 1993, and the methods disclosed in WO 99/32619, WO 01/68836, WO 00/44914, and WO 01/36646, specifically incorporated herein by reference. While a number of methods exist for measuring identity between two nucleotide sequences, the term is well known in the art. Methods for determining identity are typically designed to produce the greatest degree of matching of nucleotide sequence and are also typically embodied in computer programs. Such programs are readily available to those in the relevant art. For example, the GCG program package (Devereux et al.), BLASTP, BLASTN, and FASTA (Atschul et al.,) and CLUSTAL (Higgins et al., 1992; Thompson, et al., 1994).

Thus, siRNA contains a nucleotide sequence that is essentially identical to at least a portion of the target gene, for example, SUR1, or any other molecular entity associated with the $NC_{Ca-ATP}$ channel such as the pore-forming subunit. One of skill in the art is aware that the nucleic acid sequences for SUR1 are readily available in GenBank, for example, GenBank accession L40624, which is incorporated herein by reference in its entirety. Preferably, the siRNA contains a nucleotide sequence that is completely identical to at least a portion of the target gene. Of course, when comparing an RNA sequence to a DNA sequence, an "identical" RNA sequence will contain ribonucleotides where the DNA sequence contains deoxyribonucleotides, and further that the RNA sequence will typically contain a uracil at positions where the DNA sequence contains thymidine.

One of skill in the art will appreciate that two polynucleotides of different lengths may be compared over the entire length of the longer fragment. Alternatively, small regions may be compared. Normally sequences of the same length are compared for a final estimation of their utility in the practice of the present invention. It is preferred that there be 100% sequence identity between the dsRNA for use as siRNA and at least 15 contiguous nucleotides of the target gene (e.g., SUR1), although a dsRNA having 70%, 75%, 80%, 85%, 90%, or 95% or greater may also be used in the present invention. A siRNA that is essentially identical to a least a portion of the target gene may also be a dsRNA wherein one of the two complementary strands (or, in the case of a self-complementary RNA, one of the two self-complementary portions) is either identical to the sequence of that portion or the target gene or contains one or more insertions, deletions or single point mutations relative to the nucleotide sequence of that portion of the target gene. siRNA technology thus has the property of being able to tolerate sequence variations that might be expected to result from genetic mutation, strain polymorphism, or evolutionary divergence.

There are several methods for preparing siRNA, such as chemical synthesis, in vitro transcription, siRNA expression vectors, and PCR expression cassettes. Irrespective of which method one uses, the first step in designing an siRNA molecule is to choose the siRNA target site, which can be any site in the target gene. In certain embodiments, one of skill in the art may manually select the target selecting region of the gene, which may be an ORF (open reading frame) as the target selecting region and may preferably be 50-100 nucleotides downstream of the "ATG" start codon. However, there are several readily available programs available to assist with the design of siRNA molecules, for example siRNA Target Designer by Promega, siRNA Target Finder by GenScript Corp., siRNA Retriever Program by Imgenex Corp., EMBOSS siRNA algorithm, siRNA program by Qiagen, Ambion siRNA predictor, Ambion siRNA predictor, Whitehead siRNA prediction, and Sfold. Thus, it is envisioned that any of the above programs may be utilized to produce siRNA molecules that can be used in the present invention.

c) Ribozymes

Ribozymes are RNA-protein complexes that cleave nucleic acids in a site-specific fashion. Ribozymes have specific catalytic domains that possess endonuclease activity (Kim and Cech, 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression is particularly suited to therapeutic applications (Scanlon et al., 1991; Sarver et al., 1990; Sioud et al., 1992). Most of this work involved the modification of a target mRNA, based on a specific mutant codon that is cleaved by a specific ribozyme. In light of the information included herein and the knowledge of one of ordinary skill in the art, the preparation and use of additional ribozymes that are specifically targeted to a given gene will now be straightforward.

Other suitable ribozymes include sequences from RNase P with RNA cleavage activity (Yuan et al., 1992; Yuan and Altman, 1994), hairpin ribozyme structures (Berzal-Herranz et al., 1992; Chowrira et al., 1993) and hepatitis δ virus based ribozymes (Perrotta and Been, 1992). The general design and optimization of ribozyme directed RNA cleavage activity has been discussed in detail (Haseloff and Gerlach, 1988; Symons, 1992; Chowrira, et al., 1994; and Thompson, et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozymes, the cleavage site is a dinucleotide sequence on the target RNA, uracil (U) followed by either an adenine, cytosine or uracil (A, C or U; Perriman, et al., 1992; Thompson, et al., 1995). The frequency of this dinucleotide occurring in any given RNA is statistically 3 out of 16.

Designing and testing ribozymes for efficient cleavage of a target RNA is a process well known to those skilled in the art. Examples of scientific methods for designing and testing ribozymes are described by Chowrira et al. (1994) and Lieber and Strauss (1995), each incorporated by reference. The identification of operative and preferred sequences for use in SUR1 targeted ribozymes is simply a matter of preparing and testing a given sequence, and is a routinely practiced screening method known to those of skill in the art.

C. Methods of Screening for Modulators

Further embodiments of the present invention can include methods for identifying modulators of the $NC_{Ca\text{-}ATP}$ channel, for example, agonist or antagonist, that modify the activity and/or expression. These assays may comprise random screening of large libraries of candidate substances; alternatively, the assays may be used to focus on particular classes of compounds selected with an eye towards structural attributes that are believed to make them more likely to modulate the function or activity or expression of the $NC_{Ca\text{-}ATP}$ channel.

By function, it is meant that one may assay for mRNA expression, protein expression, protein activity, or channel activity, more specifically, the ability of the modulator to open or inhibit or block the $NC_{Ca\text{-}ATP}$ channel. Thus, the compounds for screening in accordance with the invention include, but are not limited to natural or synthetic organic compounds, peptides, antibodies and fragments thereof, peptidomimetics, that bind to the $NC_{Ca\text{-}ATP}$ channel and either open the channel (e.g., agonists) or block the channel (e.g., antagonists). For use in the treatment of neural cell swelling or brain swelling, compounds that block the channel are preferred. Agonists that open or maintain the channel in the open state include peptides, antibodies or fragments thereof, and other organic compounds that include the SUR1 subunit of the $NC_{Ca-ATP}$ channel (or a portion thereof) and bind to and "neutralize" circulating ligand for SUR1.

With reference to screening of compounds that affect the $NC_{Ca-ATP}$ channel, libraries of known compounds can be screened, including natural products or synthetic chemicals, and biologically active materials, including proteins, for compounds which are inhibitors or activators. Preferably, such a compound is an $NC_{Ca-ATP}$ antagonist, which includes an $NC_{Ca-ATP}$ channel inhibitor, an $NC_{Ca-ATP}$ channel blocker, a SUR1 antagonist, SUR1 inhibitor, and/or a compound capable of reducing the magnitude of membrane current through the channel.

Compounds may include, but are not limited to, small organic or inorganic molecules, compounds available in compound libraries, peptides such as, for example, soluble peptides, including but not limited to members of random peptide libraries; (see, e.g., Lam, K. S. et al., 1991, Nature 354: 82-84; Houghten, R. et al., 1991, Nature 354: 84-86), and combinatorial chemistry-derived molecular library made of D- and/or L-configuration amino acids, phosphopeptides (including, but not limited to, members of random or partially degenerate, directed phosphopeptide libraries; see, e.g., Songyang, Z. et al., 1993, Cell 72: 767-778), antibodies (including, but not limited to, polyclonal, monoclonal, humanized, anti-idiotypic, chimeric or single chain antibodies, and FAb, $F(ab')_2$ and FAb expression library fragments, and epitope-binding fragments thereof).

Other compounds which can be screened in accordance with the invention include but are not limited to small organic molecules that are able to cross the blood-brain barrier, gain entry into an appropriate neural cell and affect the expression of the $NC_{Ca-ATP}$ channel gene or some other gene involved in the $NC_{Ca-ATP}$ channel activity (e.g., by interacting with the regulatory region or transcription factors involved in gene expression); or such compounds that affect the activity of the $NC_{Ca-ATP}$ channel or the activity of some other intracellular factor involved in the $NC_{Ca-ATP}$ channel activity.

To identify, make, generate, provide, manufacture or obtain modulator, one generally will determine the activity of the $NC_{Ca-ATP}$ channel in the presence, absence, or both of the candidate substance, wherein an inhibitor or antagonist is defined as any substance that down-regulates, reduces, inhibits, blocks or decreases the $NC_{Ca-ATP}$ channel expression or activity, and wherein an activator or agonist is defined as any substance that up-regulates, enhances, activates, increases or opens the $NC_{Ca-ATP}$ channel. For example, a method may generally comprise:

(a) providing a candidate substance suspected of activating or inhibiting the $NC_{Ca-ATP}$ channel expression or activity in vitro or in vivo;

(b) assessing the ability of the candidate substance to activate or inhibit the $NC_{Ca-ATP}$ channel expression or activity in vitro or in vivo;

(c) selecting an modulator; and (d) manufacturing the modulator.

In certain embodiments, an alternative assessing step can be assessing the ability of the candidate substance to bind specifically to the $NC_{Ca-ATP}$ channel in vitro or in vivo;

In further embodiments, the $NC_{Ca-ATP}$ channel may be provided in a cell or a cell free system and the $NC_{Ca-ATP}$ channel may be contacted with the candidate substance. Next, the modulator is selected by assessing the effect of the candidate substance on the $NC_{Ca-ATP}$ channel activity or expression. Upon identification of the modulator, the method may further provide manufacturing of the modulator.

V. Methods of Cancer Treatment

A. Treatment with an Agonist

In certain embodiments, the present invention is directed to a method of treating a cancer patient in need of such treatment comprising administering an agonist of a $NC_{Ca-ATP}$ channel of an neuronal cell or a neuroglia cell or a neural endothelial cell, wherein the agonist activates a $NC_{Ca-ATP}$ channel. In specific embodiments, the agonist targets a SUR1 of the $NC_{Ca-ATP}$ channel. In certain embodiments, the cancer is located in the brain and, more specifically, comprises a metastatic tumor located in the brain.

Alternatively, the present invention is directed to a method of disrupting a tumor-brain barrier comprising administering an agonist of a $NC_{Ca-ATP}$ channel of an astrocyte, wherein said agonist activates said $NC_{Ca-ATP}$ channel.

With the administration of an agonist of the $NC_{Ca-ATP}$ channel, cell proliferation is abrogated, slowed, reduced or inhibited due to the opening of the $NC_{Ca-ATP}$ channel. Such neuronal cells in which the agonist the $NC_{Ca-ATP}$ channel may be administered may include any cell that expresses SUR1.

An effective amount of an agonist or antagonist of $NC_{Ca-ATP}$ channel that may be administered to a cell includes a dose of about 0.0001 nM to about 200 μM. More specifically, doses of an agonist to be administered are from about 0.01 nM to about 2000 μM; about 0.01 μM to about 0.05 μM; about 0.05 μM to about 1.0 μM; about 1.0 μM to about 1.5 μM; about 1.5 μM to about 2.0 μM; about 2.0 μM to about 3.0 μM; about 3.0 μM to about 4.0 μM; about 4.0 μM to about 5.0 μM; about 5.0 μM to about 10 μM; about 10 μM to about 50 μM; about 50 μM to about 100 μM; about 100 μM to about 200 μM; about 200 μM to about 300 μM; about 300 μM to about 500 μM; about 500 μM to about 1000 μM; about 1000 μM to about 1500 μM and about 1500 μM to about 2000 μM. Of course, all of these amounts are exemplary, and any amount in-between these points is also expected to be of use in the invention.

It is envisioned that an agonist of $NC_{Ca-ATP}$ channel or related-compound thereof will inhibit the proliferation of a cell or growth of a neoplasm, either directly or indirectly, by measurably slowing, stopping, or reversing the growth rate of the cell or neoplasm or neoplastic cells in vitro or in vivo. Desirably, the growth rate is slowed by 20%, 30%, 50%, or 70% or more, as determined using a suitable assay for determination of cell growth rates.

Still further, the present invention provides methods for the treatment of a cancer by administering an agonist of the $NC_{Ca-ATP}$ channel. The agonist or related-compound thereof can be administered parenterally or alimentary. Parenteral administrations include, but are not limited to intravenously, intradermally, intramuscularly, intraarterially, intrathecally, intraventricularly, intratumorally, subcutaneous, or intraperitoneally U.S. Pat. Nos. 6,613,308, 5,466,468, 5,543,158; 5,641,515; and 5,399,363 (each specifically incorporated herein by reference in its entirety). Alimentary administrations include, but are not limited to orally, buccally, rectally, or sublingually.

The administration of the therapeutic compounds and/or the therapies of the present invention may include systemic, local and/or regional and may oral, intravenous, and intramuscular. Alternatively, other routes of administration are also contemplated such as, for example, arterial perfusion, intracavitary, intraperitoneal, intrapleural, intraventricular, intratumoral, intraparenchyma and/or intrathecal. If desired the therapeutic compound may be administered by the same route as the chemotherapeutic agent, even if the therapeutic compound and the chemotherapeutic agent are not administered simultaneously. The skilled artisan is aware of determining the appropriate administration route using standard methods and procedures. In one example, where assessment of a response to chemotherapy, both peripherally and centrally is desired, the health care professional may use a systemic administration.

Treatment methods will involve treating an individual with an effective amount of a composition containing an agonist of $NC_{Ca-ATP}$ channel or related-compound thereof. An effective amount is described, generally, as that amount sufficient to detectably and repeatedly to ameliorate, reduce, minimize or limit the extent of a disease or its symptoms. More specifically, it is envisioned that the treatment with the an agonist of $NC_{Ca-ATP}$ channel or related-compounds thereof will kill cells, inhibit cell growth, inhibit cell proliferation, inhibit metastasis, decrease tumor size and otherwise reverse or reduce the malignant phenotype of tumor cells, either directly or indirectly.

The effective amount of "therapeutically effective amounts" of the an agonist of $NC_{Ca-ATP}$ channel or related-compounds thereof to be used are those amounts effective to produce beneficial results, particularly with respect to cancer treatment, in the recipient animal or patient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

As is well known in the art, a specific dose level of active compounds such as an agonist of $NC_{Ca-ATP}$ channel or related-compounds thereof for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

A therapeutically effective amount of an agonist of $NC_{Ca-ATP}$ channel or related-compounds thereof as a treatment varies depending upon the host treated and the particular mode of administration. In one embodiment of the invention the dose range of the agonist of $NC_{Ca-ATP}$ channel or related-compounds thereof will be about 0.0001 μg/kg body weight to about 500 mg/kg body weight. The term "body weight" is applicable when an animal is being treated. When isolated cells are being treated, "body weight" as used herein should read to mean "total cell body weight". The term "total body weight" may be used to apply to both isolated cell and animal treatment. All concentrations and treatment levels are expressed as "body weight" or simply "kg" in this application are also considered to cover the analogous "total cell body weight" and "total body weight" concentrations. However, those of skill will recognize the utility of a variety of dosage range, for example, 0.0001 μg/kg body weight to 450 mg/kg body weight, 0.0002 μg/kg body weight to 400 mg/kg body weight, 0.0003 μg/kg body weight to 350 mg/kg body weight, 0.0004 μg/kg body weight to 300 mg/kg body weight, 0.0005 μg/kg body weight to 250 mg/kg body weight, 5.0 μg/kg body weight to 200 mg/kg body weight, 10.0 μg/kg body weight to 150 mg/kg body weight, 100.0 μg/kg body weight to 100 mg/kg body weight, or 1000 μg/kg body weight to 50 mg/kg body weight. Further, those of skill will recognize that a variety of different dosage levels will be of use, for example, 0.0001 μg/kg, 0.0002 μg/kg, 0.0003 μg/kg, 0.0004 μg/kg, 0.005 μg/kg, 0.0007 μg/kg, 0.001 μg/kg, 0.1 μg/kg, 1.0 μg/kg, 1.5 μg/kg, 2.0 μg/kg, 5.0 μg/kg, 10.0 μg/kg, 15.0 μg/kg, 30.0 μg/kg, 50 μg/kg, 75 μg/kg, 80 μg/kg, 90 μg/kg, 100 μg/kg, 120 μg/kg, 140 μg/kg, 150 μg/kg, 160 μg/kg, 180 μg/kg, 200 μg/kg, 225 μg/kg, 250 μg/kg, 275 μg/kg, 300 μg/kg, 325 μg/kg, 350 μg/kg, 375 μg/kg, 400 μg/kg, 450 μg/kg, 500 μg/kg, 550 μg/kg, 600 μg/kg, 700 μg/kg, 750 μg/kg, 800 μg/kg, 900 μg/kg, 1 mg/kg, 5 mg/kg, 10 mg/kg, 12 mg/kg, 15 mg/kg, 20 mg/kg, and/or 30 mg/kg. Of course, all of these dosages are exemplary, and any dosage in-between these points is also expected to be of use in the invention. Any of the above dosage ranges or dosage levels may be employed for an agonist of $NC_{Ca-ATP}$ channel or related-compounds thereof.

Administration of the therapeutic agonist of $NC_{Ca-ATP}$ channel composition of the present invention to a patient or subject will follow general protocols for the administration of chemotherapeutics, taking into account the toxicity, if any, of the agonist of $NC_{Ca-ATP}$ channel. It is expected that the treatment cycles would be repeated as necessary. It also is contemplated that various standard therapies, as well as surgical intervention, may be applied in combination with the described therapy.

The treatments may include various "unit doses." Unit dose is defined as containing a predetermined quantity of the therapeutic composition (an agonist of $NC_{Ca-ATP}$ channel or its related-compounds thereof) calculated to produce the desired responses in association with its administration, e.g., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time.

According to the present invention, one may treat the cancer by directly injection a tumor with an agonist of $NC_{Ca-ATP}$ channel or related-compound composition. Alternatively, the tumor may be infused or perfused with the composition using any suitable delivery vehicle. Local or regional administration, with respect to the tumor, also is contemplated. More preferably, systemic administration or oral administration may be performed. Continuous administration also may be applied where appropriate, for example, where a tumor is excised and the tumor bed is treated to eliminate residual, microscopic disease. Delivery via syringe or catheterization is preferred. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs. For tumors of >4 cm, the volume to be administered will be about 4-10 ml (preferably 10 ml), while for tumors of <4 cm, a volume of about 1-3 ml will be used (preferably 3 ml). Multiple injections delivered as single dose comprise about 0.1 to about 1 ml volumes.

In certain embodiments, the tumor being treated may not, at least initially, be resectable. Treatments with therapeutic agonist of $NC_{Ca-ATP}$ channel compositions may increase the resectability of the tumor due to shrinkage at the margins, either directly or indirectly, or by elimination of certain particularly invasive portions. Following treatments, resection may be possible. Additional treatments subsequent to resection will serve to eliminate microscopic residual disease at the tumor site.

B. Combined Cancer Therapy with an Agonist of $NC_{Ca-ATP}$ Channel and/or Other Anticancer Agents In the context of the present invention, it is contemplated that an agonist of $NC_{Ca-ATP}$ channel or related-compounds thereof may be used in combination with an additional therapeutic agent to more effectively treat cancer. Anticancer agents may include but are not limited to, radiotherapy, chemotherapy, gene therapy, hormonal therapy or immunotherapy that targets cancer/tumor cells.

When an additional therapeutic agent is administered, as long as the dose of the additional therapeutic agent does not exceed previously quoted toxicity levels, the effective amounts of the additional therapeutic agent may simply be defined as that amount effective to inhibit and/or reduce the cancer growth when administered to an animal in combination with an agonist of $NC_{Ca-ATP}$ channel or related-compounds thereof. This may be easily determined by monitoring the animal or patient and measuring those physical and biochemical parameters of health and disease that are indicative of the success of a given treatment. Such methods are routine in animal testing and clinical practice.

To kill cells, induce cell-cycle arrest, inhibit cell growth, inhibit metastasis, inhibit angiogenesis or otherwise reverse or reduce the malignant phenotype of cancer cells, either directly or indirectly, using the methods and compositions of the present invention, one would generally contact a cell with agonist of $NC_{Ca-ATP}$ channel or related-compounds thereof in combination with an additional therapeutic agent. These compositions would be provided in a combined amount effective to inhibit cell growth and/or induce apoptosis in the cell. This process may involve contacting the cells with agonist of $NC_{Ca-ATP}$ channel or related-compounds thereof in combination with an additional therapeutic agent or factor(s) at the same time. This may be achieved by contacting the cell with a single composition or pharmacological formulation that includes both agents, or by contacting the cell with two distinct compositions or formulations, at the same time, wherein one composition includes an agonist of $NC_{Ca-ATP}$ channel or derivatives thereof and the other includes the additional agent.

Alternatively, treatment with an agonist of $NC_{CaATP}$ channel or related-compounds thereof may precede or follow the additional agent treatment by intervals ranging from minutes to weeks. In embodiments where the additional agent is applied separately to the cell, one would generally ensure that a significant period of time did not expire between the time of each delivery, such that the agent would still be able to exert an advantageously combined effect on the cell. In such instances, it is contemplated that one would contact the cell with both modalities within about 12-24 hr of each other and, more preferably, within about 6-12 hr of each other, with a delay time of only about 12 hr being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either an agonist of $NC_{Ca-ATP}$ channel or related-compounds thereof in combination with an additional therapeutic agent such as an anticancer agent will be desired. Various combinations may be employed, where an agonist of $NC_{Ca-ATP}$ channel or related-compounds thereof is "A" and the additional therapeutic agent is "B", as exemplified below:

```
A/B/A B/A/B B/B/A A/A/B B/A/A A/B/B B/B/B/A
B/B/A/B A/A/B/B A/B/A/B A/B/B/A B/B/A/A B/A/B/A
B/A/A/B B/B/B/A A/A/A/B B/A/A/A A/B/A/A A/A/B/A
A/B/B/B B/A/B/B B/B/A/B
```

1. Chemotherapeutic Agents

In some embodiments of the present invention chemotherapy may be administered, as is typical, in regular cycles. A cycle may involve one dose, after which several days or the weeks without treatment ensues for normal tissues to recover from the drug's side effects. Doses may be given several days in a row, or every other day for several days, followed by a period of rest. If more than one drug is used, the treatment plan will specify how often and exactly when each drug should be given. The number of cycles a person receives may be determined before treatment starts (based on the type and stage of cancer) or may be flexible, in order to take into account how quickly the tumor is shrinking. Certain serious side effects may also require doctors to adjust chemotherapy plans to allow the patient time to recover.

Chemotherapeutic agents that may be used in combination with agonists of the present invention or an related-compound thereof in the treatment of cancer, include, but are not limited to cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, gemcitabien, navelbine, farnesyl-protein transferase inhibitors, transplatinum, 5-fluorouracil and methotrexate, or any related-compound or derivative variant of the foregoing.

2. Radiotherapeutic Agents

Radiotherapeutic agents may also be use in combination with the compounds of the present invention in treating a cancer. Such factors that cause DNA damage and have been used extensively include what are commonly known as 7-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

J. Immunotherapeutic Agents

Immunotherapeutics may also be employed in the present invention in combination with an agonist of $NC_{Ca-ATP}$ channel or related-compounds thereof in treating cancer. Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Generally, the tumor cell must bear some marker that is amenable to targeting, e.g., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

4. Inhibitors of Cellular Proliferation

The tumor suppressor oncogenes function to inhibit excessive cellular proliferation. The inactivation of these genes destroys their inhibitory activity, resulting in unregulated proliferation. The tumor suppressors p53, p16 and C-CAM are described below.

High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently mutated gene in common human cancers. It is mutated in over 50% of human NSCLC (Hollstein et al., 1991) and in a wide spectrum of other tumors.

The p53 gene encodes a 393-amino acid phosphoprotein that can form complexes with host proteins such as large-T antigen and E1B. The protein is found in normal tissues and cells, but at concentrations which are minute by comparison with transformed cells or tumor tissue Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Winberg, 1991).

Another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the G1. The activity of this enzyme may be to phosphorylate Rb at late G1. The activity of CDK4 is controlled by an activating subunit, D-type cyclin, and by an inhibitory subunit, the p16INK4 has been biochemically characterized as a protein that specifically binds to and inhibits CDK4, and thus may regulate Rb phosphorylation (Serrano et al., 1993; Serrano et al., 1995). Since the p16INK4 protein is a CDK4 inhibitor (Serrano, 1993), deletion of this gene may increase the activity of CDK4, resulting in hyperphosphorylation of the Rb protein. p16 also is known to regulate the function of CDK6.

p16INK4 belongs to a newly described class of CDK-inhibitory proteins that also includes p16B, p19, p21WAF1, and p27KIP1. The p16INK4 gene maps to 9p21, a chromosome region frequently deleted in many tumor types. Homozygous deletions and mutations of the p16INK4 gene are frequent in human tumor cell lines. This evidence suggests that the p16INK4 gene is a tumor suppressor gene. This interpretation has been challenged, however, by the observation that the frequency of the p16INK4 gene alterations is much lower in primary uncultured tumors than in cultured cell lines (Caldas et al., 1994; Cheng et al., 1994; Hussussian et al., 1994; Kamb et al., 1994; Okamoto et al., 1994; Arap et al., 1995). Restoration of wild-type p16INK4 function by transfection with a plasmid expression vector reduced colony formation by some human cancer cell lines (Okamoto et al., 1994; Arap et al., 1995).

Other genes that may be employed according to the present invention include Rb, mda-7, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

5. Regulators of Programmed Cell Death

Apoptosis, or programmed cell death, is an essential process in cancer therapy (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Members of the Bcl-2 that function to promote cell death such as Bax, Bak, Bik, Bim, Bid, Bad and Harakiri, are contemplated for use in combination with an agonist of $NC_{Ca-ATP}$ channel or an related-compound thereof in treating cancer.

6. Surgery

It is further contemplated that a surgical procedure may be employed in the present invention. Approximately 60% of persons with cancer will undergo surgery of some type, which includes preventative, diagnostic or staging, curative and palliative surgery. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

7. Other agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine related-compounds; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increased intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

VI. Methods of Cerebral Ischemia Treatment

A. Treatment with an Antagonist

In other embodiments, the therapeutic compound of the present invention comprises an antagonist of a $NC_{Ca\text{-}ATP}$ channel of a neuronal cell, a neuroglial cell, a neural endothelial cell or a combination thereof. Antagonists are contemplated for use in treating adverse conditions associated with intracranial pressure and/or cytotoxic edema of the central nervous system. Such conditions include trauma (e.g., traumatic brain injury (TBI)), ischemic brain injury, primary and secondary neuronal injury, stroke, arteriovenous malformations (AVM), mass-occupying lesion (e.g., hematoma), and hemorrhagic infarction. Antagonists protect the cells expressing the $NC_{Ca\text{-}ATP}$ channel, which is desirable for clinical treatment in which ionic or cytotoxic edema is formed, in which capillary integrity is lost following ischemia, and in which gliotic capsule integrity is important and must be maintained to prevent the spread of infection, such as with a brain abscess. Those of skill in the art realize that a brain abscess is a completely enclosed and results in cerebral swelling. The protection via inhibition of the $NC_{Ca\text{-}ATP}$ channel is associated with a reduction in cerebral ionic and cytotoxic edema. Thus, the compound that inhibits the $NC_{Ca\text{-}ATP}$ channel is neuroprotective.

In one aspect, the $NC_{Ca\text{-}ATP}$ channel is blocked, inhibited, or otherwise is decreased in activity. In such examples, an antagonist of the $NC_{Ca\text{-}ATP}$ channel is administered and/or applied. The antagonist modulates the $NC_{Ca\text{-}ATP}$ channel such that flux (ion and/or water) through the channel is reduced, ceased, decreased and/or stopped. The antagonist may have a reversible or an irreversible activity with respect to the activity of the $NC_{Ca\text{-}ATP}$ channel of the neuronal cell, neuroglial cell, a neural endothelial cell or a combination thereof. Thus, inhibition of the $NC_{Ca\text{-}ATP}$ channel can reduce cytotoxic edema and death of endothelial cells which are associated with formation of ionic edema and with hemorrhagic conversion.

Accordingly, the present invention is useful in the treatment or alleviation of acute cerebral ischemia. According to a specific embodiment of the present invention the administration of effective amounts of the active compound can block the channel, which if remained open leads to neuronal cell swelling and cell death. A variety of antagonists to SUR1 are suitable for blocking the channel. Examples of suitable SUR1 antagonists include, but are not limited to glibenclamide, tolbutamide, repaglinide, nateglinide, meglitinide, midaglizole, LY397364, LY389382, glyclazide, glimepiride, estrogen, estrogen-related compounds and combinations thereof. In a preferred embodiment of the invention the SUR1 antagonists is selected from the group consisting of glibenclamide and tolbutamide. Another antagonist that can be used is MgADP. Still other therapeutic "strategies" for preventing neural cell swelling and cell death can be adopted including, but not limited to methods that maintain the neural cell in a polarized state and methods that prevent strong depolarization.

In further embodiments, inhibitors or antagonist of the $NC_{Ca\text{-}ATP}$ channel can be used to reduce or alleviate or abrogate hemorrhagic conversion. The pathological sequence that takes place in capillaries after ischemia can be divided into 3 stages, based on the principal constituents that move from the intravascular compartment into brain parenchyma (Ayata 2002; Betz, 1996; Betz 1989). The first stage is characterized by formation of "ionic" edema, during which the BBB remains intact, with movement of electrolytes ($Na^+$, $Cl^-$) plus water into brain parenchyma. The second stage is characterized by formation of "vasogenic" edema, due to breakdown of the BBB, during which macromolecules plus water enter into brain parenchyma. The third stage is characterized by hemorrhagic conversion, due to catastrophic failure of capillaries, during which all constituents of blood extravasate into brain parenchyma. In accordance with Starling's law, understanding these phases requires that 2 things be identified: (i) the driving force that "pushes" things into parenchyma; and (ii) the permeability pore that allows passage of these things into parenchyma.

Thus, the use of the antagonist or related-compounds thereof can reduce the mortality of a subject suffering from a stroke and/or rescue the penumbra area or prevent damage in the penumbra area which comprises areas of tissue that are at risk of becoming irreversibly damaged.

With the administration of an antagonist of the $NC_{Ca\text{-}ATP}$ channel, endothelial cell depolarization is abrogated, slowed, reduced or inhibited due to the opening of the $NC_{Ca\text{-}ATP}$ channel. Thus, abrogation of cell depolarization results in abrogation or inhibition of $Na^+$ influx, which prevents a change in osmotic gradient thereby preventing an influx of water into the endothelial cell and stopping cell swelling, blebbing and cytotoxic edema. Thus, preventing or inhibiting or attenuating endothelial cell depolarization can prevent or reduce hemorrhagic conversion.

Neuronal cells in which the antagonist of the $NC_{Ca\text{-}ATP}$ channel may be administered may include any cell that expresses SUR1, for example any neuronal cell, neuroglial cell or a neural endothelia cell.

Subjects that may be treated with the antagonist or related-compound thereof include those that are suffering from or at risk of developing trauma (e.g., traumatic brain injury (TBI)), ischemic brain injury, primary and secondary neuronal injury, stroke, arteriovenous malformations (AVM), brain abscess, mass-occupying lesion, hemorrhagic infarction, or any other condition associated with cerebral hypoxia or cerebral ischemia resulting in cerebral edema and/or increased intracranial pressure, for example, but not limited to brain mass, brain edema, hematoma, end stage cerebral edema, encephalopathies, etc. Thus, the antagonist can be a therapeutic treatment in which the therapeutic treatment includes prophylaxis or a prophylactic treatment. The antagonist or related-compounds thereof are neuroprotective.

Other subjects that may be treated with the antagonist of the present invention include those subjects that are at risk or predisposed to developing a stroke. Such subjects can include, but are not limited to subjects that suffer from atrial fibrillations, clotting disorders, and/or risk of pulmonary emboli.

In certain embodiments, a subject at risk for developing a stroke may include subjects undergoing treatments, for example, but not limited to cerebral/endovascular treatments, surgery (e.g., craniotomy, cranial surgery, removal of brain tumors (e.g., hematoma), coronary artery bypass grafting (CABG), angiography, stent replacement, other vascular surgeries, and/or other CNS or neurological surgeries), and treatment of myocardial infarction (MI) with thrombolytics. In such cases, the subject may be treated with the antagonist or related-compound of the present invention prior to the actual treatment. Pretreatment can include administration of the antagonist and/or related-compound months (1, 2, 3, etc.), weeks (1, 2, 3, etc.), days (1, 2, 3, etc.), hours (1, 2, 3, 4, 5, 6, 7, 8, 9, 10, 11, 12), or minutes (15, 30, 60, 90, etc.) prior to the actual treatment or surgery. Treatment of the antagonist and/or related-compound can continue during the treatment and/or surgery and after the treatment and/or surgery until the risk of developing a stroke in the subject is decreased, lessened or alleviated.

In further embodiments, the antagonist of the present invention can be given to a subject at risk of developing head/neck trauma, such as a subject involved in sports or other activities that have an increased risk of head/neck trauma.

An effective amount of an antagonist of the $NC_{Ca-ATP}$ channel that may be administered to a cell includes a dose of about 0.0001 nM to about 200 μM. More specifically, doses of an agonist to be administered are from about 0.01 nM to about 2000 μM; about 0.01 μM to about 0.05 μM; about 0.05 μM to about 1.0 M; about 1.0 μM to about 1.5 μM; about 1.5 μM to about 2.0 μM; about 2.0 μM to about 3.0 μM; about 3.0 μM to about 4.0 μM; about 4.0 μM to about 5.0 μM; about 5.0 μM to about 10 μM; about 10 μM to about 50 μM; about 50 μM to about 100 μM; about 100 μM to about 200 μM; about 200 μM to about 300 μM; about 300 μM to about 500 μM; about 500 μM to about 1000 μM; about 1000 μM to about 1500 μM and about 1500 μM to about 2000 μM. Of course, all of these amounts are exemplary, and any amount in-between these points is also expected to be of use in the invention.

The antagonist or related-compound thereof can be administered parenterally or alimentary. Parenteral administrations include, but are not limited to intravenously, intradermally, intramuscularly, intraarterially, intrathecally, subcutaneous, or intraperitoneally U.S. Pat. Nos. 6,613,308, 5,466,468, 5,543,158; 5,641,515; and 5,399,363 (each specifically incorporated herein by reference in its entirety). Alimentary administrations include, but are not limited to orally, buccally, rectally, or sublingually.

The administration of the therapeutic compounds and/or the therapies of the present invention may include systemic, local and/or regional administrations, for example, topically (dermally, transdermally), via catheters, implantable pumps, etc. Alternatively, other routes of administration are also contemplated such as, for example, arterial perfusion, intracavitary, intraperitoneal, intrapleural, intraventricular and/or intrathecal. The skilled artisan is aware of determining the appropriate administration route using standard methods and procedures. Other routes of administration are discussed elsewhere in the specification and are incorporated herein by reference.

Treatment methods will involve treating an individual with an effective amount of a composition containing an antagonist of $NC_{Ca-ATP}$ channel or related-compound thereof. An effective amount is described, generally, as that amount sufficient to detectably and repeatedly to ameliorate, reduce, minimize or limit the extent of a disease or its symptoms. More specifically, it is envisioned that the treatment with the an antagonist of $NC_{Ca-ATP}$ channel or related-compounds thereof will inhibit cell depolarization, inhibit $Na^+$ influx, inhibit an osmotic gradient change, inhibit water influx into the cell, inhibit cytotoxic cell edema, decrease stroke size, inhibit hemorrhagic conversion, and decrease mortality of the subject.

The effective amount of an antagonist of $NC_{Ca-ATP}$ channel or related-compounds thereof to be used are those amounts effective to produce beneficial results, particularly with respect to stroke treatment, in the recipient animal or patient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

As is well known in the art, a specific dose level of active compounds such as an antagonist of the $NC_{Ca-ATP}$ channel or related-compounds thereof for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

One of skill in the art realizes that the effective amount of the antagonist or related-compound thereof can be the amount that is required to achieve the desired result: reduction in the risk of stroke, reduction in intracranial pressure, reduction in cell death, reduction in stroke size, etc. This amount also is an amount that maintains a reasonable level of blood glucose in the patient, for example, the amount of the antagonist maintains a blood glucose level of at least 60 mmol/l, more preferably, the blood glucose level is maintain in the range of about 60 mmol/l to about 150 mmol/l. Thus, the amounts prevents the subject from becoming hypoglycemic. If glucose levels are not normal, then one of skill in the art would administer either insulin or glucose, depending upon if the patient is hypoglycemic or hyperglycemic.

An effective amount of an antagonist of the $NC_{Ca-ATP}$ channel or related-compounds thereof as a treatment varies depending upon the host treated and the particular mode of administration. In one embodiment of the invention the dose range of the antagonist of the $NC_{Ca-ATP}$ channel or related-compounds thereof will be about 0.01 μg/kg body weight to about 20,000 μg/kg body weight. The term "body weight" is applicable when an animal is being treated. When isolated cells are being treated, "body weight" as used herein should read to mean "total cell body weight". The term "total body weight" may be used to apply to both isolated cell and animal treatment. All concentrations and treatment levels are expressed as "body weight" or simply "kg" in this application are also considered to cover the analogous "total cell body weight" and "total body weight" concentrations. However, those of skill will recognize the utility of a variety of dosage range, for example, 0.01 μg/kg body weight to 20,000 μg/kg body weight, 0.02 μg/kg body weight to 15,000 μg/kg body weight, 0.03 μg/kg body weight to 10,000 μg/kg body weight, 0.04 μg/kg body weight to 5,000 μg/kg body weight, 0.05 μg/kg body weight to 2,500 μg/kg body weight, 0.06 μg/kg body weight to 1,000 μg/kg body weight, 0.07 μg/kg body weight to 500 μg/kg body weight, 0.08 μg/kg body weight to 400 μg/kg body weight, 0.09 μg/kg body weight to 200 μg/kg body weight or 0.1 μg/kg body weight to 100 μg/kg body weight. Further, those of skill will recognize that a variety of different dosage levels will be of use, for example, 0.0001 μg/kg, 0.0002 μg/kg, 0.0003 μg/kg, 0.0004 μg/kg, 0.005 μg/kg, 0.0007 μg/kg, 0.001 μg/kg, 0.1 μg/kg, 1.0 μg/kg, 1.5 μg/kg, 2.0 μg/kg, 5.0 μg/kg, 10.0 μg/kg, 15.0 μg/kg, 30.0 μg/kg, 50 μg/kg, 75 μg/kg, 80 μg/kg, 90 μg/kg, 100 μg/kg, 120 μg/kg, 140 μg/kg, 150 μg/kg, 160 μg/kg, 180 μg/kg, 200 μg/kg, 225 μg/kg, 250 μg/kg, 275 μg/kg, 300 μg/kg, 325 μg/kg, 350 μg/kg, 375 μg/kg, 400 μg/kg, 450 μg/kg, 500 μg/kg, 550 μg/kg, 600 μg/kg, 700 μg/kg, 750 μg/kg, 800 μg/kg, 900 μg/kg, 1 mg/kg, 5 mg/kg, 10 mg/kg, 12 mg/kg, 15 mg/kg, 20 mg/kg, and/or 30 mg/kg. Of course, all of these dosages are exemplary, and any dosage in-between these points is also expected to be of use in the invention. Any of the above dosage ranges or dosage levels may be employed for an antagonist of $NC_{Ca-ATP}$ channel or related-compounds thereof.

Administration of the therapeutic antagonist of $NC_{Ca-ATP}$ channel composition of the present invention to a patient or subject will follow general protocols for the administration of therapies used in stroke treatment, such as thrombolytics, taking into account the toxicity, if any, of the antagonist of the $NC_{Ca-ATP}$ channel. It is expected that the treatment cycles would be repeated as necessary. It also is contemplated that various standard therapies, as well as surgical intervention, may be applied in combination with the described therapy.

The treatments may include various "unit doses." Unit dose is defined as containing a predetermined quantity of the therapeutic composition (an antagonist of the $NC_{Ca-ATP}$ channel or its related-compounds thereof) calculated to produce the desired responses in association with its administration, e.g., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time.

B. Combination Treatments

In the context of the present invention, it is contemplated that an antagonist of the $NC_{Ca-ATP}$ channel or related-compounds thereof may be used in combination with an additional therapeutic agent to more effectively treat a cerebral ischemic event, and/or decrease intracranial pressure. In some embodiments, it is contemplated that a conventional therapy or agent, including but not limited to, a pharmacological therapeutic agent may be combined with the antagonist or related-compound of the present invention.

Pharmacological therapeutic agents and methods of administration, dosages, etc. are well known to those of skill in the art (see for example, the "Physicians Desk Reference", Goodman & Gilman's "The Pharmacological Basis of Therapeutics", "Remington's Pharmaceutical Sciences", and "The Merck Index, Eleventh Edition", incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

Non-limiting examples of a pharmacological therapeutic agent that may be used in the present invention include an antihyperlipoproteinemic agent, an antiarteriosclerotic agent, an anticholesterol agent, an antiinflammatory agent, an antithrombotic/fibrinolytic agent, anticoagulant, antiplatelet, vasodilator, and/or diuretics. Thromoblytics that are used can include, but are not limited to prourokinase, streptokinase, and tissue plasminogen activator (tPA) Anticholesterol agents include but are not limited to HMG-CoA Reductase inhibitors, cholesterol absorption inhibitors, bile acid sequestrants, nicotinic acid and derivatives thereof, fibric acid and derivatives thereof. HMG-CoA Reductase inhibitors include statins, for example, but not limited to atoivastatin calcium (Lipitor®), cerivastatin sodium (Baycol®), fluvastatin sodium (Lescol®), lovastatin (Advicor®), pravastatin sodium (Pravachol®), and simvastatin (Zocor®). Agents known to reduce the absorption of ingested cholesterol include, for example, Zetia®. Bile acid sequestrants include, but are not limited to cholestryramine, cholestipol and colesevalam. Other anticholesterol agents include fibric acids and derivatives thereof (e.g., gemfibrozil, fenofibrate and clofibrate); nicotinic acids and derivatives thereof (e.g., nician, lovastatin) and agents that extend the release of nicotinic acid, for example niaspan. Antiinflammatory agents include, but are not limited to non-sterodial anti-inflammatory agents (e.g., naproxen, ibuprofen, celeoxib) and sterodial anti-inflammatory agents (e.g., glucocorticoids). Anticoagulants include, but are not limited to heparin, warfarin, and coumadin. Antiplatelets include, but are not limited to aspirin, and aspirin related-compounds, for example acetaminophen. Diuretics include, but are not limited to such as furosemide (Lasix®), bumetanide (Bumex®), torsemide (Demadex®), thiazide & thiazide-like diuretics (e.g., chlorothiazide (Diuril®) and hydrochlorothiazide (Esidrix®), benzthiazide, cyclothiazide, indapamide, chlorthalidone, bendroflumethizide, metolazone), amiloride, triamterene, and spironolacton. Vasodilators include, but are not limited to nitroglycerin, Thus, in certain embodiments, the present invention comprises co-administration of an antagonist of the $NC_{Ca-ATP}$ channel with a thrombolytic agent. Co-administration of these two compounds will increase the therapeutic window of the thrombolytic agent. Examples of suitable thrombolytic agents that can be employed in the methods and pharmaceutical compositions of this invention are prourokinase, streptokinase, and tissue plasminogen activator (tPA).

In certain embodiments, the present invention comprises co-administration of an antagonist of the $NC_{Ca-ATP}$ channel with glucose or related carbohydrate to maintain appropriate levels of serum glucose. Appropriate levels of blood glucose are within the range of about 60 mmol/l to about 150 mmol/liter. Thus, glucose or a related carbohydrate is administered in combination to maintain the serum glucose within this range.

When an additional therapeutic agent, as long as the dose of the additional therapeutic agent does not exceed previously quoted toxicity levels, the effective amounts of the additional therapeutic agent may simply be defined as that amount effective to reduce cerebral edema when administered to an animal in combination with an agonist of $NC_{Ca-ATP}$ channel or related-compounds thereof. This may be easily determined by monitoring the animal or patient and measuring those physical and biochemical parameters of health and disease that are indicative of the success of a given treatment. Such methods are routine in animal testing and clinical practice.

To inhibit hemorrhagic conversion, reduce cell swelling, etc., using the methods and compositions of the present invention, one would generally contact a cell with antagonist of $NC_{Ca-ATP}$ channel or related-compounds thereof in combination with an additional therapeutic agent, such as tPA, aspirin, statins, diuretics, warfarin, coumadin, mannitol, etc. These compositions would be provided in a combined amount effective to inhibit hemorrhagic conversion, cell swelling and edema. This process may involve contacting the cells with agonist of $NC_{Ca-ATP}$ channel or related-compounds thereof in combination with an additional therapeutic agent or factor(s) at the same time. This may be achieved by contacting the cell with a single composition or pharmacological formulation that includes both agents, or by contacting the cell with two distinct compositions or formulations, at the same time, wherein one composition includes an antagonist of the $NC_{Ca-ATP}$ channel or derivatives thereof and the other includes the additional agent.

Alternatively, treatment with an antagonist of $NC_{Ca-ATP}$ channel or related-compounds thereof may precede or follow the additional agent treatment by intervals ranging from minutes to hours to weeks to months. In embodiments where the additional agent is applied separately to the cell, one would generally ensure that a significant period of time did not expire between the time of each delivery, such that the agent would still be able to exert an advantageously combined effect on the cell. In such instances, it is contemplated that one would contact the cell with both modalities within about 1-24 hr of each other and, more preferably, within about 6-12 hr of each other.

Typically, for maximum benefit of the thrombolytic agent, or therapy must be started within three hours of the onset of stroke symptoms, making rapid diagnosis and differentiation of stroke and stroke type critical. However, in the present invention, administration of the $NC_{Ca-ATP}$ channel with a thrombolytic agent increases this therapeutic window. The therapeutic window for thrombolytic agents may be increased by several (4-8) hours by co-administering antagonist of the $NC_{Ca-ATP}$ channel.

Yet further, the combination of the antagonist and tPA results in a decrease or prevention of hemorrhagic conversion following reperfusion. Hemorrhagic conversion is the transformation of a bland infarct into a hemorrhagic infarct after restoration of circulation. It is generally accepted that these complications of stroke and of reperfusion are attributable to capillary endothelial cell dysfunction that worsens as ischemia progresses. Thus, the present invention is protective of the endothelial cell dysfunction that occurs as a result of an ischemic event.

Endothelial cell dysfunction comprises three phases. Phase one is characterized by formation of ionic edema with the blood brain barrier still intact. The second phase is characterized by formation of vasogenic edema in which the blood brain barrier is no longer intact. Phase three is characterized by hemorrhagic conversion due to failure of capillary integrity during which all constituents of blood, including erythrocytes, extravasate into brain parenchyma. Disruption of BBB involves ischemia-induced activation of endothelial cells that results in expression and release of MMPs, specifically, MMP-2 (gelatinase A) and MMP-9 (gelatinase B).

Since hemorrhagic conversion increases mortality of the patient, it is essential that these patients receive treatment in an urgent manner. For example, it is known that hemorrhagic conversion typically results in patients if reperfusion and tPA treatment is delayed beyond 3 hr or more after thrombotic stroke. Thus, the administration of the antagonist of the present invention will reduce necrotic death of ischemic endothelial cells, and will thereby prolong the therapeutic window for tPA, thereby decreasing mortality of the patient.

VII. Diagnostics

The antagonist or related-compound can be used for diagnosing, monitoring, or prognosis of ischemia or damage to neurons, glial cells or in monitoring neuronal cells in zones of cerebral edema, metastatic tumors, etc.

A. Genetic Diagnosis

One embodiment of the instant invention comprises a method for detecting expression of any portion of a $Na_{Ca-ATP}$ channel, for example, expression of the regulatory unit, SUR1, and/or expression of the pore-forming subunit. This may comprise determining the level of SUR1 expressed and/or the level of the pore-forming subunit expressed. It is understood by the present invention that the up-regulation or increased expression of the $Na_{Ca-ATP}$ channel relates to increased levels of SUR1, which correlates to increased neuronal damage, such as cerebral edema.

Firstly, a biological sample is obtained from a subject. The biological sample may be tissue or fluid. In certain embodiments, the biological sample includes cells from the brain and/or cerebral endothelial cells or microvessels and/or gliotic capsule. For example, in metastatic tumors, glial cells are activated and form a capsule around the tumor.

Nucleic acids used are isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA (cDNA). In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given subject with a statistically significant reference group of normal subjects and subjects that have been diagnosed with a stroke, cancer, cerebral edema, etc.

Yet further, it is contemplated that chip-based DNA technologies such as those described by Hacia et al., (1996) and Shoemaker et al., (1996) can be used for diagnosis. Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization. See also Pease et al., (1994); Fodor et al., (1991).

B. Other Types of Diagnosis

In order to increase the efficacy of molecules, for example, compounds and/or proteins and/or antibodies, as diagnostic agents, it is conventional to link or covalently bind or complex at least one desired molecule or moiety.

Certain examples of conjugates are those conjugates in which the molecule (for example, protein, antibody, and/or compound) is linked to a detectable label. "Detectable labels" are compounds and/or elements that can be detected due to their specific functional properties, and/or chemical characteristics, the use of which allows the antibody to which they are attached to be detected, and/or further quantified if desired.

Conjugates are generally preferred for use as diagnostic agents. Diagnostics generally fall within two classes, those for use in in vitro diagnostics, such as in a variety of immunoassays, and/or those for use in vivo diagnostic protocols, generally known as "molecule-directed imaging".

Many appropriate imaging agents are known in the art, as are methods for their attachment to molecules, for example, antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{11}$carbon, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection.

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of conjugates contemplated in the present invention are those intended primarily for use in vitro, where the molecule is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

The steps of various other useful immunodetection methods have been described in the scientific literature, such as, e.g., Nakamura et al., (1987). Immunoassays, in their most simple and direct sense, are binding assays. Certain preferred immunoassays are the various types of radioimmunoassays (RIA) and immunobead capture assay. Immunohistochemical detection using tissue sections also is particularly useful. However, it will be readily appreciated that detection is not limited to such techniques, and Western blotting, dot blotting, FACS analyses, and the like also may be used in connection with the present invention.

Immunologically-based detection methods for use in conjunction with Western blotting include enzymatically-, radiolabel-, or fluorescently-tagged secondary molecules/antibodies against the SUR1 or regulatory subunit of the $Na_{CaATP}$ channel are considered to be of particular use in this regard. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

In addition to the above imaging techniques, one of skill in the art is also aware that positron emission tomography, PET imaging or a PET scan, can also be used as a diagnostic examination. PET scans involves the acquisition of physiologic images based on the detection of radiation from the emission of positrons. Positrons are tiny particles emitted from a radioactive substance administered to the subject.

Thus, in certain embodiments of the present invention, the antagonist or related-compound thereof is enzymatically-, radiolabel-, or fluorescently-tagged, as described above and used to diagnosis, monitor, and/or stage neuronal damage by cerebral edema. For example, the enzymatically-, radiolabel-, or fluorescently-tagged antagonist or related-compound thereof can be used to determine the size, limits and/or boundaries of tumors. It is difficult to determine the boundaries of certain tumors, for example, metastatic tumors. In metastatic tumors, glial cells are activated and form a capsule or gliotic capsule around the tumor. Thus, the labeled antagonist or related-compound thereof can be used to determine the border of tumor, which can enhance the efficiency of its removal by the surgeon. Still further, the labeled antagonist or related-compound thereof may be used to determine or define the penumbra or the areas at risk for later infarction or damage after a stroke.

VIII. Formulations and Routes for Administration of Compounds

Pharmaceutical compositions of the present invention comprise an effective amount of one or more modulators of $NC_{Ca-ATP}$ channel (antagonist and/or agonist) or related-compounds or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one modulators of $NC_{Ca-ATP}$ channel (antagonist and/or agonist) or related-compounds or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The modulators of $NC_{CaATP}$ channel (antagonist and/or agonist) or related-compounds may comprise different types of carriers depending on whether it is to be administered in solid, liquid or aerosol form, and whether it need to be sterile for such routes of administration as injection. The present invention can be administered intravenously, intradermally, transdermally, intrathecally, intraventricularly, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The modulators of $NC_{Ca-ATP}$ channel (antagonist and/or agonist) or related-compounds may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include modulators of $NC_{CaATP}$ channel (antagonist and/or agonist) or related-compounds, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the modulators of $NC_{CaATP}$ channel (antagonist and/or agonist) or related-compounds may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic and/or prophylatic interventions, idiopathy of the patient and on the route of administration. Depending upon the dosage and the route of administration, the number of administrations of a preferred dosage and/or an effective amount may vary according tot he response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

A. Alimentary Compositions and Formulations

In preferred embodiments of the present invention, the modulators of $NC_{CaATP}$ channel (antagonist and/or agonist) or related-compounds are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof, an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof, a lubricant, such as, for example, magnesium stearate; a sweetening agent, such as, for example, sucrose, lactose, saccharin or combinations thereof, a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, modulators of $NC_{CaATP}$ channel (antagonist and/or agonist) or related-compounds may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intraventricularly, intrathecally, subcutaneous, or intraperitoneally U.S. Pat. Nos. 6,7537,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, DMSO, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the active compound modulators of $NC_{CaATP}$ channel (antagonist and/or agonist) or related-compounds may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

IX. Diagnostic or Therapeutic Kits

Any of the compositions described herein may be comprised in a kit. In a non-limiting example, it is envisioned that a compound that selectively binds to or identifies SUR1 may be comprised in a diagnostic kit. Such compounds can be referred to as an "SUR1 marker", which may include, but are not limited to antibodies (monoclonal or polyclonal), SUR1 oligonucleotides, SUR1 polypeptides, small molecule or combinations thereof, antagonist, agonist, etc. It is envisioned that any of these SUR1 markers may be linked to a radioactive substance and/or a fluorescent marker and/or a enzymatic tag for quick determination. The kits may also comprise, in suitable container means a lipid, and/or an additional agent, for example a radioactive or enzymatic or florescent marker.

The kits may comprise a suitably aliquoted SUR1 marker, lipid and/or additional agent compositions of the present invention, whether labeled or unlabeled, as may be used to prepare a standard curve for a detection assay. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the SUR1 marker, lipid, additional agent, and any other reagent containers in close confinement for commercial sale. Such containers may include injection or blow molded plastic containers into which the desired vials are retained.

Therapeutic kits of the present invention are kits comprising an antagonist, agonist or an related-compound thereof. Depending upon the condition and/or disease that is being treated, the kit may comprise an SUR1 antagonist or related-compound thereof to block and/or inhibit the $NC_{CaATP}$ channel or the kit may comprise an SUR1 agonist or related-compound thereof to open the $NC_{CaATP}$ channel. Such kits will generally contain, in suitable container means, a pharmaceutically acceptable formulation of SUR1 antagonist, agonist or related-compound thereof. The kit may have a single container means, and/or it may have distinct container means for each compound.

When the components of the kit are provided in one and/or more liquid solutions, the liquid solution is an aqueous solution, with a sterile aqueous solution being particularly preferred. The SUR1 antagonist, agonist or related-compounds thereof may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

Examples of aqueous solutions include, but are not limited to ethanol, DMSO and/or Ringer's solution. In certain embodiments, the concentration of DMSO or ethanol that is used is no greater than 0.1% or (1 ml/1000 L).

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the SUR1 antagonist, agonist or related-compounds thereof is suitably allocated. The kits may also comprise a second container means for containing a sterile, pharmaceutically acceptable buffer and/or other diluent.

The kits of the present invention will also typically include a means for containing the vials in close confinement for commercial sale, such as, e.g. injection and/or blow-molded plastic containers into which the desired vials are retained.

Irrespective of the number and/or type of containers, the kits of the invention may also comprise, and/or be packaged with, an instrument for assisting with the injection/administration and/or placement of the SUR1 antagonist, agonist or related-compounds thereof within the body of an animal. Such an instrument may be a syringe, pipette, forceps, and/or any such medically approved delivery vehicle.

In addition to the SUR1 antagonist, agonist or related-compounds thereof, the kits may also include a second active ingredient. Examples of the second active ingredient include substances to prevent hypoglycemia (e.g., glucose, D5W, glucagon, etc.), thrombolytic agents, anticoagulants, antiplatelets, statins, diuretics, vasodilators, etc. These second active ingredients may be combined in the same vial as the SUR1 antagonist, agonist or related-compounds thereof or they may be contained in a separate vial.

Still further, the kits of the present invention can also include glucose testing kits. Thus, the blood glucose of the patient is measured using the glucose testing kit, then the SUR1 antagonist, agonist or related-compounds thereof can be administered to the subject followed by measuring the blood glucose of the patient.

In addition to the above kits, the therapeutic kits of the present invention can be assembled such that an IV bag comprises a septum or chamber which can be opened or broken to release the compound into the IV bag. Another type of kit may include a bolus kit in which the bolus kit comprises a pre-loaded syringe or similar easy to use, rapidly administrable device. An infusion kit may comprise the vials or ampoules and an IV solution (e.g., Ringer's solution) for the vials or ampoules to be added prior to infusion. The infusion kit may also comprise a bolus kit for a bolus/loading dose to be administered to the subject prior, during or after the infusion.

X. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Modulation by Estrogen

A characteristic feature of $K_{ATP}$ channels (Kir6.1, Kir6.2) is that channel affinity for ATP is modulated by the presence of the membrane lipid, $PIP_2$. The open-state stability of $K_{ATP}$ channels is increased by application of $PIP_2$ to the cytoplasmic side of the membrane (Ashcroft, 1998; Baukrowitz et al., 1998; Rohacs et al., 1999). An increase in the open-state stability is manifested as an increase in the channel open probability in the absence of ATP, and in a corresponding decrease in sensitivity to inhibition by ATP (Enkvetchakul et al., 2000; Haruna et al., 2000; Koster et al., 1999; and Larsson et al., 2000).

Figure 1:
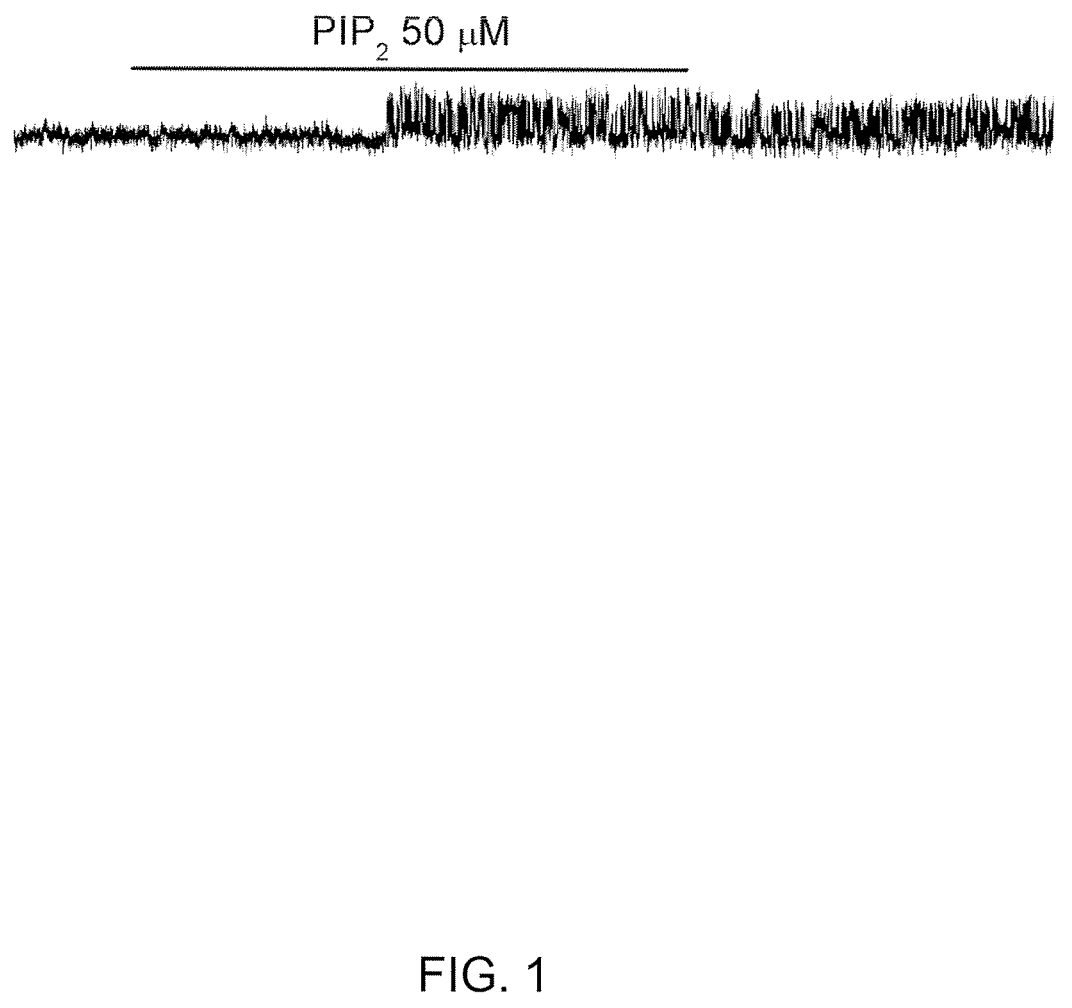

Given the numerous similarities between the $K_{ATP}$ channel and the $NC_{Ca-ATP}$ channel, the inventors postulated that ATP-sensitivity of the $NC_{Ca-ATP}$ channel would respond to $PIP_2$ in the same way. This was tested by studying $NC_{Ca-ATP}$ channels in inside out patches with $Cs^+$ as the charge carrier, and with 1 μM $Ca^{2+}$ and 10 μM ATP in the bath, with the latter expected to fully block the channel. Under these conditions, only the $NC_{Ca-ATP}$ channel was recorded in R1 astrocytes. When $PIP_2$ (50 μM) was added to the bath, channel activity became prominent (FIG. 1), as predicted by analogy to the effect of $PIP_2$ on $K_{ATP}$ channels. This channel activity was blocked by glibenclamide, confirming identity of the channel.

To determine if a receptor-mediated mechanism was involved in the modulation of $NC_{Ca-ATP}$ channel activity, a well known phospholipase C (PLC) was used to study if PLC activation would cause degradation and consumption of $PIP_2$ and thereby increase affinity for ATP, e.g., reduce channel opening. Estrogen is a well known PLC activator in brain as well as elsewhere (Beyer et al., 2002; Le Mellay et al., 1999; Qui et al., 2003). For this experiment, cell attached patches were studied to prevent alteration of intracellular signaling machinery. $NC_{Ca-ATP}$ channel activity was produced by exposure to Na azide to cause depletion of cellular ATP (FIG. 2, initial part of the record).

When estrogen (E2; 10 nM) was applied to the bath, activity due to the $NC_{Ca-ATP}$ channel was soon terminated (FIG. 2). This suggested that estrogen exerted regulatory control over the $NC_{Ca-ATP}$ channel, and suggested that an estrogen receptor capable of rapid (non-genomic) activation of signaling cascades was present on these cells.

Figure 3:
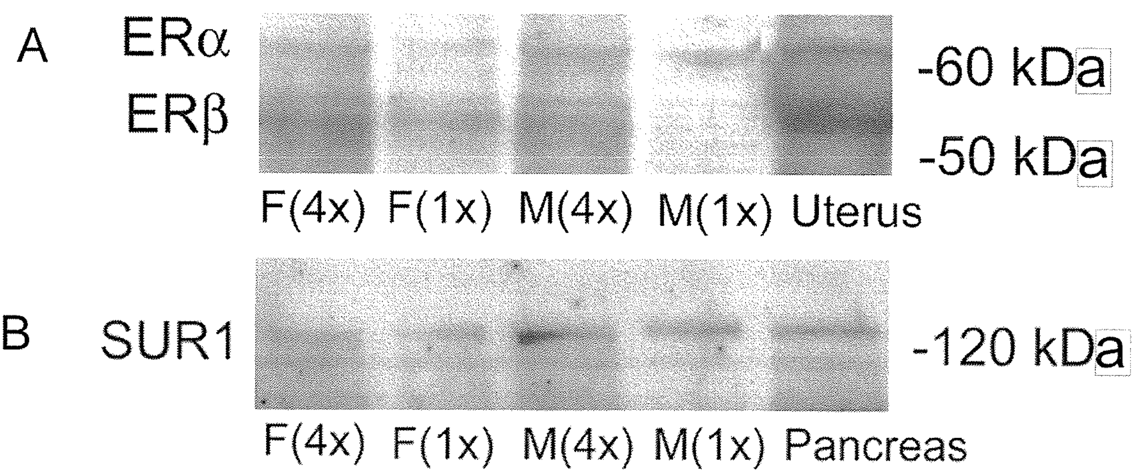
FIGS. 3A-3B show Western blots demonstrating that R1 astrocytes from both males and females express estrogen receptors and SUR1, a marker of the $NC_{Ca\text{-}ATP}$ channel. Cell lysates were obtained from gelatin sponge implants from males (M) and females (F) and studied at two dilutions (4× and 1×), with lysates from uterus used as controls.

Next, to determine whether estrogen receptors could be detected in R1 astrocytes from males and females. Gelatin sponge implants were harvested 7 days after implantation in a group of 3 female rats (F) and another group of 3 male rats (M). Pooled protein from each group was analyzed at 2 dilutions (4×=50 μg total protein; 1×=12.5 μg total protein) by Western blotting, with protein from uterus being used as a control (FIG. 3A). Membranes were blotted with an antibody that recognized both α and β estrogen receptors. Both males and females showed prominent bands at the appropriate molecular weights for the α (66 kDa) and β (55 kDa) receptors (FIG. 3) (Hiroi et al., 1999). The same samples of protein from males and females were also used to confirm presence of SUR1, with protein from pancreas used as a positive control (FIG. 3B). Notably, estrogen receptors have previously been reported in astrocytes from males and females (Choi et al., 2001). In cerebral cortex, the D isoform is reportedly more abundant (Guo et al., 2001) as suggested by the Western blot.

Figure 4:
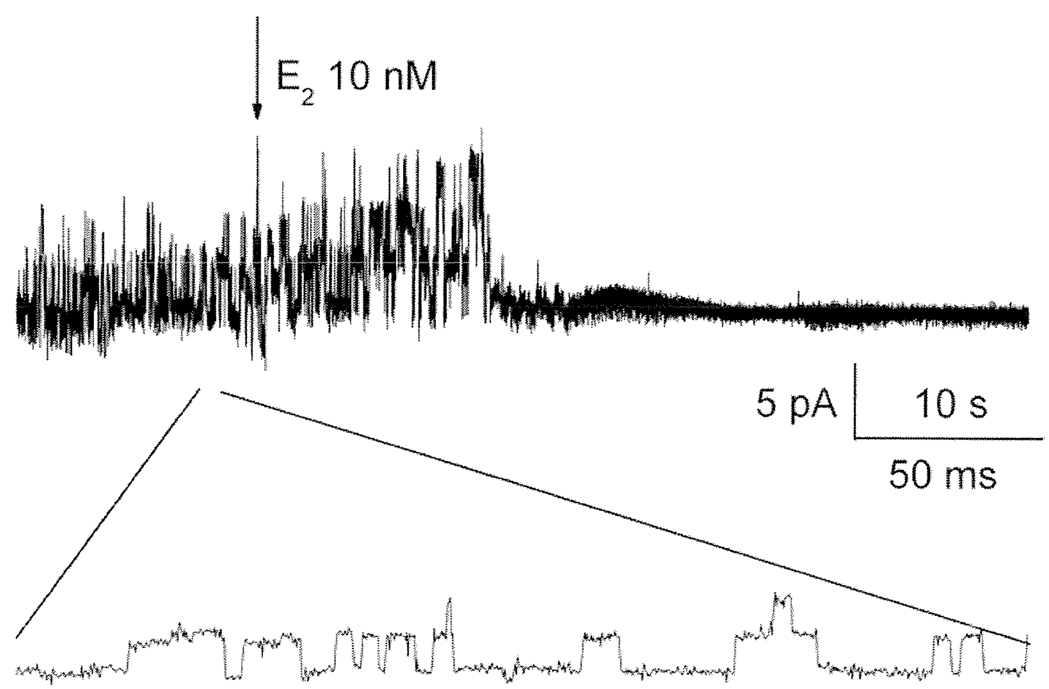
FIG. 4 shows that the $NC_{Ca\text{-}ATP}$ channel in an R1 astrocyte from a male is inhibited by estrogen. The initial portion of the record shows brisk activity from a number of superimposed channels, recorded in a cell attached patch of membrane from an R1 astrocyte obtained from a male. Addition of 10 nM estrogen to the bath promptly resulted in strong inhibition of channel activity.

Next, the electrophysiological experiment of FIG. 2 was repeated using R1 astrocytes harvested from male rats. As above, cell attached patches were studied in which $NC_{Ca-ATP}$ channel activity was activated by depletion of intracellular ATP following exposure to Na azide (FIG. 4A). Examination of the record at higher temporal resolution confirmed activity of a well defined channel of the appropriate conductance for the $NC_{Ca-ATP}$ channel (FIG. 4B). When estrogen was applied to the bath (FIG. 4, E2, 10 nM, arrow), activity due to the $NC_{Ca-ATP}$ channel was quickly terminated (FIG. 4). These data provided further evidence that estrogen exerted regulatory control over the $NC_{Ca-ATP}$ channel, and suggested, in addition, that this response was equally robust in R1 astrocytes from males and females.

By analogy to the effects of estrogen, other mechanisms that deplete $PIP_2$, including other receptor-mediated mechanism as well as more direct activators of PLC such as G-proteins etc., would be expected to have a similar inhibitory effect on activity of the $NC_{Ca-ATP}$ channel and thereby exert a protective effect.

Example 2

The Gliotic Capsule

The standard model involved placing a stab injury into the parietal lobe of an anesthetized rat and implanting a sterile foreign body (gelatin sponge; Gelfoam®) into the stab wound. Variants of the standard model included impregnating the sponge with a substance (e.g., lipopolysaccharide, LPS) or infusing a substance continuously in vivo using an osmotic mini-pump with the delivery catheter placed directly into the sponge. The injury procedure was well tolerated by the animals, with virtually no morbidity or mortality and minimal pain. After an appropriate time in vivo, the whole brain was harvested for histological or immunohistochemical study of tissue sections. Alternatively, if the sponge itself was gently removed from the brain, the inner zone of the gliotic capsule adheres to the sponge and was excised along with it. Thus, the sponge was assayed for protein (e.g., Western) or mRNA (RT-PCR), or it was enzymatically dissociated to yield constituent cells for electrophysiological or other single-cell measurements.

Figure 5:
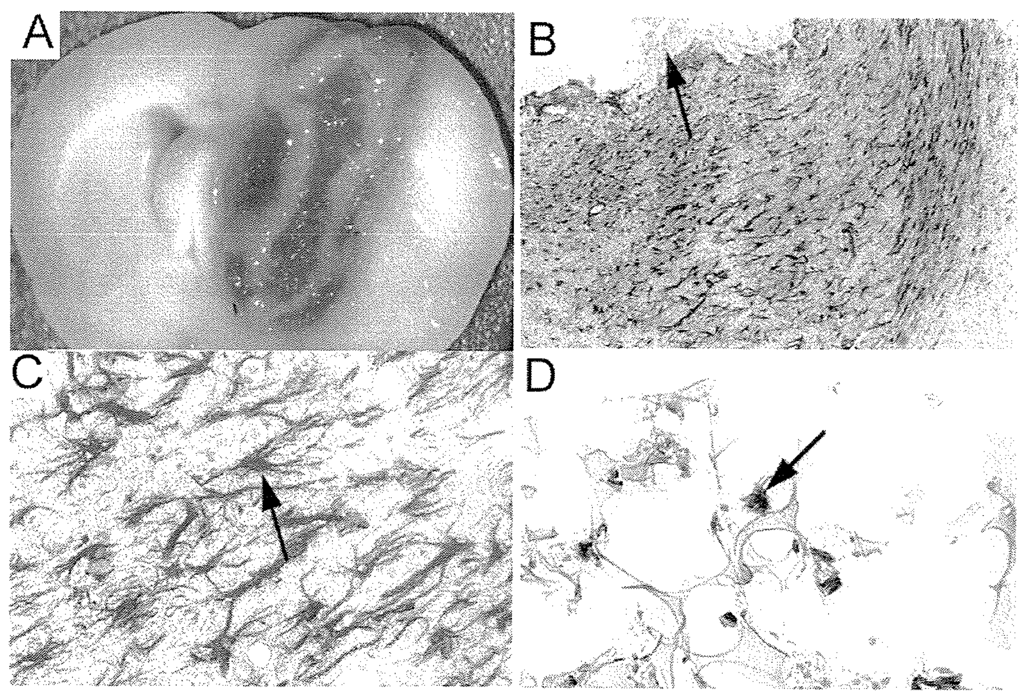
FIGS. 5A-5D shows the gliotic capsule.

The gliotic capsule was well developed 7-10 days after injury. The gliotic capsule was visualized in coronal sections by perfusing the animal with Evans Blue prior to perfusion-fixation of the brain (FIG. 5A). A region of edema (dark) was seen to outline the avascular gliotic capsule (light) that surrounded the gelatin sponge (dark). Immunohistochemical examination with anti-GFAP antibodies showed that the brain parenchyma in the vicinity of the sponge harbors many GFAP-positive reactive astrocytes (FIG. 5B; arrow showed where the gelatin sponge was). At higher power, these intraparenchymal GFAP-positive cells were shown to be large and to bear many prominent cell processes (FIG. 5C, arrow). Examining the gelatin sponge itself showed GFAP-positive reactive astrocytes that migrated into the interstices of the sponge (FIG. 5D, arrow).

Example 3

Isolation of Cells from the Gliotic Capsule

Figure 6:
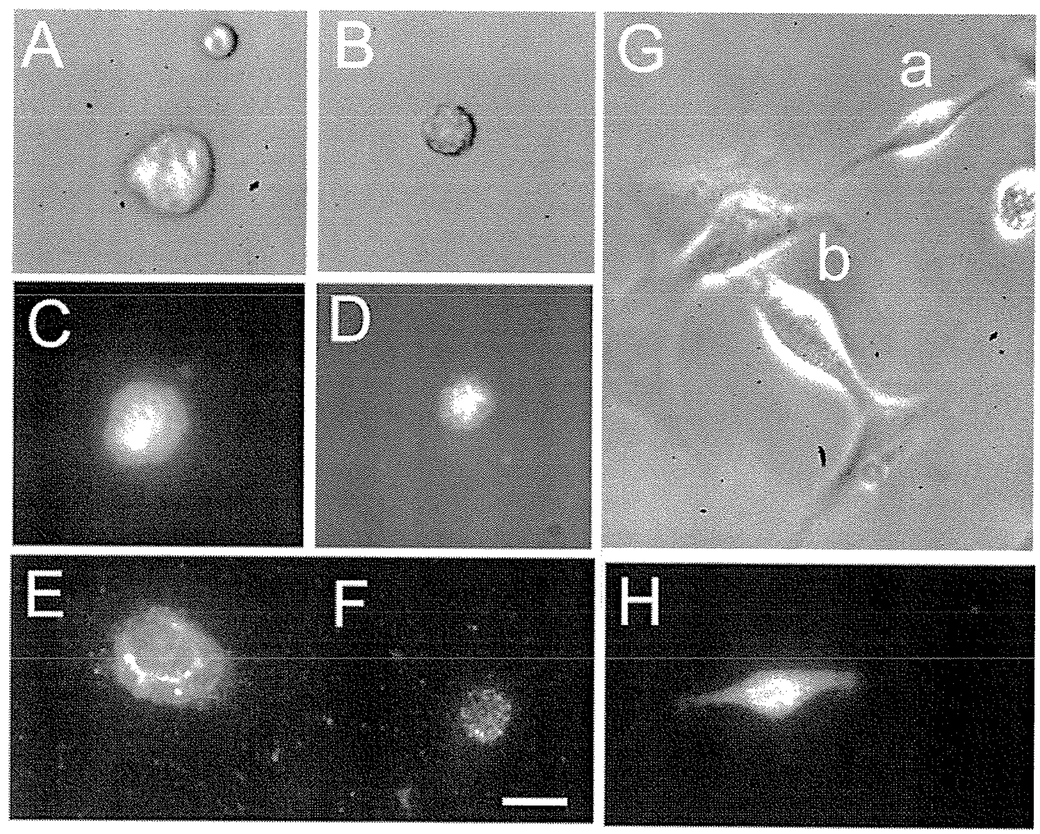
FIGS. 6A-6H show immunolabeled astrocytes.

Phase contrast microscopy of cells freshly isolated by papain digestion of the inner zone of the gliotic capsule and gelatin sponge revealed three types of cells. Most of the cells (>90%) were large, round, have no cell processes and were phase-bright (FIG. 6A). A number of cells (3-5%) were small, round, have no cell processes and were phase-dark (FIG. 6B). Occasionally, a cell was found that was intermediate in size, was phase-bright and had multiple processes that were more than one cell diameter in length (Chen et al., 2003). Immunofluorescence study showed that all of these cells were strongly positive for typical astrocyte markers, including GFAP (FIG. 6C,D) and vimentin (FIG. 6E,F). Microglia were not prominent in the inner zone of the gliotic capsule itself, as indicated by sparse labeling for OX-42. Cells of the inner zone of the gliotic capsule were negative for the O2A progenitor marker, A2B5, and the fibroblast marker, prolyl 4-hydroxylase (Dalton et al., 2003).

As with freshly isolated cells, three morphologically distinct types of cells were observed in primary culture. Most cells (>90%) were large polygonal cells (FIG. 6Gb), a few (3-5%) were small bipolar cells (FIG. 6Ga), and only occasionally were process-bearing stellate-shaped cells observed (Perillan et al., 2000). All of these cells were strongly labeled with anti-GFAP antibodies (FIG. 6H). Experiments in which cells obtained by enzymatic digestion were followed individually in primary culture showed that the large phase-bright cells develop into large polygonal cells (FIG. 6Gb), and the small phase-dark cells developed into small bipolar cells (FIG. 6Ga) (Dalton et al., 2003).

The three morphologically distinguishable types of GFAP-positive astrocytes from the inner zone of the gliotic capsule exhibited very different macroscopic whole cell electrophysiological profiles:

(i) Electrophysiological studies on stellate astrocytes showed that they expressed Kir2.3 and Kir4.1 inward rectifier channels, and immunolabeling experiments suggested that they also expressed $K_{ATP}$ channels comprised of SUR1 and Kir6.1 subunits (Chen et al., 2003; Perillan et al., 2000);

(ii) Electrophysiological studies on R2 astrocytes showed that they expressed a novel $Ca^{2+}$-activated Cl-channel that was sensitive to the polypeptide toxin from the scorpion, *Leiurus quinquestriatus* (Dalton et al., 2003). Only the R2 astrocyte expressed this channel.

(iii) Electrophysiological studies on R1 astrocytes showed that they express Kir2.3 inward rectifier channels that are regulated by TGFβ1 via PKCδ (Perillan et al., 2002; Perillan et al., 2000). When freshly isolated but not after culturing, R1 astrocytes also expressed a novel SUR1-regulated $NC_{Ca-ATP}$ channel (Chen et al., 2003; Chen et al., 2001).

Example 4

Expression of SUR1

Figure 7:
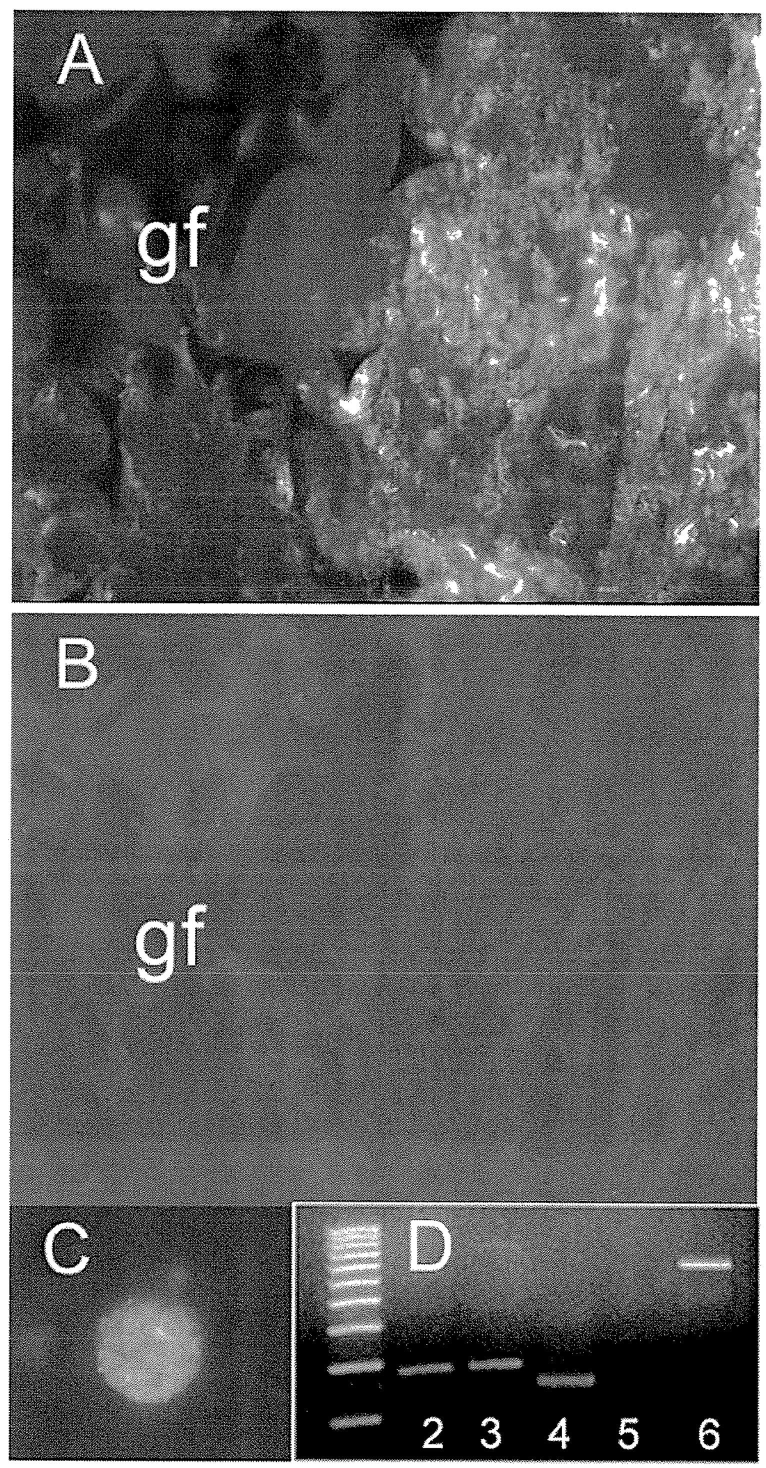
FIGS. 7A-7D show that the inner zone of the gliotic capsule expresses SUR1 but not SUR2. Immunolabling for SUR1 (FIG. 7A) showed prominent expression in cells adjacent to the gelatin sponge (gf), whereas immunolabeling for SUR2 showed no expression (FIG. 7B). A single cell enzymatically isolated from a gelatin sponge implant and immunolabeled for SUR1 is shown (FIG. 7C).

Glibenclamide binds to sulfonylurea receptors, SUR1 and SUR2, with higher affinity for SUR1. Immunofluorescence studies were performed using anti-SURx antibodies. The inner zone of the gliotic capsule immediately outside of the gelatin sponge (gf in FIG. 7) was strongly labeled with anti-SUR1 antibody (FIG. 8A) but not with anti-SUR2 antibody (FIG. 7B). Although individual cells were not discerned at low magnification, higher magnification showed that SUR1 label was uniformly distributed in individual cells after isolation (FIG. 7C).

Evidence for transcription of SUR1, but not SUR2 was also found in RT-PCR experiments run on mRNA from gelatin sponges isolated 7 days after implantation. The signal observed in astrocytes (FIG. 7D, lane 3) was present at the appropriate position on the gel, similar to that from control insulinoma RIN-m5f cells (FIG. 7D, lane 2). By contrast, mRNA for SUR2 is not transcribed in reactive astrocytes (FIG. 7D, lane 5) although it is in cardiomyocytes used as control (FIG. 7D, lane 4).

Example 5

Characterization of the Inner Zone of the Gliotic Capsule

To examine whether or not all GFAP-positive reactive astrocytes in the gliotic capsule are SUR1 positive, brains from rats that had been implanted 1 week earlier with a gelatin sponge, then perfusion-fixed and equilibrated in 40% sucrose in PBS ×2 days were studied. Cryostat sections were double labeled with anti-GFAP and anti-SUR1 antibodies and studied with immunofluorescence. For this and other immunolabeling experiments, standard control protocol included use of the appropriate immunogenic peptide when available or omission of primary antibody.

Five animals were sectioned and imaged with low power images. The images invariably showed that the depth (thickness) of the GFAP response from the edge of the gelatin sponge was several-fold greater than the depth of the SUR1 response. Measurements of the depth of the GFAP response yielded values of about 400-500 μm (FIG. 5A; in FIGS. 8A-8I, the location of the gelatin sponge implant was always to the left; bar in FIG. 8F equals 100 μm). By contrast, the prominent portion of the SUR1 response extended for a depth of only 25-50 μm (FIG. 5D). Outside of the SUR1-positive zone was a wide region of GFAP-positive reactive astrocytes that were mostly SUR1 negative. The SUR1 response was always located precisely at the interface with the foreign body, in the innermost zone of the gliotic capsule. Cells that were SUR1 positive were always GFAP positive. It was evident from this experiment that cells clinging to the gelatin sponge and that were harvested with it were likeliest to express SUR1. Also, it was clear that R1 astrocytes in this innermost region comprised a unique subpopulation of reactive astrocytes. From this observation emerged the concept of the "inner zone" of the gliotic capsule as being a unique entity, distinct from the remainder of the gliotic capsule.

Example 6

Other Characteristics of the Inner Zone of the Gliotic Capsule

Other studies were performed to further evaluate the inner zone of the gliotic capsule. In previous experiments, it was found that primary culture of R1 astrocytes under normoxic culture conditions resulted in loss of the SUR1-regulated $NC_{Ca-ATP}$ channel after 3 days, whereas cultured under hypoxic conditions resulted in continued expression of the channel (Chen et al., 2003). Thus, it was determined that expression of the channel required hypoxic conditions, and thus the inner zone of the gliotic capsule where SUR1 expressing R1 astrocytes were found might also be hypoxic. To evaluate this, the histochemical marker, pimonidazole, was used which at $pO_2<10$ mm Hg, forms irreversible covalent adducts with cellular proteins that can be detected immunohistochemically (Arteel et al, 1998; Hale et al., 2002; Kennedy et al., 1997).

Briefly, rats were prepared with a stab injury and implantation of a gelatin sponge. Rats were allowed to survive 1 week. Pimonidazole was administered prior to death, and cryosections were processed for immunofluorescence study using the appropriate antibody to detect pimonidazole adducts. Cryosections were double labeled for GFAP. This experiment confirmed the presence of hypoxic conditions restricted to the SUR1-positive inner zone of the gliotic capsule, with the most prominent pimonidazole labeling extending only 20-50 μm deep (FIG. 8B; GFAP not shown but the depth of the GFAP response resembled that in FIG. 8A). High resolution imaging showed that pimonidazole labeling (FIG. 5G, upper right) was present in large GFAP-positive astrocytes (FIG. 5G, lower left).

Figure 8:
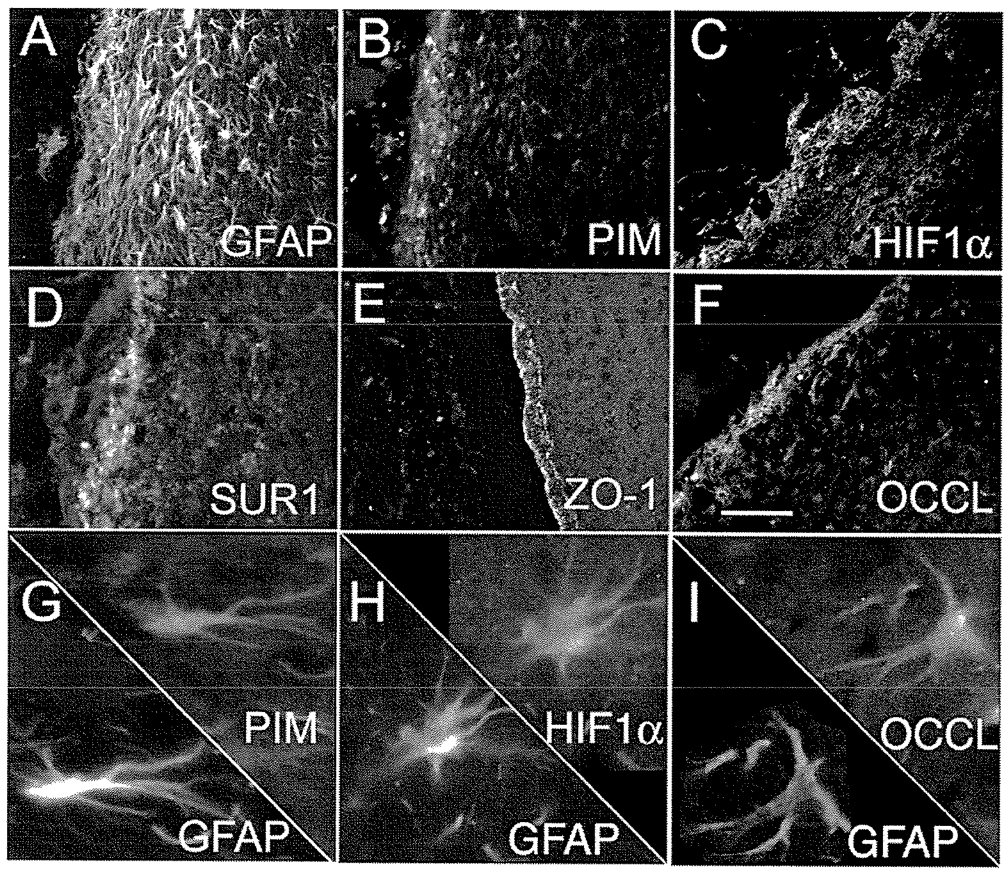
FIGS. 8A-8I show various features of the gliotic capsule. The gliotic capsule is characterized by GFAP-positive cells that are several cell-layers thick (FIG. 8A). Only the inner zone of the gliotic capsule is hypoxic, as demonstrated by pimonidozole labeling (FIG. 8B) and by immunolabeling for HIF1α (FIG. 8C). Also, only the inner zone is immunolabeled for SUR1 (FIG. 8D), and for the tight junction proteins, ZO-1 (FIG. 8E) and occludens (FIG. 8F).

It was reasoned that hypoxia of the inner zone might lead to up-regulation/activation of the hypoxia-responsive transcription factor, HIF-1. To examine this, immunolabeling was performed of sections with anti-HIF-1α antibodies with co-labeling for GFAP. This experiment confirmed that HIF-1α labeling was mostly restricted to the SUR1-positive inner zone of the gliotic capsule, with labeling extending only 20-50 μm deep (FIG. 8C; GFAP not shown but the depth of the GFAP response resembled that in FIG. 5A). High resolution imaging showed that HIF-1α labeling (FIG. 8H, upper right) was present in large GFAP-positive astrocytes (FIG. 8H, lower left).

Expression of tight junction proteins was also examined. Two tight junction proteins, ZO-1 and occludin-5, were studied, labeling alternate cryosections with antibodies directed against these proteins. Sections were double labeled for GFAP. Again, only the innermost layer 20-50 μm deep was labeled for either ZO-1 or occludin-5 (FIGS. 8E and 8F; GFAP not shown but the depth of the GFAP response resembled that in FIG. 8A). High resolution imaging showed that occludin-5 labeling (FIG. 8I, upper right) was present in large GFAP-positive astrocytes (FIG. 8I, lower left).

Thus, the inner zone of the gliotic capsule, with its R1 astrocytes that express SUR1-regulated $NC_{Ca-ATP}$ channels and tight junction proteins, may be acting as an important barrier between the foreign body and the brain, e.g., a foreign body-brain barrier (FbBB). If true, one would expect that breaching the barrier might significantly affect the overall response to injury.

Example 7

Manipulation of the Inner Zone

Rats were prepared with a stab injury and implantation of a gelatin sponge according to our usual protocol and were allowed to survive 1 week. At time of surgery, rats were also implanted with osmotic mini-pumps subcutaneously with the delivery catheter placed in the brain at the site of injury. Animals received pumps with either glibenclamide (1 μM at 0.5 μl/hr×7 days) or diazoxide (10 μM at 0.5 μl/hr×7 days). No systemic toxicity was observed, neurological behavior was not impaired, and animals appeared healthy and were not febrile.

Figure 9:
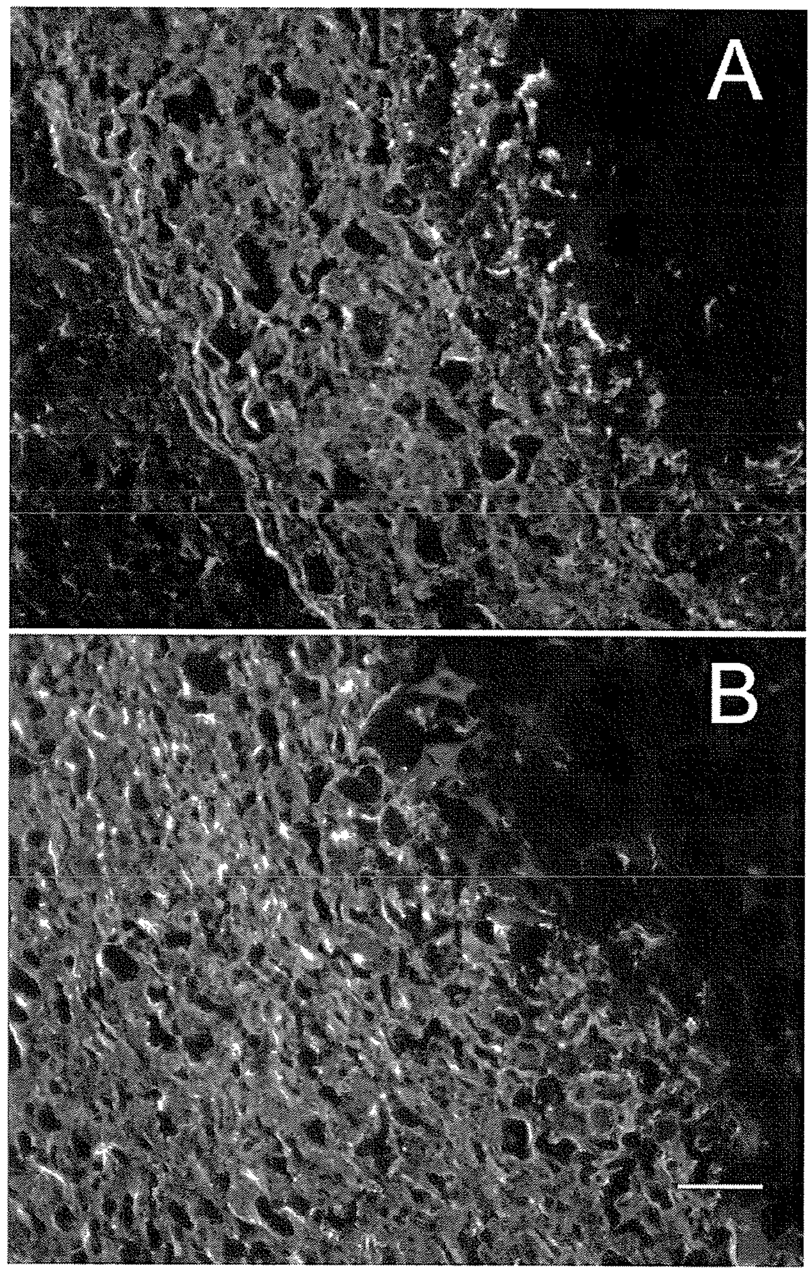

Cryosections of injured brains were examined for GFAP. In animals receiving glibenclamide, a well defined gliotic capsule was visualized that was sharply demarcated from surrounding brain, with the inner zone appearing to be densely populated by GFAP-positive cells (FIG. 9A; gelatin sponge to the right). By contrast, animals receiving diazoxide showed an expanded GFAP-positive response that extended farther from the foreign body, with an outer region that was poorly demarcated, and an inner zone that was loose and not compact (FIG. 9B; gelatin sponge to the right).

Figure 10:
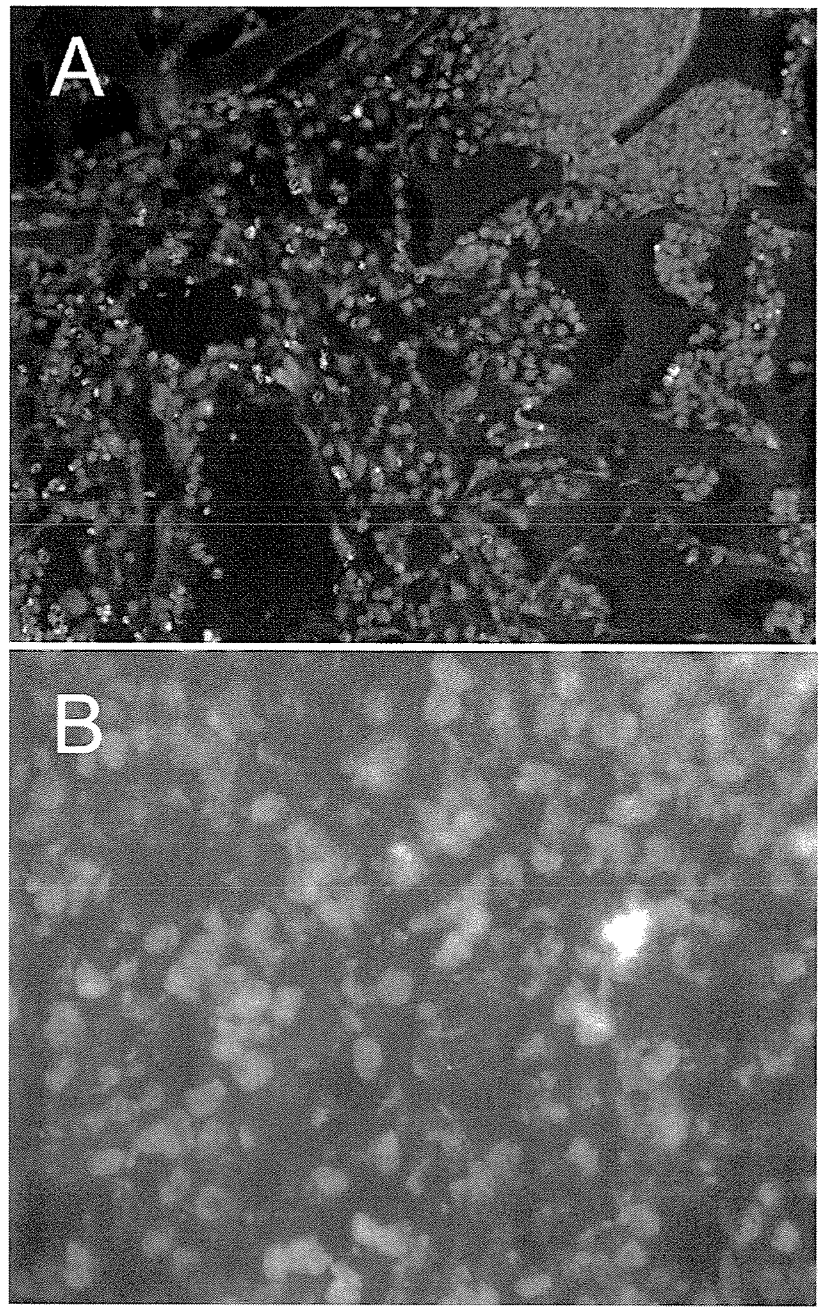
FIGS. 10A-B show that infusion of diazoxide into the area around the gelatin sponge resulted in a heavy infiltration of polymorphonuclear leukocytes (PMNs). Nuclear labeling with DAPI showed densely packed small cells in the vicinity of the gelatin sponge (FIG. 10A), with immunolabeling using the PMN-specific marker, MMP-8, demonstrating that these cells were PMNs (FIG. 10B). It is believed that the strong inflammatory response represented by the infiltrating PMNs was due to disruption of the barrier between brain and foreign body (gelatin sponge) normally formed by the inner zone of the gliotic capsule.

Cryosections were also examined with the nuclear label, DAPI. In sections from glibenclamide-treated animals, most of the labeling was attributable to GFAP-positive astrocytes. However, in sections from diazoxide-treated animals, DAPI labeling showed "sheets" of small nucleated cells (dull spots in FIG. 10A). On inspection, these sheets of cells appeared to be polymorphonuclear leukocytes (PMNs, neutrophils). This was confirmed by labeling with MMP-8, a PMN-specific marker (FIG. 10B). It is important to note that no evidence of infection was present, and microbiological cultures of explanted materials showed no bacterial growth, including aerobic and anaerobic cultures, indicating that the inflammatory response was not due to infection.

Thus, protecting inner zone R1 astrocytes with glibenclamide appeared to have restrained the overall GFAP-response to injury, whereas killing inner zone R1 astrocytes with diazoxide appeared to have caused an expansion of the overall GFAP-response and recruitment of tremendous numbers of neutrophils. These observations strongly reinforced the concept of the "inner zone" of the gliotic capsule as being a unique entity, with a critical function in determining the overall response to injury.

Example 8

SUR1 in Multiple Brain Pathologies

Figure 11:
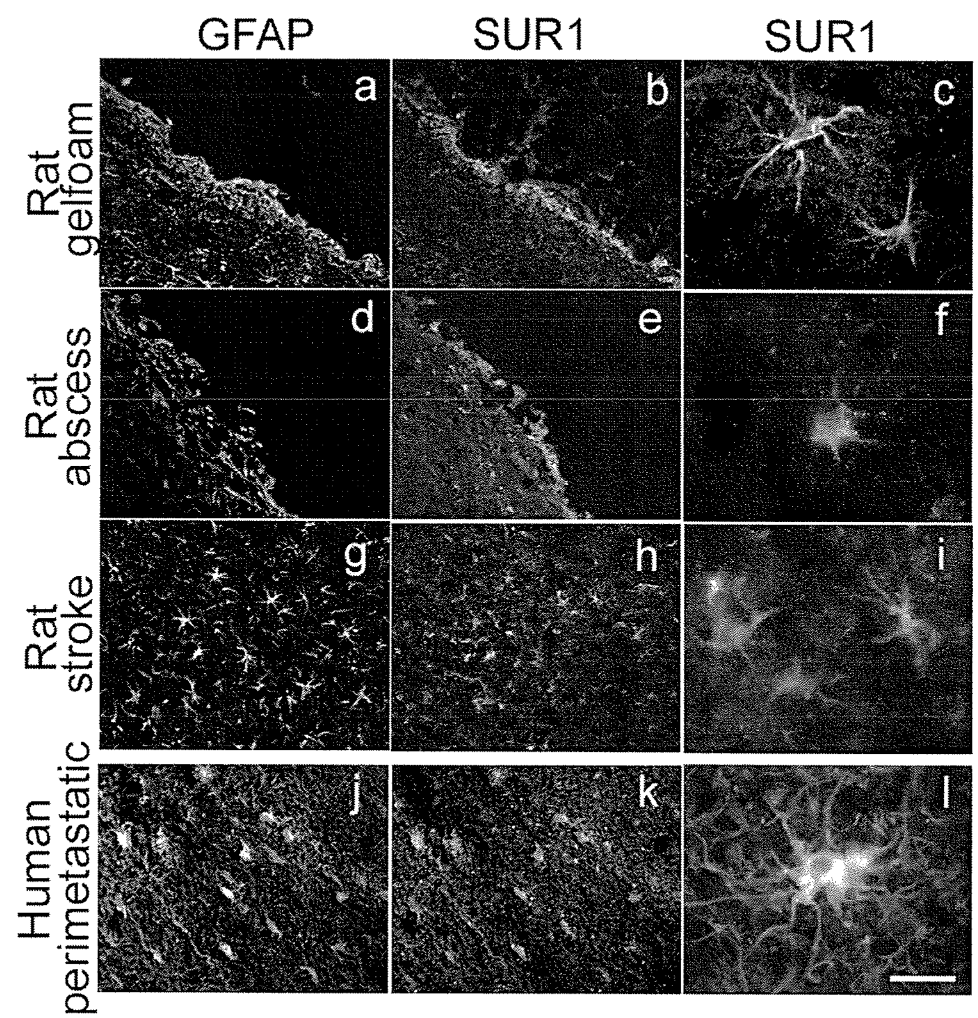
FIGS. 11A-11L show that R1 astrocytes in the inner zone of the gliotic capsule typically express SUR1, a marker for the $NC_{CaATP}$ channel. The inner zones of the gliotic capsules in rats with gelatin sponge implants (FIGS. 11A-11C), in rats with cerebral abscess (FIGS. 11D-11F), and in humans with metastatic tumor (FIGS. 11J-11L) are shown. Also shown is the area of reactive gloss adjacent to a stroke in the rat (FIGS. 11G-11I) resulting from occlusion of the middle cerebral artery. In all cases, a field of cells is labeled for GFAP and co-labelled for SUR1, as indicated. Examples of single cells at high power are also shown for each condition.

Tissues were obtained from the 3 rat models (trauma, abscess and stroke) and from human metastatic tumor, and double immunolabeling was performed with antibodies directed against GFAP and SUR1. Low power views showed a layer of tissue adjacent to the gelatin sponge implant with positive immunolabeling for GFAP that coincided with positive immunolabeling for SUR1 (FIG. 11A,B). Examination of individual cells at high power showed that the SUR1 immunolabel was present in large stellate-shaped astrocytes, confirming the presence of SUR1-positive R1 astrocytes in the inner zone of the gliotic capsule surrounding a foreign body implant (FIG. 11C).

A brain abscess model in the rat was studied. The abscess was produced by implanting an autologous fecal pellet subcortically under general anesthesia. These animals survived quite well, although they showed evidence of mild weight loss. When sacrificed 1 week after surgery, a purulent cavity was found surrounded by a gliotic capsule. Low power views of the gliotic capsule adjacent to the area of puss showed cells with positive immunolabeling for GFAP that coincided with positive immunolabeling for SUR1 (FIG. 1D,E). Examination of individual cells at high power showed that the SUR1 immunolabel was present in large stellate-shaped astrocytes, confirming the presence of SUR1-positive R1 astrocytes in the inner zone of the gliotic capsule surrounding brain abscess (FIG. 11F).

A standard stoke model in the rat was studied. The stroke was produced by intra-carotid insertion of a thread up to the bifurcation of the internal carotid artery, placed under general anesthesia. Animals surviving the stroke were sacrificed at 1 week and the brain was examined. Low power views of tissues adjacent to the area of stroke showed cells with positive immunolabeling for GFAP that coincided with positive immunolabeling for SUR1 (FIG. 11G,H). Examination of individual cells at high power showed that the SUR1 immunolabel was present in large stellate-shaped astrocytes, confirming the presence of SUR1-positive R1 astrocytes in the gliotic capsule surrounding stroke (FIG. 11I).

Tissue was obtained from humans undergoing surgery for resection of metastatic brain tumors. At surgery, the gliotic capsule that surrounds the metastasis is readily distinguished from the tumor itself and from edematous white matter. Low power views of the gliotic capsule adjacent to the metastasis showed cells with positive immunolabeling for GFAP that coincided with positive immunolabeling for SUR1 (FIG. 11J,K). Examination of individual cells at high power showed that the SUR1 immunolabel was present in large stellate-shaped astrocytes with multiple well-developed processes, confirming the presence of SUR1-positive R1 astrocytes in the gliotic capsule surrounding metastatic brain tumor in humans (FIG. 11L).

These data show for the first time SUR1 up-regulation in reactive astrocytes at the site of formation of a gliotic capsule consistent with expression of SUR1-regulated $NC_{Ca-ATP}$ channels in R1 astrocytes. The data indicate that SUR1 expression in R1 astrocytes in the gliotic capsule was a common phenomenon in numerous pathological conditions that affect the brain. These data highlight a unique opportunity to manipulate R1 astrocytes of the inner zone selectively by exploiting pharmacological agents that act at SUR1 and that can therefore determine death or survival of these cells.

Overall, these observations strongly reinforced the concept of the "inner zone" of the gliotic capsule as being a unique entity, distinct from the remainder of the gliotic capsule.

Example 9

Figure 12:
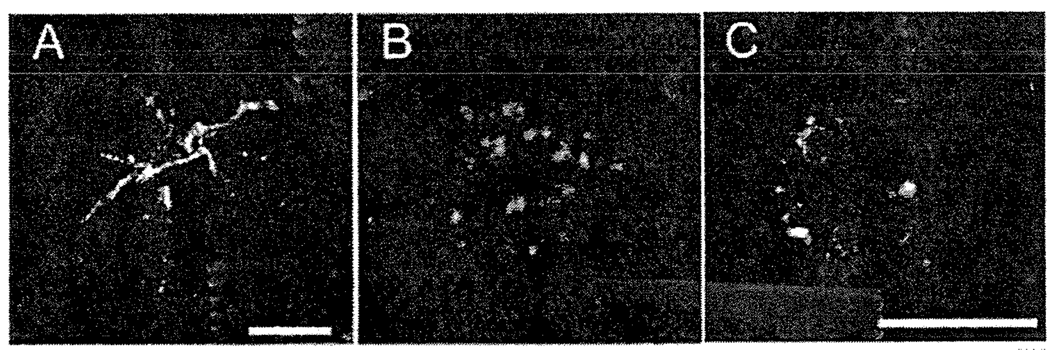
FIGS. 12A-12C shows that stellate astrocytes near the edge of a stroke up-regulate SUR1 (FIG. 12A), a marker of the $NC_{Ca\text{-}ATP}$ channel. In the middle of the stroke, cells with altered morphology including blebbing are also immunolabeled for SUR1 (FIG. 12B,12C).
Figure 13:
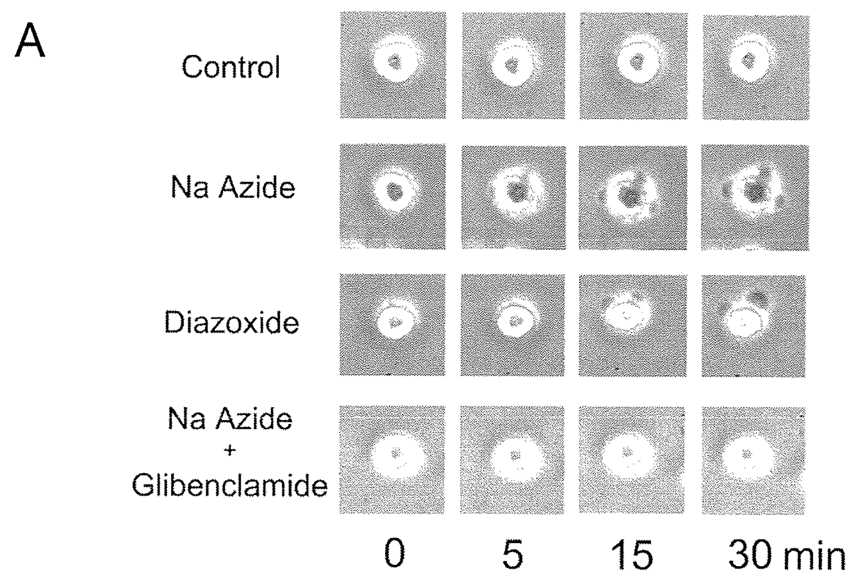
FIGS. 13A-13C show that glibenclamide protects from Na azide-induced channel opening and necrotic cell death.
Figure 13:
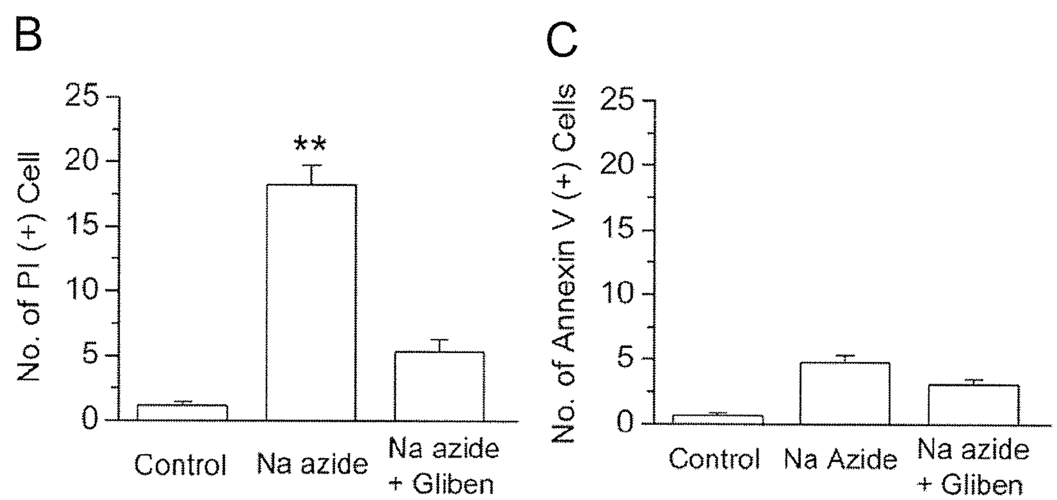

The $NC_{CaATP}$ Channel and Necrotic Death $NC_{Ca-ATP}$ channels were studied in a rodent model of stroke. In the penumbra, SUR1 labeling was found in stellate-shaped cells (FIG. 12A) that were also GFAP-positive. In the middle of the stroke, stellate cells were absent, but SUR1 labeling was found in round cells exhibiting a bleb-like appearance (FIG. 12B,C) that were also GFAP-positive (not shown). The round cells with blebbing in situ resembled reactive astrocytes in vitro undergoing necrotic death after exposure to Na azide. The effect of glibenclamide vs. saline was determined. Glibenclamide or saline was administered via subcutaneously-implanted osmotic mini-pump (1 μM at 0.5 μl/hr). In saline treated rats, 3-day mortality after stroke was 68%, whereas in glibenclamide-treated rats, 3-day mortality was reduced to 28% (n=29 in each group; p<0.001, by $\chi^2$). In separate animals, the stroke hemisphere in glibenclamide-treated rats contained only half as much excess water as in saline-treated rats (n=5 in each group; p<0.01, by t-test), confirming an important role of the $NC_{Ca-ATP}$ channel in edema formation.

SUR1 was also studied in a rodent model of trauma. The effect of direct infusion of drugs into the site of trauma was examined using an implanted osmotic mini-pump. The channel inhibitor, glibenclamide, was used to reduce death of reactive astrocytes, and the channel activator, diazoxide, to promote astrocyte death. Glibenclamide infusion reduced the overall injury response, stabilized the gliotic capsule around the foreign body implant, and minimized the inflammatory response compared to control.

Conversely, diazoxide essentially destroyed the gliotic capsule and incited a huge inflammatory response, characterized by massive influx of polymorphonuclear cells (PMNs) (FIG. 10A, B). These data suggested that $NC_{Ca-ATP}$ channel plays a critical role in the injury response, and they strongly support the hypothesis that inflammation is closely linked to activity of the $NC_{Ca-ATP}$ channel and necrotic death of reactive astrocytes.

Example 10

Permanent MCA Models

Adult male or female Wistar rats (275-350 gm) were fasted overnight then anesthetized (Ketamine, 60 mg/kg plus Xylazine, 7.5 mg/kg, i.p.). The right femoral artery was cannulated, and physiological parameters, including temperature, pH, $pO_2$, $pCO_2$ and glucose were monitored. Using a ventral cervical incision, the right external carotid and pterygopalatine arteries were ligated. The common carotid artery was ligated proximally and catheterized to allow embolization of the internal carotid artery.

For thromboembolic (TE) stroke, 7-8 allogeneic clots, 1.5 mm long, were embolized. Allogeneic, thrombin-induced, fibrin-rich blood clots were prepared (Toomy et al., 2002).

For large MCA strokes with malignant cerebral edema (MCE), the inventors first embolized microparticles (Nakabayashi et al., 1997) [polyvinyl alcohol (PVA) particles; Target Therapeutics, Fremont Calif.; 150-250 μm diameter, 600 μg in 1.5 ml hepaninized-saline], followed by standard permanent intraluminal suture occlusion (Kawamura et al., 1991) using a monofilament suture (4-0 nylon, rounded at the tip and coated with poly-L-lysine) advanced up to the ICA bifurcation and secured in place with a ligature.

After stroke, animals are given 10 ml glucose-free normal saline by dermoclysis. Rectal temperature was maintained at 37° C. using a servo-controlled warming blanket until animals awoke from anesthesia. Blood gases and serum glucose at the time of stroke were: $pO_2$, 94±5 mm Hg; $pCO_2$, 36±5 mm Hg; pH, 7.33±0.01; glucose 142±6 mg/dl in controls and $PO_2$, 93±3 mm Hg; $pCO_2$, 38±2 mm Hg; pH, 7.34±0.01; glucose 152±7 mg/dl in glibenclamide-treated animals.

With both models, animals awoke promptly from anesthesia and moved about, generally exhibited abnormal neurological function, typically circling behavior and hemiparesis. Mortality with the thromboembolic (TE) model was minimal, whereas with the malignant cerebral edema (MCE) model, animals exhibited delayed deterioration, often leading to death. Most deaths occurred 12-24 hr after MCA occlusion, with necropsies confirming that death was due to bland infarcts. Rarely, an animal died <6 hr after stroke and was found at necropsy to have a subarachnoid hemorrhage, in which case it was excluded from the study. Mortality in untreated animals with MCE and bland infarcts was 65%, similar to that in humans with large MCA strokes (Ayata & Ropper, 2002).

Example 11

Studies on Stroke Size, Mortality, Tissue-Water, and Drug Localization

After MCA occlusion (both TE and MCE models), mini-osmotic pumps (Alzet 2002, Durect Corporation, Cupertino, Calif.) were implanted subcutaneously that delivered either saline or glibenclamide (Sigma, St. Louis, Mo.; 300 μM or 148 μg/ml, 0.5 μl/hr subcutaneously, no loading dose). Stroke size (TE model), measured as the volume of TTC(−) tissue in consecutive 2 mm thick slices and expressed as the percent of hemisphere volume, was compared 48 after stroke in 2 treatment groups, each comprised of 10 male rats, treated with either saline or glibenclamide. Mortality (MCE model) was compared during the first week after stroke in 2 treatment groups, each comprised of 29 rats (19 female plus 10 male), treated with either saline or glibenclamide. Edema (MCE model) was compared at 8 hr after stroke in 2 treatment groups, each comprised of 11 male rats, treated with either saline or glibenclamide; rats in each of these 2 treatment groups were subdivided into 2 subgroups, with the first of these being used to analyze water in the entire involved hemisphere (no TTC processing), and the second being used to analyze water in the TTC(+) vs. TTC(−) portions of the involved hemisphere. For localization of fluorescent-tagged drug, 20 male rats were subjected to MCA stroke (MCE model) and were implanted with mini-osmotic pumps that delivered BODIPY-conjugated glibenclamide (BODIPY-FL-glyburide, Molecular Probes, Eugene, Oreg.; 300 μM or 235 μg/ml, 0.5 μl/hr subcutaneously, no loading dose). Of these, 15 rats were used for validation of drug action (mortality, tissue water and glucose) and 5 rats were used for determination of drug distribution.

Example 12

Immunolabeling

Brains were perfusion-fixed (4% paraformaldehyde) and cryoprotected (30% sucrose). Cryosections (10 μm) were prepared and immunolabeled using standard techniques (Chen et al., 2003). After permeabilizing (0.3% Triton X-100 for 10 min), sections were blocked (2% donkey serum for 1 hr; Sigma D-9663), then incubated with primary antibody directed against SUR1 (1:300; 1 hr at room temperature then 48 h at 4° C.; SC-5789; Santa Cruz Biotechnology). After washing, sections were incubated with fluorescent secondary antibody (1:400; donkey anti-goat Alexa Fluor 555; Molecular Probes, OR). For co-labeling, primary antibodies directed against NeuN (1:100; MAB377; Chemicon, CA); GFAP (1:500; CY3 conjugated; C-9205; Sigma, St. Louis, Mo.) and vWf (1:200; F3520, Sigma) were used and tissues were processed according to manufacturers' recommendations. Species-appropriate fluorescent secondary antibodies were used as needed. Fluorescent signals were visualized using epifluorescence microscopy (Nikon Eclipse E1000).

Example 13

TTC Staining, Stroke Size

Freshly harvested brains were cut into 2-mm thick coronal sections, and slices were exposed to TTC (0.125% w/v in 62.5 mM Tris-HCl, 13 mM $MgCl_2$, 1.5% dimethylformamide) for 30 min at 37° C. For stroke size, stained sections were photographed and images were analyzed (Scion Image) to determine the percent of the involved hemisphere occupied by TTC(−) tissue; no correction for edema was performed. For some determinations of water or SUR1 protein content, individual coronal sections were divided under magnification into 3 parts: (i) the non-involved, control hemisphere; (ii) the TTC(+) portion of the involved hemisphere; (iii) the TTC(−) portion of the involved hemisphere. For each animal, pooled tissues from the 3 parts were then processed for tissue water measurements or for Western blots.

Example 14

Tissue Water Content

Tissue water was quantified by the wet/dry weight method (Hua et al., 2003). Tissue samples were blotted to remove small quantities of adsorbed fluid. Samples were weighed with a precision scale to obtain the wet weight (WW), dried to constant weight at 80° C. and low vacuum, and then reweighed to obtain the dry weight (WD). The percent $H_2O$ of each tissue sample was then calculated as (WW-WD)×100/WW.

Example 15

Immunoblots

Tissues lysates and gels were prepared (Perillan et al., 2002). Membranes were developed for SUR1 (SC-5789; Santa Cruz Biotechnology), Kir6.1 (Santa Cruz) or Kir6.2 (Santa Cruz). Membranes were stripped and re-blotted for β-actin (1:5000; Sigma, St. Louis, Mo.), which was used to normalize the primary data. Detection was carried out using the ECL system (Amersham Biosciences, Inc.) with routine imaging and quantification (Fuji LAS-3000).

Example 16

In Situ Hybridization

Non-radioactive digoxigenin-labeled probes were made according to the manufacturer's protocol (Roche) using SP6 or T7 RNA polymerase. RNA dig-labeled probes (sense and anti-sense) were generated from pGEM-T easy plasmids (Promega) with the SUR1 insert (613 bp) flanked by the primers: 5' AAGCACGTCAACGCCCT 3' (SEQ ID NO: 1) (forward); 5' GAAGCTTTTCCGGCTTGTC 3' (SEQ ID NO: 2) (reverse). Fresh-frozen (10 μm) or paraffin-embedded (4 μm) sections of rat brain (3, 6, 8 hours after MCA stroke) were used for in situ hybridization (Anisimov et al., 2002).

Example 17

Inner Zone of the Gliotic Capsule

To assess if other causes of hypoxia, for example arterial occlusion, resulted in up-regulation of SUR1, two rodent models of permanent focal cerebral ischemia described in Example 10 were used.

The MCE model was used to evaluate SUR1 protein and mRNA, and to assess effects of SUR1 inhibition on edema and survival, while the TE model was used to measure effects of SUR1 inhibition on stroke size. Absence of perfusion (FIG. 14A), TTC staining (Mathews et al., 2000) (FIG. 14B) and GFAP immunolabeling were used to distinguish infarct from peri-infarct regions.

Figure 14:
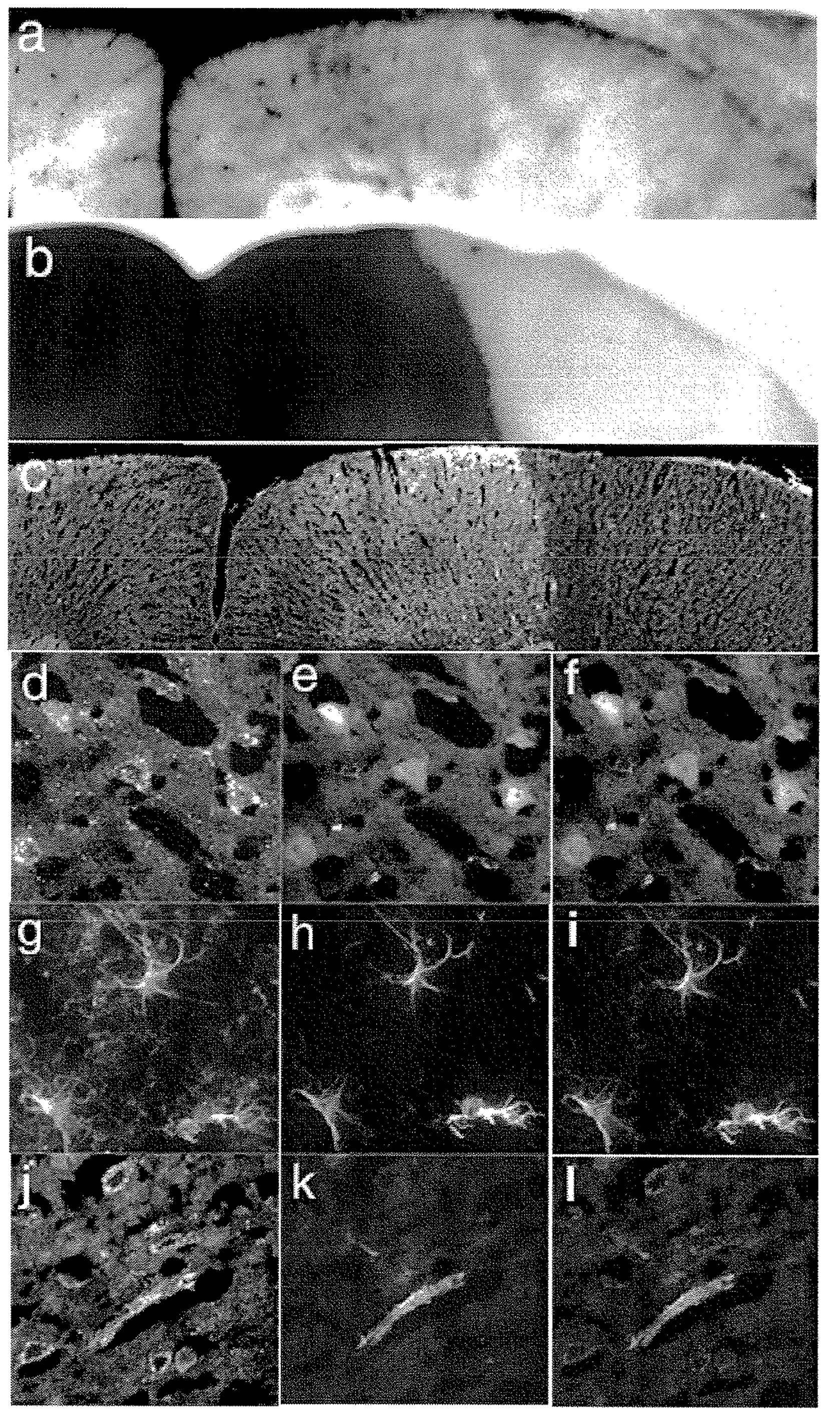
FIG. 14A-14L shows that SUR1 is up-regulated in MCA stroke. Watershed area between MCA-ACA in 3 different animals 8-16 hr after MCA stroke, identified by pre-mortem administration of Evans blue and postmortem perfusion with India ink (FIG. 14A), by TTC staining (FIG. 14B) and by immunofluorescence imaging for SUR1 (FIG. 14C). Immunofluorescence images showing SUR1 at 3 hr in the core of the stroke in cells (FIG. 14D) double-labeled for the neuronal marker, NeuN (FIG. 14E), and showing SUR1 at 8 hr in the peri-infarct region in cells (FIG. 14G, 14J) double-labeled for the astrocytic marker, GFAP (FIG. 14H), and the endothelial cell marker, von Willebrand factor (FIG. 14K). Superimposed images of double-labeled fields are shown (FIGS. 14F, 14I, and 14L).

SUR1 expression increased transiently in the core of the infarct. Here, an increase in SUR1 became evident as early as 2-3 hr after MCA occlusion (FIG. 14D), well before onset of necrosis, and later disappeared as necrosis set in (FIG. 14C, right side of figure). At these early times before necrosis, SUR1 was very prominent in neurons that co-labeled with NeuN (FIG. 14D-F).

In peri-infarct regions, including the classical ischemic "watershed" zone between anterior cerebral artery (ACA) and MCA territories, SUR1 expression increased later than in the core but was sustained. By 6-12 hr, SUR1 expression sharply demarcated infarct and peri-infarct areas (FIG. 14C). Here, SUR1 expression was found in neurons, astrocytes and capillary endothelial cells, as shown by co-labeling with NeuN, GFAP (FIG. 14G-I) and von Willebrand factor (FIG. 14J-L), respectively. SUR1 is not normally expressed in such abundance in these cortical and subcortical areas (Treherne & Ashford, 1991; Karschin et al., 1997) as is evident in contralateral tissues (FIG. 14C, left side of figure).

Figure 15:
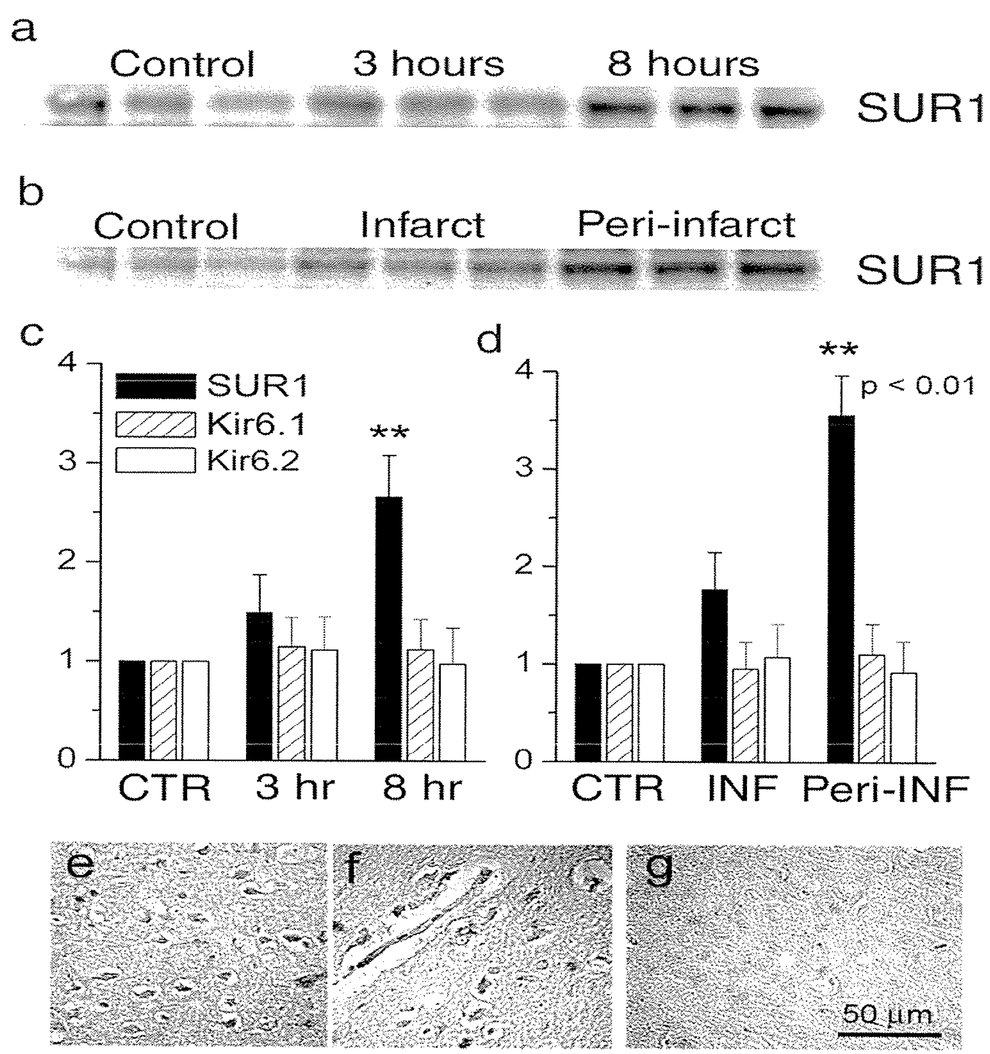
FIGS. 15A-15G show that SUR1 but not Kir6.1 or Kir6.2 is transcriptionally up-regulated in MCA stroke. Western blots for SUR1 (180 kDa) at different times (FIG. 15A) and in different locations (FIG. 15B) after MCA stroke; in (FIG. 15A), lysates were all from TTC(+) peri-infarct regions of the involved hemisphere, obtained at the times indicated; in (FIG. 15B), lysates were all obtained 8 hr after MCA stoke from the regions indicated; each individual lane in a and b is from a single animal. Quantification of the data from (FIG. 15A) and (FIG. 15B), respectively, combined with comparable data for Kir6.1 and Kir6.2; for each individual blot, data were normalized to values of β-actin and to the control data for that blot and analyzed separately; **, $p<0.01$. In situ hybridization for SUR1, 3 hr after MCA stroke; paraffin sections showed that large neuron-like cells (FIG. 15E) and capillaries (FIG. 15F) in the ischemic zone were labeled, whereas tissues from the same areas on the control side were not (FIG. 15G).

Western blots showed an increase in expression of SUR1 protein, most prominently in peri-infarct regions (FIG. 15A-D). However, the pore-forming subunits of $K_{ATP}$ channels, Kir6.1 or Kir6.2, were not up-regulated (FIG. 15C-D). In situ hybridization showed SUR1 transcripts in neurons and capillaries from regions of ischemia that were not present in control tissues (FIG. 15E-G), suggesting that SUR1, but not $K_{ATP}$ channels, was transcriptionally up-regulated in cerebral ischemia.

Thus, these data suggest that SUR1, but not Kir6.1 or Kir6.2, is transcriptionally up-regulated in cerebral ischemia, first in regions that are destined to undergo necrosis, and later in peri-infarct regions.

Example 18

SUR1 Up-Regulation

Figure 16:
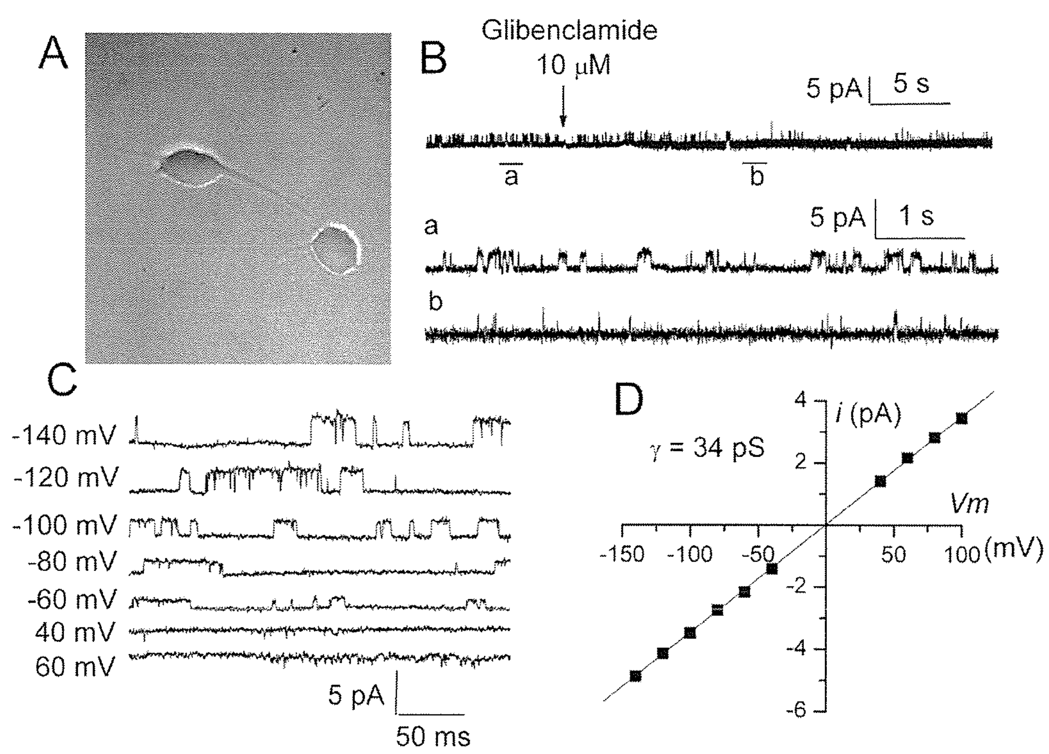
FIGS. 16A-16D show patch clamp recordings of $NC_{CaATP}$ channel in neuron-like cells in stroke.

FIG. 15A-G of the showed that SUR1 was significantly up-regulated in stroke. It also showed that the pore-forming subunits, Kir6.1 and Kir6.2, were not up-regulated in stroke, suggesting that $K_{ATP}$ channels were not involved. To prove that SUR1 up-regulation is due to $NC_{Ca-ATP}$ channels and not to $K_{ATP}$ channels, patch clamp recordings of neurons and endothelial cells from ischemic regions were performed. Large neuron-like cells were enxymatically isolated 3-hr (FIG. 16A) and 6-hr after stroke. Patch clamp study was carried out using $Cs^+$ in the bath and pipette, to block all $K^+$ channels including $K_{ATP}$ channels. These experiments showed robust cation channel activity that was blocked by glibenclamide, as predicted for the $NC_{Ca-ATP}$ channel (FIG. 16B). In addition, when channel activity was recorded with $K^+$, the slope conductance was 34 pS (FIG. 16C,D), as previously reported in freshly isolated R1 astrocytes, and much less than the 70-75 pS reported for KATP channels.

Example 19

Function of SUR1 in Cerebral Ischemia

Figure 17:
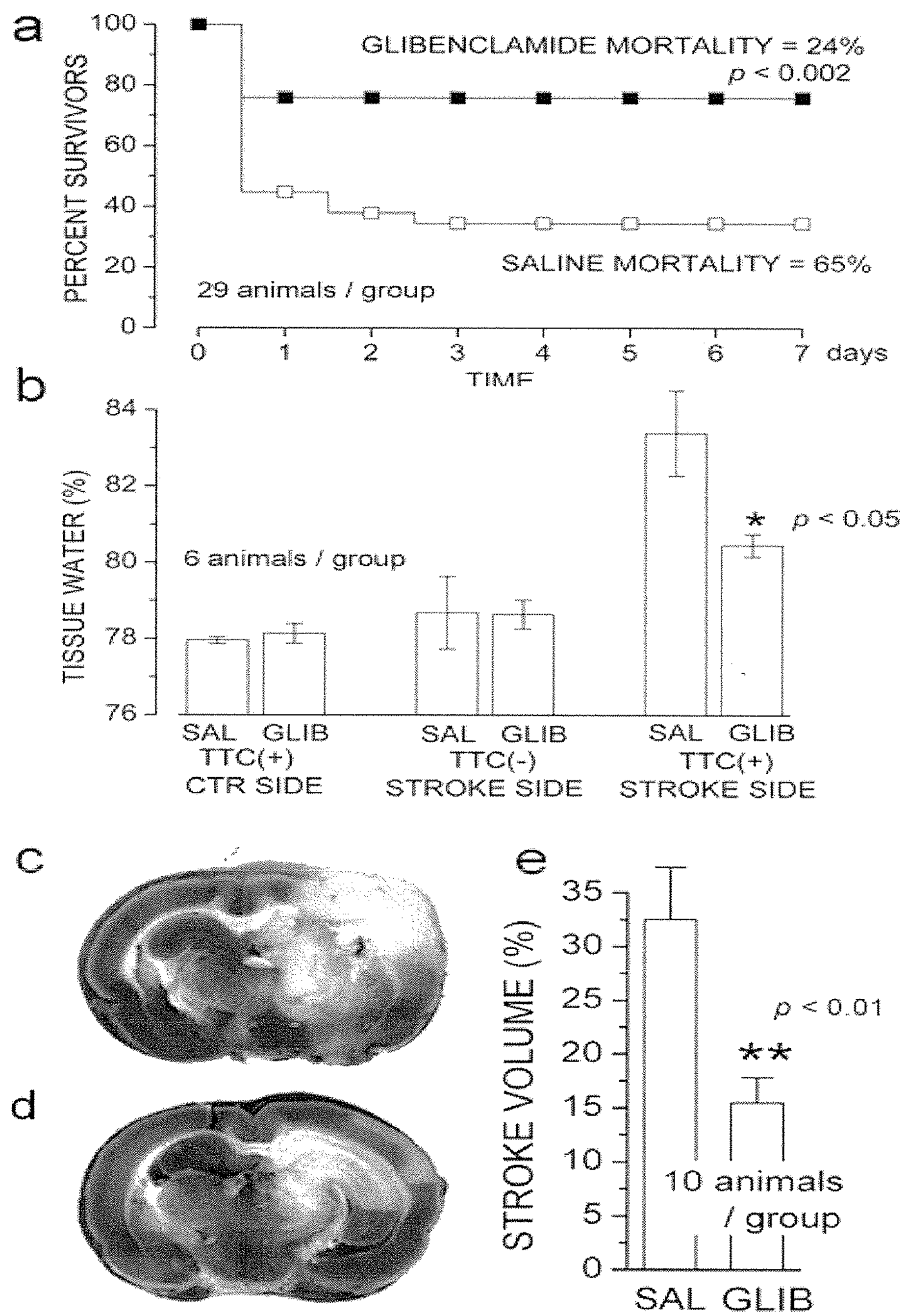
FIGS. 17A-17E show that glibenclamide reduces mortality, edema and stroke size in MCA stroke.

To determine the function of SUR1 that was newly expressed in cerebral ischemia, the effects of glibenclamide, a highly selective inhibitor of SUR1 was studied. The effect of glibenclamide on mortality (MCE model) was studied. In a large group of animals, both male and female, treatment with glibenclamide resulted in a dramatic reduction in mortality compared to saline, from 65% to 24% ($p<0.002$; FIG. 17A).

Since glibenclamide had been shown to ameliorate cytotoxic edema of astrocytes induced by energy depletion (Chen et al., 2003), it was reasoned that the beneficial effect on mortality was related to edema. The effect of glibenclamide on the formation of edema 8 hr after induction of stroke (MCE model) was examined. This is a time that preceded death of any animal in the mortality study. In the first of two experiments, water content in the involved and uninvolved hemispheres was measured using the methods described in Example 14. For the control hemisphere, water was 77.9±0.2%. For the involved hemisphere, water rose by 3.4%, to 81.3±0.5% for the group treated with saline, whereas it rose by only 2.0%, to 79.9±0.3%, for the group treated with glibenclamide. These values were significantly different ($p<0.05$), consistent with an important role of SUR1 in formation of edema.

Next, to better characterize the location of edema, the water content after dividing coronal brain sections into viable TTC(+) and non-viable TTC(−) parts was examined. Water in the uninvolved hemisphere was 78.0±0.1% (FIG. 17B), similar to the previous value of 77.9±0.2%, indicating that TTC processing had not altered water content. For the involved hemisphere, water in the TTC(+) tissue rose by 5.4%, to 83.4±1.1% for the group treated with saline, whereas it rose by only 2.5%, to 80.5±0.3%, for the group treated with glibenclamide (FIG. 17B). These values were significantly different ($p<0.05$). By contrast, values for water in TTC(−) tissues, 78.7±1.0% and 78.6±0.4% with saline and with glibenclamide, respectively, were not different ($p=0.97$), and were only slightly higher than the value for the uninvolved hemisphere (78.0%), reflecting a need for ongoing blood flow to increase tissue water (FIG. 17B) (Ayata & Ropper, 2002).

In these animals, serum glucose at 8 hr when edema was measured remained in a range unlikely to have an effect on ischemia-induced damage (Li et al., 1994; Wass & Lanier, 1996) (122±4 vs. 93±3 mg/dl for saline and glibenclamide-treated animals, respectively; 11 rats/group). Together, these data indicated that the edema was located almost entirely in viable peri-infarct (penumbral) tissue adjacent to the early core of the stroke, and that glibenclamide was highly effective in reducing it, consistent with an important role for SUR1 in formation of edema.

Thus, the data with low-dose glibenclamide, which is highly selective for SUR1 (Gribble & Reimann, 2003; Meyer et al., 1999) provided compelling evidence of a critical role for SUR1 in formation of cerebral edema.

Example 20

The Effect of Stroke Size

A non-lethal thromboembolic (TE) model was used to assess stroke size 48 hr after induction of stroke.

With the TE model, glibenclamide treatment resulted in a highly significant reduction in stroke volume, compared to saline controls (32.5±4.9% vs. 15.5±2.3%; $p<0.01$) (FIG. 17C-E). Essentially all animals, regardless of treatment group, suffered infarctions involving the basal ganglia, which were supplied by terminal lenticulostriate arterioles. However, reduced stroke volumes in the glibenclamide group were often associated with marked sparing of the cerebral cortex (FIG. 17C-D), a phenomenon previously reported with decompressive craniectomy (Doerfler et al., 2001). With glibenclamide, cortical sparing may reflect improved leptomeningeal collateral blood flow due to reduced cerebral edema and reduced intracranial pressure.

Example 21

MCE Model Following Stroke

The fluorescent derivative, BODIPY-glibenclamide, was used to label tissues in vivo following stroke (MCE model).

Figure 18:
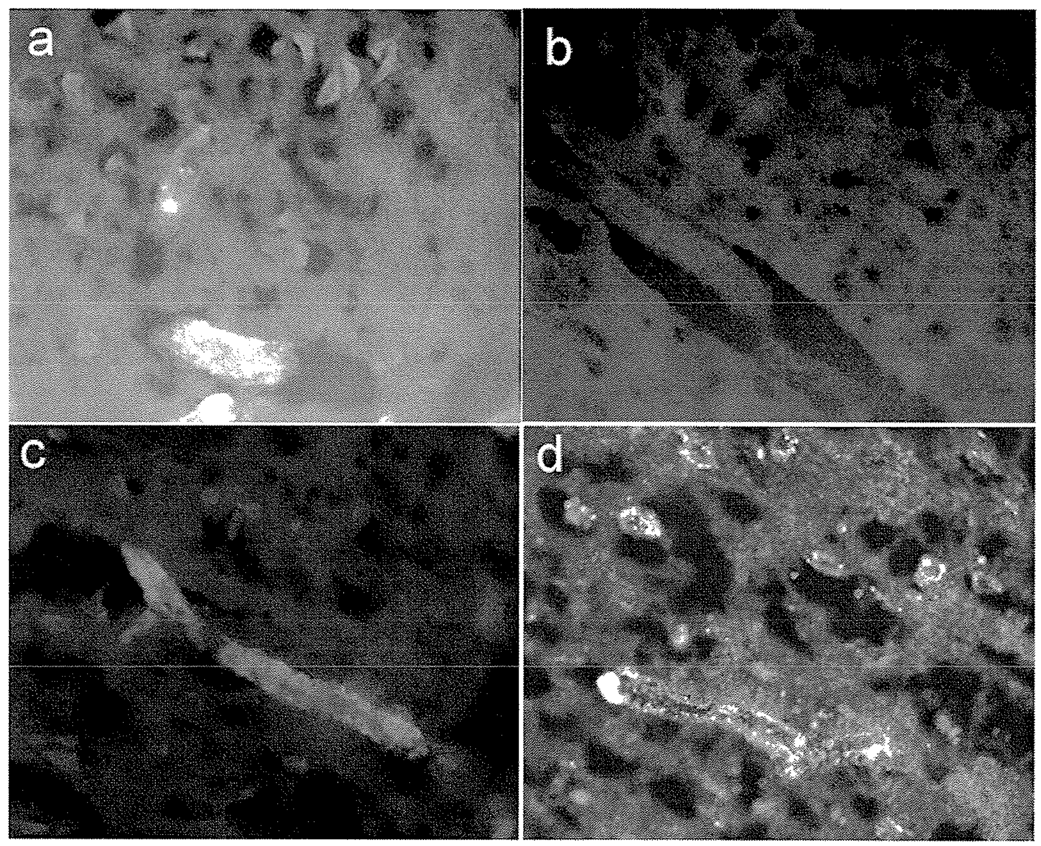
FIGS. 18A-18D show that tissue distribution of BODIPY-glibenclamide in MCA stroke. a-c, Fluorescence images of brain sections in an animal 6 hr after MCA stroke (MCE model) and administration of BODIPY-glibenclamide; fluorescent labeling was evident in cells, microvessels (FIG. 18A) and capillaries (FIG. 18C) from ischemic regions, but not in the contralateral hemisphere (FIG. 18B); the images in (FIGS. 18A, 18B) are from the same animal, taken with the same exposure time; in (FIG. 18C), the single layer of nuclei confirms that the structure brightly labeled by BODIPY-glibenclamide is a capillary.
Figure 19:
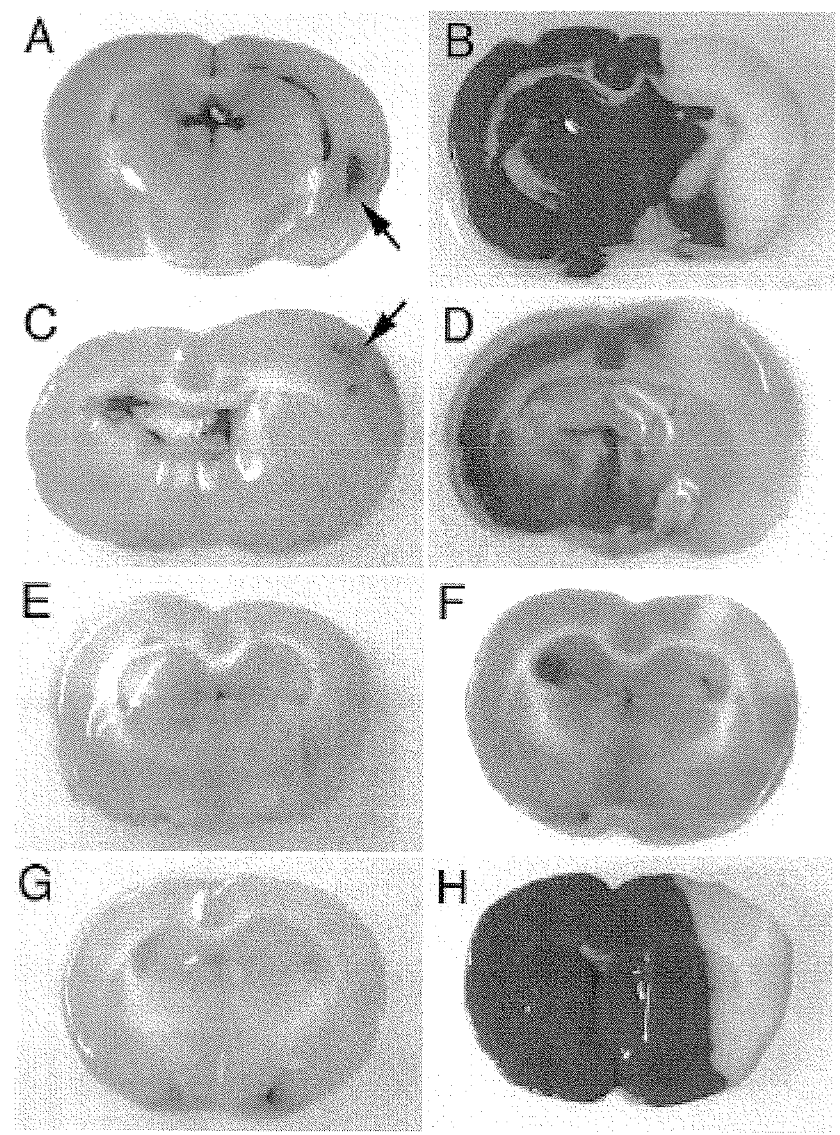

When delivered in the same manner as the parent compound, the fluorescent derivative exhibited similar protective effects, but was less potent [7-day mortality, 40% (n=10); water in the TTC(+) portion of the involved hemisphere at 8 hr, 82.7±1.4% (n=5); serum glucose, 109±4 mg/dl], consistent with reduced efficacy of the labeled drug (Zunkler et al., 2004). The low systemic dose of drug used yielded minimal labeling in the uninvolved hemisphere (FIG. 18B) and pancreas, and none in the unperfused core of the stroke. However, cells in peri-infarct regions were clearly labeled, with well-defined labeling of large neuron-like cells and of microvessels (FIG. 18A), including capillaries (FIG. 18C), that showed prominent expression of SUR1 (FIG. 18D). Preferential cellular labeling in ischemic brain likely reflected not only an increase in glibenclamide binding sites, but also an increase in uptake, possibly due to alteration of the blood brain barrier.

Thus, the data indicated the presence of $NC_{Ca-ATP}$ channels in capillary endothelium and neurons in addition to their previously described presence in astrocytes (Chen et al., 2001; Chen et al., 2003). Additional patch clamp experiments on neurons and microvessels isolated from ischemic cortex 1-6 hr after MCA occlusion (MCE model) confirmed the presence of $NC_{Ca-ATP}$ channels, showing a non-selective cation channel of around 30-35 pS conductance, that was easily recorded with $Cs^+$ as the charge carrier, and that was blocked by glibenclamide. This channel was not present in cells from non-ischemic cerebral tissues.

In view of the above, it is suggested that SUR1-regulated $NC_{Ca-ATP}$ channels that are opened by ATP depletion and that are newly expressed in ischemic neurons, astrocytes and endothelial cells constitute an important, heretofore unidentified pathway for $Na^+$ flux required for formation of cytotoxic and ionic edema. Together, these findings suggest a critical involvement of SUR1 in a new pathway that determines formation of edema following cerebral ischemia. Molecular therapies directed at SUR1 may provide important new avenues for treatment of many types of CNS injuries associated with ischemia.

Example 22

Co-Administration of Glibenclamide and tPA

A rodent model of thromboembolic stroke was used (Aoki et al., 2002; Kijkhuizen et al., 2001; Kano et al., 2000; Sumii et al., 2002; Tejima et al., 2001). Briefly, male spontaneously hypertensive rats that have been fasted overnight are anesthetized using halothane (1-1.5% in a 70/30 mixture of $N_2O/O_2$) with spontaneous respiration (Lee et al., 2004; Sumii et al., 2002). Rectal temperature was maintained at 37° C. with a thermostat-controlled heating pad. The right femoral artery was cannulated, and physiological parameters, including temperature, mean blood pressure, pH, $pO_2$, and $pCO_2$, glucose were monitored. Temporary focal ischemia was obtained with an embolic model that used allogeneic clots to occlude the MCA. Allogeneic, thrombin-induced, fibrin-rich blood clots were prepared using methods adapted from Niessen et al. (Asahi et al., 2000; Niessen et al., 2003; Sumii et al., 2002). Seven clots, 1.5 mm long, were used for embolizing.

Using a ventral cervical incision, the internal and external carotid arteries were exposed. The external carotid artery and pterygopalatine arteries were ligated. Removable surgical clips were applied to the common and internal carotid arteries. The modified PE-50 catheter containing the clots was inserted retrograde into the external carotid artery and advanced up to the internal carotid artery. The temporary clips were removed, and the clots were injected. Incisions were closed.

After stroke, animals were given glucose-free normal saline, 10 ml total, by dermoclysis. Temperature was maintained until animals were awake and were moving about.

Just prior to the time designated for treatment (reperfusion), animals were re-anesthetized and the femoral vein was cannulated. At the time designated for treatment, saline, or a loading dose of glibenclamide (1.5 μg/kg, i.v., Sigma, St. Louis) was first administered. Then, reperfusion was achieved with i.v. administration of rtPA (10 mg/kg, Alteplase, Genetech; dissolved in 2 ml distilled water, given over 30 min) (Buesseb et al., 2002). Then, using a dorsal thoracic incision, a mini-osmotic pump (Alzet 2002, Durect Corporation, Cupertino, Calif.) was implanted subcutaneously that delivered either saline or glibenclamide (300 μM or 148 μg/ml, 0.5 μl/hr s.q.). Physiological parameters, including temperature, mean blood pressure (tail cuff plethysmography), blood gases and glucose were monitored.

At the same time of 6 hr, animals were co-treated with either saline or glibenclamide (loading dose of 1.5 μg/kg i.v. plus implantation of a mini-osmotic pump containing 148 μg/ml=300 μM delivered at ½ μl/hr). Animals were euthanized 24 hr following stroke and brains were perfused to remove blood from the intravascular compartment. Coronal sections of the fresh brains were prepared and photographed, following which sections were processed for TTC staining to identify areas of infarction.

All animals (5/5) co-treated with saline showed large regions of hemorrhagic conversion in cortical and subcortical parenchymal areas of infarction, along with evidence of intraventricular hemorrhage (FIG. 19A-D). In contrast, only 1/5 animals co-treated with glibenclamide had hemorrhagic conversion, with 4/5 showing no evidence of hemorrhage (FIG. 19E-H).

These data suggest that there was protection from hemorrhagic conversion with the administration of glibenclamide, as well as reduction in stroke size, ionic edema, and vasogenic edema.

Example 23

Isolation of Brain Capillaries and Endothelial Cells

The method was adapted in part from Harder et al. (1994) with modifications as previously reported (Seidel, 1991). Briefly, a rat was deeply anesthetized, the descending aorta was ligated, the right atrium was opened and the left ventricle was cannulated to allow perfusion of 50 ml of a physiological solution containing a 1% suspension of iron oxide particles (particle size, 10 μm; Aldrich Chemical Co.). The brain was removed, the pia and pial vessels were stripped away and the cortical mantel is minced into pieces 1-2 $mm^3$ with razor blades. The tissue pieces were incubated with trypsin plus DNAse and then sieved through nylon mesh (210 μm). Retained microvessels were resuspended in collagenase, agitated and incubated at 37° C. for an additional 10 min. To terminate the digestion, microvessels were adhered to the side of the container with a magnet and washed repeatedly to remove enzyme and cellular debris.

Figure 21:
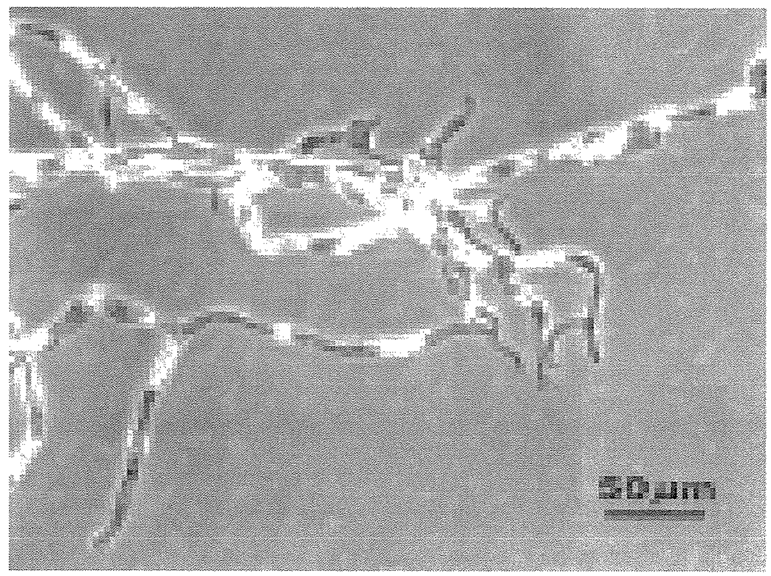
FIG. 21 shows phase contrast photomicrograph of cerebral capillaries freshly isolated from normal brain, after enzymatic cleaning in preparation for patch clamping.

Using these methods yielded healthy-appearing microvascular structures that were suitable for further digestion to obtain single cells (FIG. 21) for further experiments.

Figure 22:
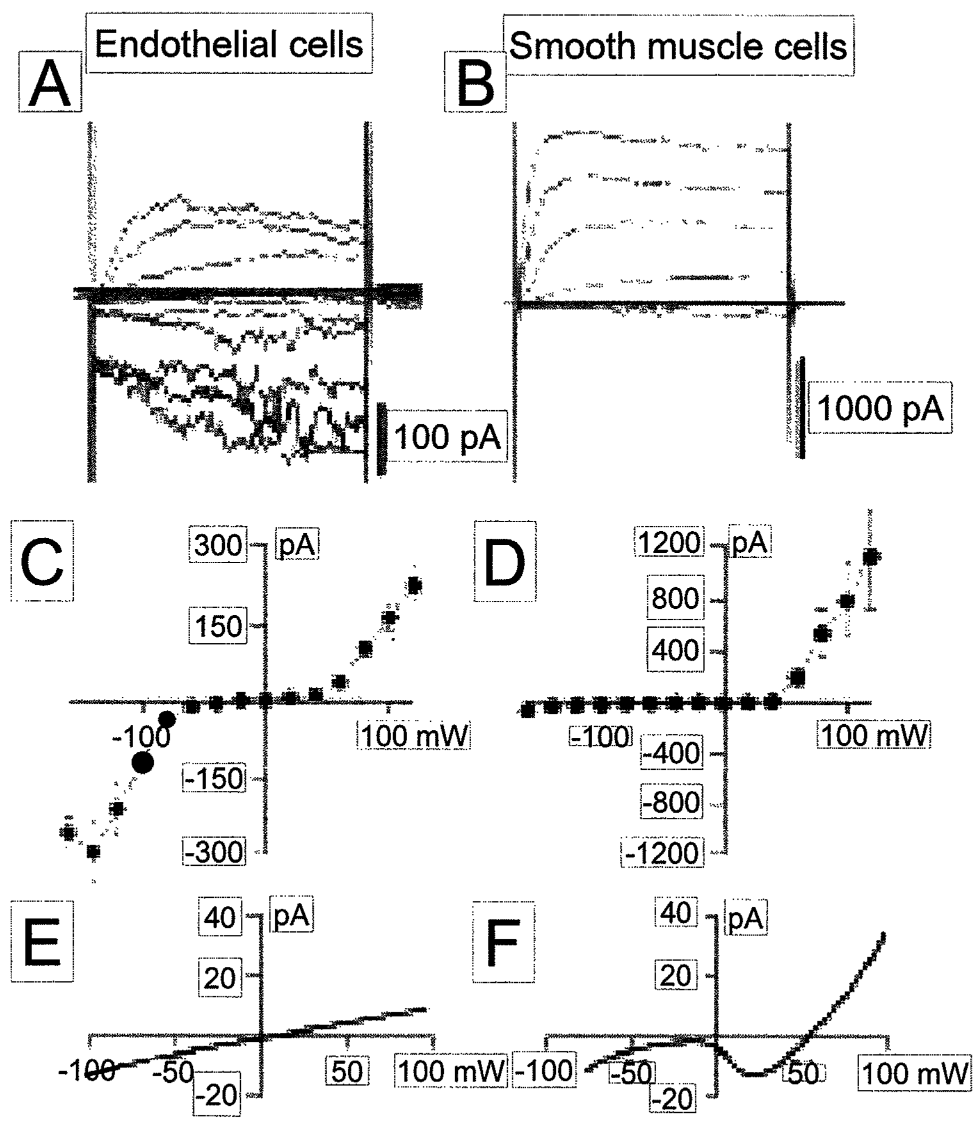
FIGS. 22A-22F show that freshly isolated cerebral endothelial and smooth muscle cells are readily distinguished electrophysiologically.

Isolated endothelial cells were studied using freshly isolated endothelial cells using a nystatin-perforated patch technique. With physiological solutions, the cells exhibited a prominent, strongly rectifying inward current at negative potentials, and a modest outward current at positive potentials (FIG. 22A), yielding a characteristic current-voltage curve with near-zero current at intermediate potentials (FIG. 22C), similar to previous observations in freshly isolated endothelial cells (Hogg et al., 2002). When $K^+$ in the pipette solution was replaced with $Cs^+$, $K^+$ channel currents were completely blocked. In endothelial cells, this yielded a current-voltage curve that was linear (FIG. 22E). These data demonstrated that voltage dependent channels in freshly isolated endothelial cells are exclusively $K^+$ channels that do not carry $Na^+$.

Example 24

Isolation of Neurons

Neurons were isolated from vibratome sections. Immunolabeling experiments indicated that ischemic NeuN-positive neurons expressed SUR1 within 2-3 hr after MCAO, before necrosis was evident. Therefore, tissues were prepared at 2-3 hr after MCAO. The brain was divided coronally at the level of the bregma, and cryosections were prepared from one half and vibratome sections were prepared from the other half. Cryosections (10 μm) were used for TTC staining (Mathews et al., 2000) or alternatively, high-contrast silver infarct staining (SIS), (Vogel et al., 1999) to identify the region of ischemia, and for immunolabeling, to verify SUR1 up-regulation in neurons double labeled for NeuN. Vibratome sections (300 μm) were processed (Hainsworth et al., 2000; Kay et al., 1986; Moyer et al., 1998) to obtain single neurons for patch clamping. Selected portions of coronal slices were incubated at 35° C. in HBSS bubbled with air. After at least 30 min, the pieces were transferred to HBSS containing 1.5 mg/ml protease XIV (Sigma). After 30×0 min of protease treatment, the pieces were rinsed in enzyme-free HBSS and mechanically triturated. For controls, cells from mirror-image cortical areas in the uninvolved hemisphere were used. Cells were allowed to settle in HBSS for 10-12 min in a plastic Petri dish mounted on the stage of an inverted microscope. Large and medium-sized pyramidal-shaped neurons were selected for recordings. At this early time of 2-3 hr, only neurons and capillaries, not astrocytes, show up-regulation of SUR1.

Once the cells were isolated patch clamp experiments using well known methods including whole-cell, inside-out, outside-out and perforated patch were used (Chen et al., 2003; Chen et al., 2001; Perillan et al., 2002; Perillan et al., 2000; Perillan et al., 1999)

Example 25

MMP Inhibition by Glibenclamide

Activation of MMP-9 & MMP-2 in stroke tissue was compared to controls. Briefly, gelatinase activity of recombinant enzyme and stroke tissue under control conditions (CTR), in presence of glibenclamide (10 μM), and in presence of MMP-inhibitor II (300 nM; Calbiochem).

Next, the supernatants underwent a gelatinase purification process with gelatin-Sepharose 4B (Pharmacia), and Zymography was performed on the purified supernatants in sodium dodecyl sulfate gels containing gelatin (Rosenberg, 1994). Dried gels were scanned with a transparency scanner, and images were analyzed by densitometry. The relative lysis of an individual sample was expressed as the integrated density value of its band and divided by the protein content of the sample.

Figure 20:
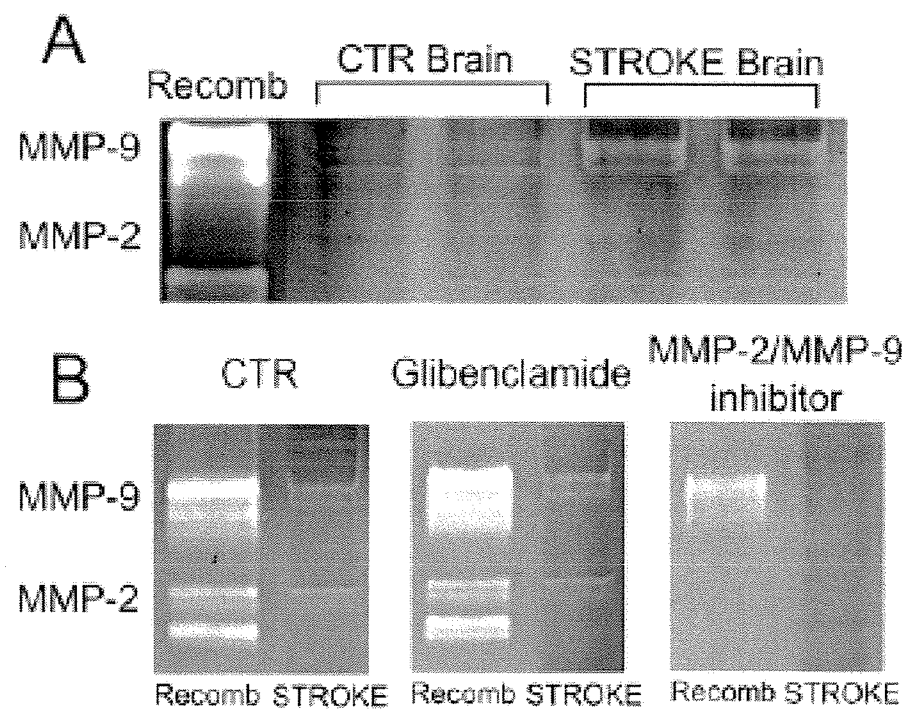
FIGS. 20A-20B show zymography showing gelatinase activity of matrix metalloproteinases (MMP's) in stroke, and absence of direct MMP inhibition by glibenclamide.

Zymography confirmed that gelatinase activity was increased after stroke (FIG. 20A), and showed that gelatinase activity assayed in the presence of glibenclamide (FIG. 20B, Glibenclamide) was the same as that assayed without (FIG. 20B, CTR), although gelatinase activity was strongly inhibited by commercially available MMP inhibitor II (FIG. 20B, MMP-2/MMP-9 inhibitor). These data demonstrated that glibenclamide did not directly inhibit gelatinase activity, and suggested that the reduction of hemorrhagic conversion observed with glibenclamide likely came about due to a beneficial, protective effect of glibenclamide on ischemic endothelial cells.

Example 26

Up-Regulation of SUR1-mRNA in Stroke

Additional molecular evidence for involvement of SUR1 in stroke was obtained using quantitative RT-PCR.

Total RNA was extracted and purified from samples of homogenized brain tissues contralateral (CTR) and ipsilateral to MCAO (STROKE) using guanidine isothyocyonatye. cDNA was synthesized with 4 μg of total RNA per 50 μl of reaction mixture using TaqMan RT kit (Applied Biosystems). Relative values of SUR1-mRNA were obtained by normalizing to H1f0 (histone 1 member 0). The following probes were used SUR1 forward: GAGTCGGACTTCTCGCCCT (SEQ ID NO: 3); SUR1 reverse: CCTTGACAGTGGCCGAACC (SEQ ID NO: 4); SUR1 TaqMan Probe: 6-FAM-TTCCACATCCTGGTCACACCGCTGT (SEQ ID NO: 5) TAMRA; H1f0 forward: CGGACCACCCCAAGTATTCA (SEQ ID NO: 6); H1f0 reverse: GCCGGCACGGTTCTTCT (SEQ ID NO: 7); H1f0 TaqMan Probe: 6-FAM-CATGATCGTGGCTGCTA TCCAGGCA (SEQ ID NO: 8)-TAMRA.

Figure 23:
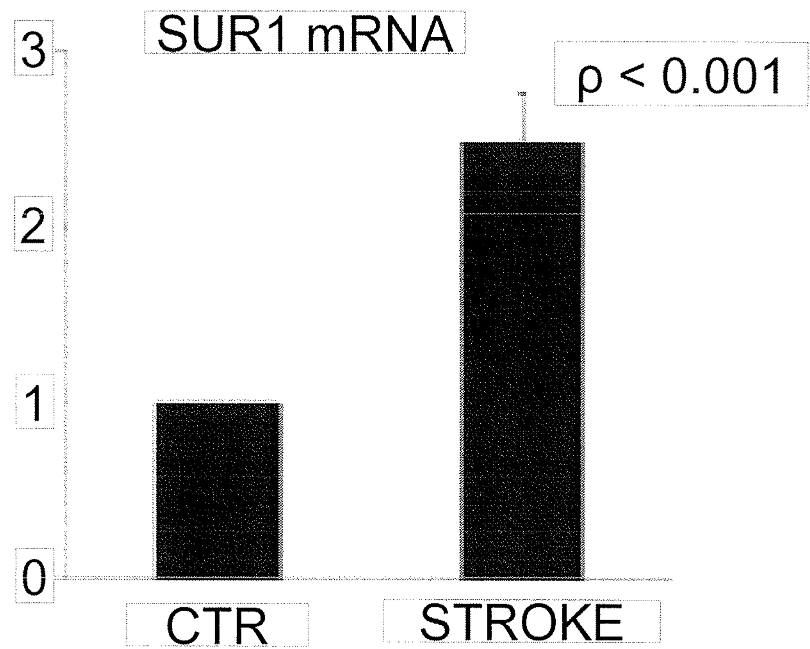
FIG. 23 shows real time RT-PCR showing up-regulation of SUR1-mRNA in stroke.

These data showed that mRNA for SUR1 was significantly increased in the core region, 3 hr after MCAO (FIG. 23).

Example 27

SUR1 Knockdown (SUR1KD) is Protective

To further test involvement of SUR1, SUR1 expression was "knocked down" in situ by infusing oligodeoxynucleotide (ODN) for 14 days using a mini-osmotic pump, with the delivery catheter placed in the gelfoam implantation site in the brain, in the otherwise standard model we use for R1 astrocyte isolation (Perillan et al., 1980, Perillan et al., 2002, Perillan et al., 2000, Perillan et al., 1999). Knockdown of SUR1 expression (SUR1KD) was achieved using antisense (AS; 5'-GGCCGAGTGGTTCTCGGT-3' (SEQ ID NO: 9)) (Yokoshiki et al., 1999) oligodeoxynucleotide (ODN), with scrambled (SCR; 5'-TGCCTGAGGCGTGGCTGT-3' (SEQ ID NO: 10)) ODN being used as control.

Figure 24:
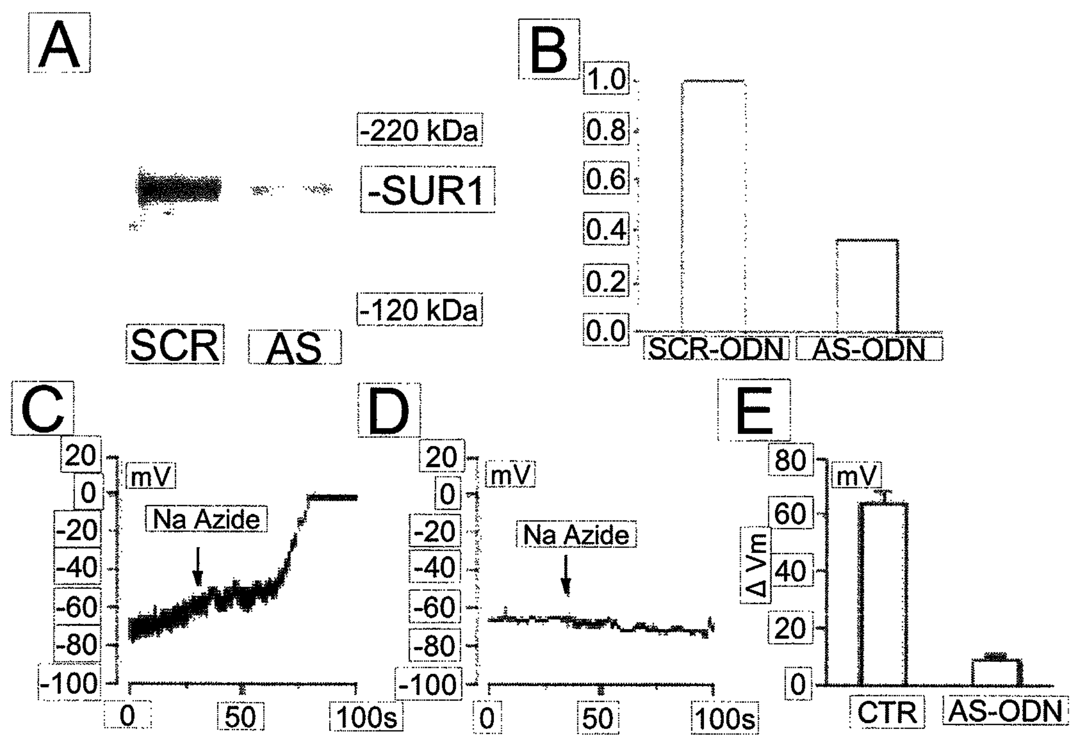
FIGS. 24A-24E show SUR1 knock down (SUR1KD) in R1 astrocytes protects from ATP-depletion-induced depolarization.

Immunoblots of gliotic capsule showed significant reduction in SUR1 expression in SUR1 knockdown (SUR1KD) tissues compared to controls receiving scrambled sequence ODN (FIGS. 24A and 24B).

The inventors enzymatically isolated single cells from SUR1KD and controls using a standard cell isolation protocols described above (Chen et al., 2003) to assess functional responses to ATP depletion induced by Na azide. In R1 astrocytes from control tissues, Na azide (1 mM) caused rapid depolarization due to $Na^+$ influx attributable to activation of $NC_{Ca-ATP}$ channels (FIG. 24C). Notably, this depolarizing response was opposite the hyperpolarizing response observed when $K_{ATP}$ channels were activated. In R1 astrocytes from SUR1KD, however, Na azide had little effect on resting membrane potential (FIG. 24D). In controls, application of Na azide resulted in depolarization of 64±3.7 mV, whereas in cells for SUR1KD, depolarization was only 8.7±1.7 mV (FIG. 24E).

In addition, membrane blebbing that typically follows exposure to Na azide was not observed in cells from SUR1KD, confirming the role for SUR1 in cytotoxic edema of R1 astrocytes.

Example 28

Molecular Factors that Regulate SUR1 Expression

Based on work in pancreatic β cells, a number of SP1 transcription factor binding sites have been identified in the proximal SUR1 promoter region that are considered to be important for activation of SUR1 transcriptional activity (Ashfield et al., 1998; Hilali et al., 2004). Notably, SP1 has essentially not been studied in stroke (Salminen et al., 1995).

Figure 25:
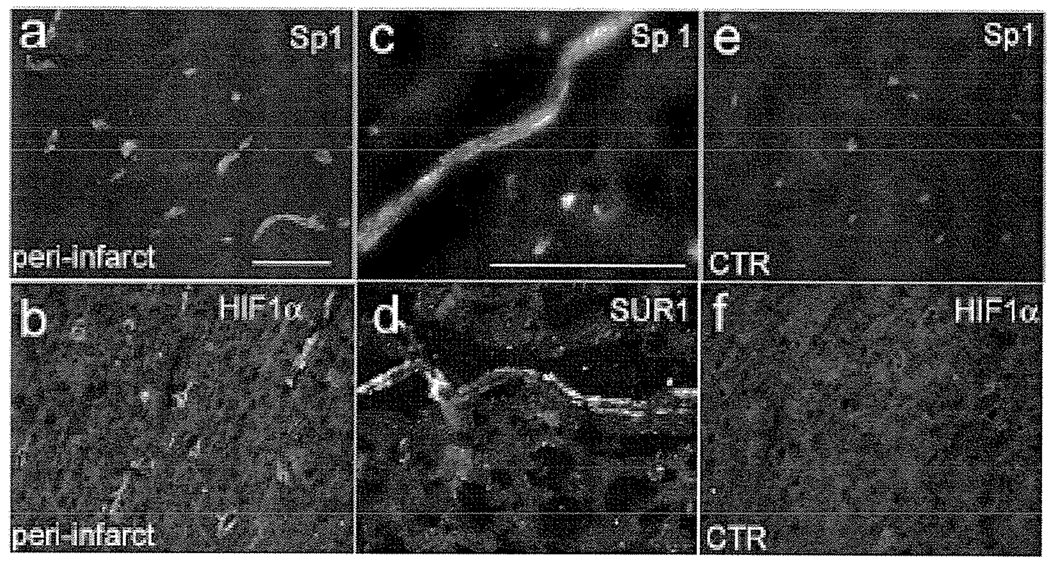
FIGS. 25A-25F show transcription factors in stroke. Immunofluorescence images of subcortical watershed region between ACA and MCA territories, from ipsilateral peri-infarct tissues 8 hr after MCAO (FIGS. 25A-D) and from contralateral control tissues (FIGS. 25E, 25F). The peri-infarct region showed up-regulation of both transcription factors, Sp1 (FIGS. 25A, 25C) and HIF1α (FIG. 25B) in neuron-like cells and capillaries, as well as SUR1 in capillaries (FIG. 25D). Control tissues showed little Sp1 and no HIF1α (FIGS. 25E and 25F).

Briefly, the ischemic peri-infarct tissues was immunolabeled for SP1, which is important for SUR1 expression, for HIF1α, which is widely recognized to be up-regulated in cerebral ischemia (Semenza 2001; Sharp et al., 2000) and for SUR1 itself. SP1 was prominently expressed in large neuron-like cells and in capillaries (FIG. 25A, 25C) in regions confirmed to be ischemic by virtue of expression of HIF1α (FIG. 25B). Notably, capillaries that expressed SP1 also showed prominent expression of SUR1 (FIG. 25C, 25D). Contralateral control tissues showed little immunolabeling for SP1 and none for HIF1α (FIG. 25E, 25F).

Figure 26:
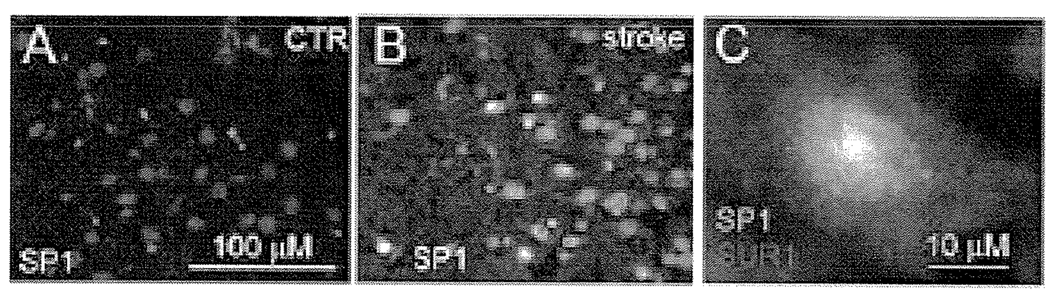
FIGS. 26A-26C show an increase in nuclear localization of the transcription factor, SP1, and SP1 co-localization with SUR1 in stroke. Immunofluorescence images showing increase of nuclear SP1 labeling in ischemic area 3-hr after MCAO (FIG. 26B), compared to contralateral side (FIG. 26A).

Nuclear SP1 localization was significantly augmented early-on in stroke (FIG. 26A, 26B), and nuclear SP1 was found in large neuron-like cells that express SUR1 following MCAO (FIG. 26C).

Figure 27:
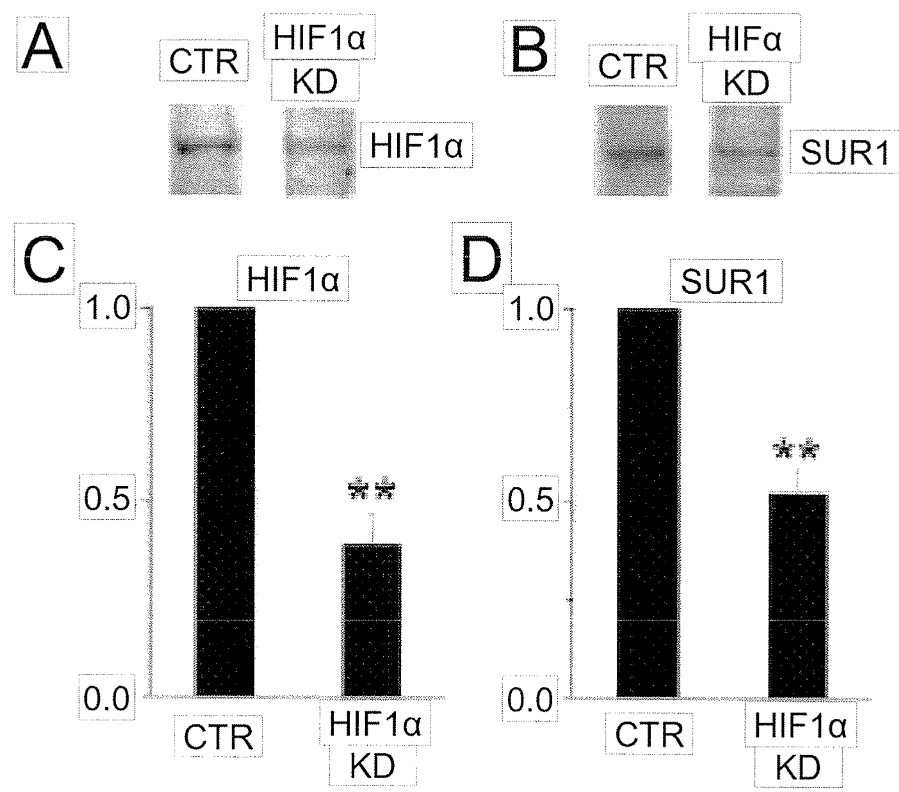
FIGS. 27A-27D show regulation of SUR1 expression by the transcription factor, HIF1α.

HIF1α knock-down animals were obtained by infusion of antisense oligodeoxynucleotide at the site of gelfoam implant. FIG. 27 confirms the HIF1α knock-down animals results in a significant decrease in SUR1 expression (FIG. 27B, 27D), providing strong evidence that not only SP1 but also HIF1α is likely to be an important regulator of SUR1 expression.

REFERENCES

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

Aguilar-Bryan L, et al., Science. 1995; 268:423-426.
Ammala C, et al., Nature. 1996; 379:545-548.
Anisimov, S. V., et al., Mech. Dev. 117, 25-74 (2002).
Aoki K, et al., Acta Neuropathol (Berl). 2003; 106:121-124.
Arteel G E, et al., Eur J. Biochem. 1998; 253:743-750.
Ashcroft F M. Science. 1998; 282:1059-1060.
Ayata, C. & Ropper, A. H. J. Clin. Neurosci. 9, 113-124 (2002).
Babenko A P, et al., Annu Rev Physiol. 1998; 60:667-687.
Ballanyi, K. J. Exp. Biol. 207, 3201-3212 (2004).
Barclay J, et al., J Neurosci. 2002; 22:8139-8147.
Baukrowitz T, et al., Science. 1998; 282:1141-1144.
Becker J B, et al., Ann N Y Acad Sci. 2001; 937:172-187.
Beyer C, et al., J Steroid Biochem Mol Biol. 2002; 81:319-325.
Blurton-Jones M, et al., J Comp Neurol. 2001; 433:115-123.
Bussink J, et al., Radiat Res. 2000; 154:547-555.
Cevolani D, et al., Brain Res Bull. 2001; 54:353-361.
Chen M, et al., J Neurosci. 2003; 23:8568-8577.
Chen M, Simard J M. J Neurosci. 2001; 21:6512-6521
Chen H., et al., J. Neurol. Sci. 118, 109-6 (1993).
Choi I, et al., Mol Cell Endocrinol. 2001; 181:139-150.
Cress A E. Biotechniques. 2000; 29:776-781.
Dalton S, et al., Glia. 2003; 42:325-339.
Dhandapani K, et al., Endocrine. 2003; 21:59-66.
Dhandapani K M, et al., Biol Reprod. 2002; 67:1379-1385.
Dhandapani K M, et al., BMC Neurosci. 2002; 3:6.
Diab A, et al., Infect Immun. 1999; 67:2590-2601.
Doerfiler, A., et al., Stroke 32, 2675-2681 (2001).
Drain P, et al., Proc Natl Acad Sci USA. 1998; 95:13953-13958.
Dubik D et al., Oncogene. 1992; 7:1587-1594.
El Ashry D, et al., J Steroid Biochem Mol Biol. 1996; 59:261-269.
Enkvetchakul D, et al., Biophys J. 2000; 78:2334-2348.
Falk E M, et al., Pharmacol Biochem Behav. 2002; 72:617-622.
Fischer S, et al., J Cell Physiol. 2004; 198:359-369.
Foy M R, et al., Brain Res. 1984; 321:311-314.
Fujita A, et al., Pharmacol Ther. 2000; 85:39-53.
Garcia-Estrada J, et al., Brain Res. 1993; 628:271-278.
Garcia-Ovejero D, et al., J Comp Neurol. 2002; 450:256-271.
Garcia-Segura L M, et al., Prog Neurobiol. 2001; 63:29-60.
Garlid K D, et al., Circ Res. 1997; 81:1072-1082.
Giaccia A J, et al., Int J Radiat Oncol Biol Phys. 1992; 23:891-897.
Gribble, F. M. & Reimann, F. Diabetologia 46, 875-891 (2003).
Grover G J. Can J Physiol Pharmacol. 1997; 75:309-315.
Guo X Z, et al., Cell Res. 2001; 11:321-324.
Hainsworth et al., Neuropharmacology. 2001; 40:784-791.
Hale L P, et al., Am J Physiol Heart Circ Physiol. 2002; 282:H1467-H1477.
Halstead J, et al., J Biol Chem. 1995; 270:13600-13603.
Harder et al., Am J Physiol. 1994; 266:H2098-H2107.
Haruna T, et al., Pflugers Arch. 2000; 441:200-207.
Haug A, et al., Arch Toxicol. 1994; 68:1-7.
Higashijima T, et al., Biol Chem. 1990; 265:14176-14186.
Higgins C F. Annu Rev Cell Biol. 1992; 8:67-113.
Hiroi H, et al., J Mol Endocrinol. 1999; 22:37-44.
Hobbs M V, et al., J Immunol. 1993; 150:3602-3614.
Hogg et al., FEBS Lett. 2002; 522:125-129.
Hogg et al., Lung. 2002; 180:203-214.
Hohenegger M, et al., Proc Natl Acad Sci USA. 1998; 95:346-351.
Honda K, et al., J Neurosci Res. 2000; 60:321-327.
Hossain M A, et al., J Biol Chem. 2000; 275:27874-27882.
Hua Y, et al., J Cereb Blood Flow Metab. 2003; 23:1448-1454.
Hunt R A, et al., Hypertension. 1999; 34:603-608.
Huovinen R, et al., Int J Cancer. 1993; 55:685-691.
Ignotz R A, et al., J Cell Biochem. 2000; 78:588-594.
Inagaki N, et al., Neuron. 1996; 16:1011-1017.
Isomoto S, et al., J Biol Chem. 1996; 271:24321-24324.
Jain, Sci. Amer. 271: 58-65, 1994.
Jorgensen M B, et al., Exp Neurol. 1993; 120:70-88.
Jovanovic A, et al., Lab Invest. 1998; 78:1101-1107.
Kakinuma Y, et al., Clin Sci (Lond). 2002; 103 Suppl 48:210 S-214S.
Kangas L. Cancer Chemother Pharmacol. 1990; 27:8-12.
Kangas L. J Steroid Biochem. 1990; 36:191-195.
Kanthasamy A, et al., Neuroscience. 2002; 114:917-924.
Karschin, C., et al., FEBS Lett. 401, 59-64 (1997).
Kawamura, S., et al., Acta Neurochir. (Wien.) 109, 126-132 (1991).
Kay et al., J Neurosci Methods. 1986; 16:227-238.
Ke C, et al., Neurosci Lett. 2001; 301:21-24.
Kelly M J, et al., Steroids. 1999; 64:64-75.
Kennedy A S, et al., Int J Radiat Oncol Biol Phys. 1997; 37:897-905.
Kielian T, et al., J Immunol. 2001; 166:4634-4643.
Kimura D. Sci Am. 1992; 267:118-125.
Kohshi K, J Neurol Sci. 2003; 209:115-117.
Koster J C, J Gen Physiol. 1999; 114:203-213.
Kucich U, et al., Arch Biochem Biophys. 2000; 374:313-324.
Kuiper G G, et al., Endocrinology. 1997; 138:863-870.
Kuiper G G, et al., Proc Natl Acad Sci USA. 1996; 93:5925-5930.
Larsson O, et al., Diabetes. 2000; 49:1409-1412.

Lawson K. Kidney Int. 2000; 57:838-845.
Le Mellay V, et al., J Cell Biochem. 1999; 75:138-146.
Leaney J L, Tinker A. Proc Natl Acad Sci USA. 2000; 97:5651-5656.
Li, P. A., et al., Neurosci. Lett. 177, 63-65 (1994).
Lieberher T M, et al., J Cell Biochem. 1999; 74:50-60.
Liss B, Roeper J. Mol Membr Biol. 2001; 18:117-127.
Liu Y, et al., Circulation. 1998; 97:2463-2469.
Mateo J, et al., Biochem J. 2003; 376:537-544.
Mathews et al., J Neurosci Methods. 2000; 102:43-51.
McNally J G, et al., Methods. 1999; 19:373-385.
Meyer, M., et al., Br. J. Pharm-acol. 128, 27-34 (1999).
Moon R C, Constantinou A I. Breast Cancer Res Treat. 1997; 46:181-189.
Moyer et al., J Neurosci Methods. 1998; 86:35-54.
Munoz A, et al., Stroke. 2003; 34:164-170.
Murayama T, et al., J Cell Physiol. 1996; 169:448-454.
Murphy K, et al., Mol Pharmacol. 2003; in press.
Nakabayashi, K. et al. AJNR Am. J. Neuroradiol. 18, 485-491 (1997).
Nichols C G, et al., Science. 1996; 272:1785-1787.
Oehmichen M, et al., Exp Toxicol Pathol. 2000; 52:348-352.
Oehmichen M, et al., Neurotoxicology. 2001; 22:99-107.
Olive P L, et al., Br J Cancer. 2000; 83:1525-1531.
Paczynski R P, et al., Stroke. 2000; 31:1702-1708.
Paech K, et al., Science. 1997; 277:1508-1510.
Panten U, et al., Biochem Pharmacol. 1989; 38:1217-1229.
Papadopoulos M C, et al., Mt Sinai J Med. 2002; 69:242-248.
Perillan P R, et al., J Biol Chem. 2002; 277:1974-1980.
Perillan P R, et al., Glia. 1999; 27:213-225.
Perillan P R, et al., Glia. 2000; 31:181-192.
Phillips M I, Zhang Y C. Methods Enzymol. 2000; 313:46-56.
Piiper A, et al., Am J Physiol. 1997; 272:G135-G140.
Pogue B W, et al., Radiat Res. 2001; 155:15-25.
Proks P, et al., J Physiol. 1999; 514 (Pt 1):19-25.
Qiu J, et al., J Neurosci. 2003; 23:9529-9540.
Rama Rao K V, et al., J Neurosci Res. 2003; 74:891-897.
Rama Rao K V, et al., Neuroreport. 2003; 14:2379-2382.
Ramirez V D, Zheng J. Front Neuroendocrinol. 1996; 17:402-439.
Raucher D, et al., Cell 2000; 100:221-228.
Robinson A P, et al., Immunology. 1986; 57:239-247.
Robinson S P, et al., Eur J Cancer Clin Oncol. 1988; 24:1817-1821.
Rohacs T, et al., J Biol Chem. 1999; 274:36065-36072.
Rossignol F, et al., Gene. 2002; 299:135-140.
Ruknudin A, et al., J Biol Chem. 1998; 273:14165-14171.
Ruscher K, et al., J Neurosci. 2002; 22:10291-10301.
Russo J, et al., IARC Sci Publ. 1990; 47-78.
Russo J, Russo I H. Lab Invest. 1987; 57:112-137.
Saadoun S, et al., Br J Cancer. 2002; 87:621-623.
Schubert P, et al., Ann N Y Acad Sci. 2000; 903:24-33.
Seidel et al., Cell Tissue Res. 1991; 265:579-587.
Seino, S. Annu. Rev. Physiol 61, 337-362 (1999).
Semenza G L. Biochem Pharmacol. 2000; 59:47-53.
Shaywitz B A, et al., Nature. 1995; 373:607-609.
Shyng S, et al., J Gen Physiol. 1997; 110:643-654.
Singer C A, et al., J Neurosci. 1999; 19:2455-2463.
Singh M, et al., J Neurosci. 1999; 19:1179-1188.
Smith S S, et al., Brain Res. 1987; 422:40-51.
Smith S S, et al., Brain Res. 1988; 475:272-282.
Sohrabji F, et al., Proc Natl Acad Sci USA. 1995; 92:11110-11114.
Stone D J, et al., J Neurosci. 1998; 18:3180-3185.
Streit W J, et al., Prog Neurobiol. 1999; 57:563-581.
Sun M C, et al., J Neurosurg. 2003; 98:565-569.
Sylvia V L, et al, J Steroid Biochem Mol Biol. 2000; 73:211-224.
Teixeira C, et al., Cancer Res. 1995; 55:3902-3907.
Thrash-Bingham C A, et al., J Natl Cancer Inst. 1999; 91:143-151.
Toker A. Curr Opin Cell Biol. 1998; 10:254-261.
Toomey, J. R et al. Stroke 33, 578-585 (2002).
Toran-Allerand C D. J Steroid Biochem Mol Biol. 1996; 56:169-178.
Torner L, et al., J Neurosci. 2001; 21:3207-3214.
Treherne, J. M. & Ashford, M. L. Neuroscience 40, 523-531 (1991).
Tucker S J, et al., EMBO J. 1998; 17:3290-3296.
Tucker S J, et al., Nature. 1997; 387:179-183.
U.S. Pat. No. 5,637,085
U.S. Pat. No. 6,391,911
Vogel et al., Stroke. 1999; 30:1134-1141.
Wallace W, et al., Biotechniques. 2001; 31:1076-8, 1080, 1082.
Wang J Y, et al., Glia. 2000; 32:155-164.
Wang Y L. Methods Cell Biol. 1998; 56:305-315.
Wass, C. T. & Lanier, W. L. Mayo Clin. Proc. 71, 801-812 (1996).
Wiesener M S, et al., FASEB J. 2003; 17:271-273.
WO 03/079987
Woolley C S. Curr Opin Neurobiol. 1999; 9:349-354.
Xie L H, et al., Proc Natl Acad Sci USA. 1999; 96:15292-15297.
Yajima Y, et al., Endocrinology. 1997; 138:1949-1958.
Young, W. & Constantini, S. The Neurobiology of Central Nervous System Trauma. Salzman, S. K. & Faden, A. I. (eds.), pp. 123-130 (Oxford University Press, New York, 1994).
Zhang L, et al., Brain Res Mol Brain Res. 2002; 103:1-11.
Zhang Y, et al., J Neurosci. 2001; 21:RC176.
Zheng J, Ramirez V D. J Steroid Biochem Mol Biol. 1997; 62:327-336.
Zunkler, B. J., et al., Biochem. Pharmacol. 67, 1437-1444 (2004).

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of treating acute cerebral ischemia in a subject comprising administering to the subject an effective amount of tissue plasminogen activator (tPA) and also administering an effective amount of a compound or a pharmaceutically acceptable salt thereof, said compound or pharmaceutically acceptable salt thereof being effective to inhibit a non-selective monovalent cationic ATP-sensitive ($NC_{Ca-ATP}$) channel and to:

a) increase the therapeutic window for the administration of tPA, or b) reduce hemorrhagic conversion, cell swelling, or edema, or c) both a) and b), wherein the compound is a sulfonylurea compound, a benzamido derivative, LY397364, or LY389382.

2. The method of claim 1, wherein the channel is expressed on neuronal cells, neuroglia cells, neural endothelial cells or a combination thereof.

3. The method of claim 1, wherein the compound is selected from the group consisting of glibenclamide, tolbutamide, repaglinide, nateglinide, meglitinide, glyclazide, and glimepiride.

4. The method of claim 3, wherein the amount of the compound administered to the subject is in the range of 0.0001 μg/kg/day to 20 mg/kg/day.

5. The method of claim 4, wherein the amount of the compound administered to the subject is in the range of 0.01 μg/kg/day to 100 μg/kg/day.

6. The method of claim 4, wherein the amount of the compound administered to the subject is in the range of 100 μg/kg/day to 20 mg/kg/day.

7. The method of claim 4, wherein the compound is administered as a bolus injection.

8. The method of claim 4, wherein the compound is administered as an infusion.

9. The method of claim 4, wherein the compound is administered as a bolus injection in combination with an infusion.

10. The method of claim 3, wherein the amount of the compound administered to the subject is in the range of 0.0001 μg/kg/treatment to 20 mg/kg/treatment.

11. The method of claim 10, wherein the amount of the compound administered to the subject is in the range of 0.01 μg/kg/treatment to 100 μg/kg/treatment.

12. The method of claim 10, wherein the amount of the compound administered to the subject is in the range of 100 μg/kg/treatment to 20 mg/kg/treatment.

13. The method of claim 1, wherein the compound inhibits the influx of Na+ into the cells thereby reducing or preventing depolarization of the cells.

14. The method of claim 1, wherein the compound inhibits the influx of Na+ into the cells thereby reducing or preventing cytotoxic edema.

15. The method of claim 1, wherein the treatment reduces hemorrhagic conversion.

16. The method of claim 1, wherein the treatment reduces cell death of cells selected from the group consisting of neuronal cells, endothelial cells, and both neuronal and endothelial cells.

17. The method of claim 1, wherein the compound is administered to the subject before the tPA is administered to the subject.

18. The method of claim 1, wherein the compound is administered to the subject after the tPA is administered to the subject.

19. The method of claim 1, wherein the compound is administered to the subject at the same time the tPA is administered to the subject.

20. A method of reducing mortality of a subject suffering from a stroke comprising administering to the subject an effective amount of tPA and a compound effective to inhibit a non-selective monovalent cationic ATP-sensitive ($NC_{Ca-ATP}$) channel in a neuronal cell, a neuroglia cell, an endothelial cell or a combination thereof, and that is effective to a) increase the therapeutic window for the administration of tPA, or b) reduce hemorrhagic conversion, cell swelling, or edema, or c) both a) and b), wherein the compound is a sulfonylurea compound, a benzamido derivative, LY397364, or LY389382.

21. The method of claim 20, wherein the compound reduces stroke size.

22. The method of claim 20, wherein the compound reduces edema located in the peri-infarct tissue.

23. The method of claim 20, wherein the compound is administered alimentarily or parenterally.

24. The method of claim 23, wherein alimentarily comprises orally, buccally, rectally or sublingually.

25. The method of claim 23, wherein parenterally comprises intravenously, intradermally, intramuscularly, intraarterially, intrathecally, subcutaneously, intraperitoneally, or intraventricularly.

26. The method of claim 23, wherein parenterally comprises injection into the brain parenchyma.

27. The method of claim 20, wherein the compound is administered topically or mucosally.

28. The method of claim 27, wherein topically comprises transdermally.

29. The method of claim 20, wherein the compound is administered to the subject before the tPA is administered to the subject.

30. The method of claim 20, wherein the compound is administered to the subject after the tPA is administered to the subject.

31. The method of claim 20, wherein the compound is administered to the subject at the same time the tPA is administered to the subject.

32. A method of reducing edema in a peri-infarct tissue area of a subject comprising administering to the subject an effective amount of tPA and a compound effective to inhibit a non-selective monovalent cationic ATP-sensitive ($NC_{Ca-ATP}$) channel in a neuronal cell, a neuroglia cell, a neural endothelial cell or a combination thereof, and that is effective to a) increase the therapeutic window for the administration of tPA, or b) reduce hemorrhagic conversion, cell swelling, or edema, or c) both a) and b), wherein the compound is a sulfonylurea compound, a benzamido derivative, LY397364, or LY389382.

33. The method of claim 32, wherein the compound is administered to the subject before the tPA is administered to the subject.

34. The method of claim 32, wherein the compound is administered to the subject after the tPA is administered to the subject.

35. The method of claim 32, wherein the compound is administered to the subject at the same time the tPA is administered to the subject.

36. A method of treating a subject at risk for developing a stroke comprising administering to the subject an effective amount of tPA and a compound effective to inhibit a non-selective monovalent cationic ATP-sensitive ($NC_{Ca-ATP}$) channel in neuronal cell, a neuroglia cell, a neural endothelial cell or a combination thereof, and that is effective to a) increase the therapeutic window for the administration of tPA, or b) reduce hemorrhagic conversion, cell swelling, or edema, or c) both a) and b), wherein the compound is a sulfonylurea compound, a benzamido derivative, LY397364, or LY389382.

37. The method of claim 36, wherein the subject is undergoing treatment for a cardiac condition.

38. The method of claim 37, wherein the cardiac condition is myocardial infarction.

39. The method of claim 36, wherein the subject suffers from an atrial fibrillation or a clotting disorder.

40. The method of claim 39 further comprising administering an anticoagulant in combination with the compound effective to inhibit the $NC_{Ca\_ATP}$ channel.

41. The method of claim 40, wherein the anticoagulant is warfarin or coumadin.

42. The method of claim 36, wherein the subject has a risk of developing pulmonary emboli.

43. The method of claim 36, wherein the subject is undergoing a treatment that increases the subject's risk of stroke.

44. The method of claim 43, wherein the treatment is surgery.

45. The method of claim 44, wherein the surgery is vascular surgery or neurological surgery.

46. The method of claim 43, wherein the treatment is cerebral/endovascular treatment, angiography or stent placement.

47. A method of treating a subject at risk for developing cerebral edema comprising administering to the subject an effective amount of tPA and a compound effective to inhibit a non-selective monovalent cationic ATP-sensitive ($NC_{Ca-ATP}$) channel in a neuronal cell, a neuroglia cell, a neural endothelial cell or a combination thereof, and that is effective to a) increase the therapeutic window for the administration of tPA, or b) reduce hemorrhagic conversion, cell swelling, or edema, or c) both a) and b), wherein the compound is a sulfonylurea compound, a benzamido derivative, LY397364, or LY389382.

48. The method of claim 47, wherein the subject is suffering from an arterior-venous malformation or a mass-occupying lesion.

49. The method of claim 47, wherein the subject is involved in activities that have an increased risk of brain trauma.

50. The method of claim 1, wherein the compound is glibenclamide.

51. The method of claim 20, wherein the compound is glibenclamide.

52. The method of claim 32, wherein the compound is glibenclamide.

53. The method of claim 36, wherein the compound is glibenclamide.

54. The method of claim 47, wherein the compound is glibenclamide.

* * * * *

SEQUENCE LISTING

<160> NUMBER OF SEQ ID NOS: 10

<210> SEQ ID NO 1
<211> LENGTH: 17
<212> TYPE: DNA
<213> ORGANISM: Artificial Sequence
<220> FEATURE:
<223> OTHER INFORMATION: Synthetic Artificial Primer

<400> SEQUENCE: 1
aagcacgtca acgccct 17

<210> SEQ ID NO 2
<211> LENGTH: 19
<212> TYPE: DNA
<213> ORGANISM: Artificial Sequence
<220> FEATURE:
<223> OTHER INFORMATION: Synthetic Artificial Primer

<400> SEQUENCE: 2
gaagcttttc cggcttgtc 19

<210> SEQ ID NO 3
<211> LENGTH: 19
<212> TYPE: DNA
<213> ORGANISM: Artificial Sequence
<220> FEATURE:
<223> OTHER INFORMATION: Synthetic Artificial Primer

<400> SEQUENCE: 3
gagtcggact tctcgccct 19

<210> SEQ ID NO 4
<211> LENGTH: 19
<212> TYPE: DNA
<213> ORGANISM: Artificial Sequence
<220> FEATURE:
<223> OTHER INFORMATION: Synthetic Artificial Primer

<400> SEQUENCE: 4
ccttgacagt ggccgaacc 19

<210> SEQ ID NO 5
<211> LENGTH: 25
<212> TYPE: DNA
<213> ORGANISM: Artificial Sequence
<220> FEATURE:
<223> OTHER INFORMATION: Synthetic Artificial Primer

<400> SEQUENCE: 5
ttccacatcc tggtcacacc gctgt 25

<210> SEQ ID NO 6
<211> LENGTH: 20
<212> TYPE: DNA
<213> ORGANISM: Artificial Sequence
<220> FEATURE:
<223> OTHER INFORMATION: Synthetic Artificial Primer

<400> SEQUENCE: 6
cggaccaccc caagtattca 20

<210> SEQ ID NO 7
<211> LENGTH: 17
<212> TYPE: DNA
<213> ORGANISM: Artificial Sequence -continued

```
<220> FEATURE:
<223> OTHER INFORMATION: Synthetic Artificial Primer

<400> SEQUENCE: 7

gccggcacgg ttcttct                                          17


<210> SEQ ID NO 8
<211> LENGTH: 25
<212> TYPE: DNA
<213> ORGANISM: Artificial Sequence
<220> FEATURE:
<223> OTHER INFORMATION: Synthetic Artificial Primer

<400> SEQUENCE: 8

catgatcgtg gctgctatcc aggca                                 25


<210> SEQ ID NO 9
<211> LENGTH: 18
<212> TYPE: DNA
<213> ORGANISM: Artificial Sequence
<220> FEATURE:
<223> OTHER INFORMATION: Synthetic Artificial Primer

<400> SEQUENCE: 9

ggccgagtgg ttctcggt                                         18


<210> SEQ ID NO 10
<211> LENGTH: 18
<212> TYPE: DNA
<213> ORGANISM: Artificial Sequence
<220> FEATURE:
<223> OTHER INFORMATION: Synthetic Artificial Primer

<400> SEQUENCE: 10

tgcctgaggc gtggctgt                                         18
```